(12) United States Patent
Rouviere et al.

(10) Patent No.: US 9,062,312 B2
(45) Date of Patent: *Jun. 23, 2015

(54) FUSION PEPTIDES COMPRISING MULTI-FUNCTIONAL PEPTIDIC SOLUBILITY TAGS FOR EFFICIENT PRODUCTION, PROCESSING AND SURFACE APPLICATIONS

(75) Inventors: Pierre E Rouviere, Wilmington, DE (US); Tanja Maria Gruber, Media, PA (US); Kari A Fosser, Wilmington, DE (US); Stephen R Fahnestock, Wilmington, DE (US)

(73) Assignee: Danisco US Inc., Palo Alto, CA (US)

( * ) Notice: Subject to any disclaimer, the term of this patent is extended or adjusted under 35 U.S.C. 154(b) by 8 days.

This patent is subject to a terminal disclaimer.

(21) Appl. No.: 13/528,201

(22) Filed: Jun. 20, 2012

(65) Prior Publication Data
US 2013/0164353 A1    Jun. 27, 2013

Related U.S. Application Data

(60) Provisional application No. 61/499,380, filed on Jun. 21, 2011.

(51) Int. Cl.
| | | |
|---|---|---|
| *C07K 14/00* | (2006.01) |
| *A61K 8/02* | (2006.01) |
| *A61Q 11/00* | (2006.01) |
| *A61Q 17/04* | (2006.01) |
| *A61Q 5/08* | (2006.01) |
| *A61Q 5/06* | (2006.01) |
| *A61Q 5/02* | (2006.01) |
| *A61Q 5/12* | (2006.01) |
| *C12N 15/62* | (2006.01) |
| *A61K 8/64* | (2006.01) |
| *A61Q 19/00* | (2006.01) |

(52) U.S. Cl.
CPC ............... *C12N 15/62* (2013.01); *C07K 14/00* (2013.01); *A61K 8/0241* (2013.01); *A61Q 11/00* (2013.01); *A61Q 17/04* (2013.01); *A61Q 5/08* (2013.01); *A61Q 5/06* (2013.01); *A61Q 5/065* (2013.01); *A61Q 5/02* (2013.01); *A61Q 5/12* (2013.01); *Y10T 428/2982* (2015.01); *C07K 2319/01* (2013.01); *C07K 2319/20* (2013.01); *C07K 2319/74* (2013.01); *A61K 8/64* (2013.01); *A61Q 19/00* (2013.01); *A61K 2800/10* (2013.01)

(58) Field of Classification Search
CPC ... A61K 8/0241; A61K 2800/10; A61K 8/64; A61Q 11/00; A61Q 17/04; A61Q 5/02; A61Q 5/06; A61Q 5/065; A61Q 5/08; A61Q 5/12; A61Q 19/00; C07K 14/00; C07K 19/00; C07K 2319/01; C07K 2319/20; C07K 2319/74; C12N 15/62; Y10T 428/2982
See application file for complete search history.

(56) References Cited

U.S. PATENT DOCUMENTS

| | | |
|---|---|---|
| 5,206,154 A | 4/1993 | Lai et al. |
| 5,215,896 A | 6/1993 | Keck et al. |
| 5,302,526 A | 4/1994 | Keck et al. |
| 5,330,902 A | 7/1994 | Keck et al. |
| 5,648,244 A | 7/1997 | Kuliopulos et al. |
| 6,037,145 A | 3/2000 | Yabuta et al. |
| 6,242,219 B1 | 6/2001 | Better et al. |
| 6,613,548 B1 | 9/2003 | Chu |
| 6,815,426 B2 | 11/2004 | Scialdone et al. |
| 7,220,405 B2 | 5/2007 | Huang et al. |
| 7,285,264 B2 | 10/2007 | O'Brien et al. |
| 7,309,482 B2 | 12/2007 | Buseman-Williams et al. |
| 7,341,604 B2 | 3/2008 | Rothe et al. |
| 7,427,656 B2 | 9/2008 | Decarolis et al. |
| 7,501,484 B2 | 3/2009 | Williams et al. |
| 7,632,919 B2 | 12/2009 | Cunningham et al. |
| 7,662,587 B1 | 2/2010 | Cheng et al. |
| 7,662,913 B2 | 2/2010 | Decarolis et al. |
| 7,678,883 B2 | 3/2010 | Cheng et al. |
| 7,700,716 B2 | 4/2010 | Cunningham et al. |
| 7,709,601 B2 | 5/2010 | Cunningham et al. |
| 7,732,569 B2 | 6/2010 | Decarolis et al. |
| 7,736,633 B2 | 6/2010 | Beck et al. |
| 7,749,957 B2 | 7/2010 | Ittel et al. |
| 7,754,680 B2 | 7/2010 | Cunningham et al. |
| 7,794,979 B2 | 9/2010 | Cheng et al. |
| 7,795,382 B2 | 9/2010 | Decarolis et al. |
| 7,807,141 B2 | 10/2010 | Huang et al. |
| 7,829,311 B2 | 11/2010 | DeCarolis et al. |

(Continued)

FOREIGN PATENT DOCUMENTS

| | | |
|---|---|---|
| WO | WO94/04688 | 3/1994 |
| WO | WO01/79479 | 10/2001 |

(Continued)

OTHER PUBLICATIONS

Rudinger, Peptide Hormones, JA Parsons, Ed., 1976, pp. 1-7.*
SIGMA, 2004, pp. 1-2.*
Berendsen, A Glimpae of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-494.*
Bradley et al., Limits of Cooperativity in a Structurally Modular Protein: Response of the Notch Ankyrin Domain to Analogous Alanine Substitutions in Each Repeat, J. Mol. BIoL (2002) 324, 373-386.*
Brown, S., "Metal-recognition by repeating polypeptide." *Nat. Biotechnol.* 15: 269-272, 1997.

(Continued)

*Primary Examiner* — James H Alstrum Acevedo
*Assistant Examiner* — Erinne Dabkowski
(74) *Attorney, Agent, or Firm* — Danisco US Inc.

(57) ABSTRACT

Compositions and methods using fusion peptides comprising multi-functional solubility tags are provided. The multi-functional peptidic solubility tags facilitates more efficient fusion peptide production, easier downstream processing of the fusion peptide, and may be used to provide functional surface properties when coupled to a target material.

11 Claims, 3 Drawing Sheets

(56) References Cited

U.S. PATENT DOCUMENTS

| | | |
|---|---|---|
| 7,906,617 B2 | 3/2011 | Cunningham et al. |
| 2005/0226839 A1 | 10/2005 | Huang et al. |
| 2006/0007311 A1 | 1/2006 | Watanabe |
| 2006/0199206 A1 | 9/2006 | Wang et al. |
| 2007/0065387 A1 | 3/2007 | Beck et al. |
| 2007/0110686 A1 | 5/2007 | Lowe et al. |
| 2007/0196305 A1 | 8/2007 | Wang et al. |
| 2007/0264720 A1 | 11/2007 | Cunningham et al. |
| 2008/0107614 A1 | 5/2008 | Fahnestock et al. |
| 2009/0029412 A1* | 1/2009 | Cheng et al. ............ 435/68.1 |
| 2009/0029420 A1 | 1/2009 | Decarolis et al. |
| 2009/0043075 A1 | 2/2009 | Alsop et al. |
| 2010/0136621 A1* | 6/2010 | Cheng et al. ............ 435/69.1 |
| 2010/0158822 A1 | 6/2010 | Fahnestock et al. |
| 2010/0158837 A1 | 6/2010 | Fahnestock et al. |
| 2010/0158846 A1 | 6/2010 | Fahnestock et al. |
| 2010/0158847 A1 | 6/2010 | Fahnestock et al. |
| 2010/0247457 A1 | 9/2010 | Anton et al. |
| 2010/0247589 A1 | 9/2010 | Fahnestock et al. |

FOREIGN PATENT DOCUMENTS

| | | |
|---|---|---|
| WO | WO03/100022 | 12/2003 |
| WO | WO2004/048399 | 6/2004 |
| WO | WO2008/054746 | 5/2008 |
| WO | WO2008/073368 | 6/2008 |

OTHER PUBLICATIONS

Haught, C., et al., "Recombinant Production and Purification of Novel Antisense Antimicrobial Peptide in *Escherichia coli*." *Biotechnol. Bioengin.* 57:55-61, 1998.

International Search Report and the Written Opinion of the International Searching Authority for International Application No. PCT/US2012/043537 dated Oct. 30, 2012.

International Preliminary Report on Patentability for International Application No. PCT/US2012/043537 dated Dec. 23, 20013.

* cited by examiner

FUSION PEPTIDES COMPRISING MULTI-FUNCTIONAL PEPTIDIC SOLUBILITY TAGS FOR EFFICIENT PRODUCTION, PROCESSING AND SURFACE APPLICATIONS

CROSS-REFERENCE TO RELATED APPLICATIONS

This application claims benefit of U.S. Provisional Patent Application No. 61/499,380, filed Jun. 21, 2011, which is incorporated by reference herein in its entirety.

SEQUENCE LISTING

The sequence listing submitted via EFS, in compliance with 37 C.F.R. §1.52(e), is incorporated herein by reference. The sequence listing text file submitted via EFS contains the file "20120620_CL4320USNP_SeqListST25.txt" created on Jun. 20, 2012, which is 189,567 bytes in size.

FIELD OF THE INVENTION

This invention relates to the field of recombinant production of fusion peptides comprising at least one multi-functional peptidic solubility tag coupled to a peptide of interest. In addition to inducing inclusion body formation for production in an expression host, the solubility tag facilitates controlled solubilization for more efficient downstream processing and provides surface functionalizing activity when associated with a target material.

BACKGROUND OF THE INVENTION

The efficient production of bioactive proteins and peptides has become a hallmark of the biomedical and industrial biochemical industry. Bioactive peptides and proteins are used as curative agents in a variety of diseases such as diabetes (insulin), viral infections and leukemia (interferon), diseases of the immune system (interleukins), and red blood cell deficiencies (erythropoietin) to name a few. Additionally, large quantities of proteins and peptides are needed for various industrial applications including, for example, the pulp and paper industries, textiles, food industries, personal care and cosmetics industries, sugar refining, wastewater treatment, production of alcoholic beverages and as catalysts for the generation of new pharmaceuticals.

In some cases commercially-useful proteins and peptides may be synthetically produced or isolated from natural sources. However, these methods are often expensive, time consuming, and characterized by limited production capacity. Recombinant microbial production may be use to commercially produce the desired peptide/protein. Although preferable to synthesis or isolation, recombinant expression of peptides has a number of obstacles to be overcome in order to be a cost-effective means of production. For example, peptides (and in particular short peptides) produced in a cellular environment are susceptible to degradation from the action of native cellular proteases. Additionally, purification can be difficult, resulting in poor yields depending on the nature of the protein or peptide of interest.

One means to mitigate the above difficulties is the use of a genetic chimera for protein and peptide expression. A chimeric protein or "fusion protein" is a polypeptide comprising at least one portion of the desired protein product fused to at least one portion comprising a peptide tag. The peptide tag may be used to assist protein folding, assist post expression purification, protect the protein from the action of degradative enzymes, and/or assist the protein in passing through the cell membrane.

In many cases it is useful to express a peptide in an insoluble form, particularly when the peptide of interest is rather short, soluble, and/or subject to proteolytic degradation within the host cell. Production of the peptide in insoluble form both facilitates simple recovery and protects the peptide from the undesirable proteolytic degradation. One means to produce the peptide in insoluble form is to recombinantly produce the peptide as part of an insoluble fusion peptide by including within the fusion peptide at least one peptidic solubility tag (i.e., an "inclusion body tag" or "IBT") that induces inclusion body formation. Typically, the fusion peptide is designed to include at least one cleavable peptide linker separating the inclusion body tag from the peptide of interest so that the peptide of interest can be subsequently recovered from the fusion peptide. The fusion peptide may be designed to include a plurality of inclusion body tags, cleavable peptide linkers, and regions encoding the peptide of interest.

Fusion proteins comprising a peptide tag that facilitate the expression of insoluble proteins are well known in the art. The solubility tag of the chimeric or fusion protein is often large, increasing the likelihood that the fusion protein will be insoluble. Example of large peptide solubility tags include, but are not limited to chloramphenicol acetyltransferase (Dykes et al., *Eur. J. Biochem.*, 174:411 (1988), β-galactosidase (Schellenberger et al., *Int. J. Peptide Protein Res.*, 41:326 (1993); Shen et al., *Proc. Nat. Acad. Sci. USA* 281: 4627 (1984); and Kempe et al., *Gene*, 39:239 (1985)), glutathione-S-transferase (Ray et al., *Bio/Technology*, 11:64 (1993) and Hancock et al. (WO94/04688)), the N-terminus of L-ribulokinase (U.S. Pat. No. 5,206,154 and Lai et al., *Antimicrob. Agents & Chemo.*, 37:1614 (1993), bacteriophage T4 gp55 protein (Gramm et al., *Bio/Technology*, 12:1017 (1994), bacterial ketosteroid isomerase protein (Kuliopulos et al., *J. Am. Chem. Soc.* 116:4599 (1994), ubiquitin (Pilon et al., *Biotechnol. Prog.* 13:374-79 (1997), bovine prochymosin (Naught et al., *Biotechnol. Bioengin.* 57:55-61 (1998), and bactericidal/permeability-increasing protein ("BPI"; U.S. Pat. No. 6,242,219 to Better et al.). The art is replete with specific examples of this technology, see for example U.S. Pat. No. 6,613,548, describing fusion protein of proteinaceous tag and a soluble protein and subsequent purification from cell lysate; U.S. Pat. No. 6,037,145, teaching a tag that protects the expressed chimeric protein from a specific protease; U.S. Pat. No. 5,648,244, teaching the synthesis of a fusion protein having a tag and a cleavable linker for facile purification of the desired protein; and U.S. Pat. Nos. 5,215, 896; 5,302,526; 5,330,902; and 7,501,484, describing fusion tags containing amino acid compositions specifically designed to increase insolubility of the chimeric protein or peptide.

Shorter inclusion body tags have been developed from the *Zea mays* zein protein (U.S. Pat. No. 7,732,569), the *Daucus carota* cystatin (U.S. Pat. No. 7,662,913), an amyloid-like hypothetical protein from *Caenorhabditis elegans* (U.S. Pat. Nos. 7,427,656 and 7,795,382), and a ketosteroid isomerase-derived solubility tag modified to be more acid resistant (U.S. Pat. No. 7,829,311 to DeCarolis et al.). The use of short inclusion body tags increases the yield of the target peptide produced within the recombinant host cell.

U.S. Patent Application Publication No. 2009-0043075A1 to Alsop et al. discloses fusion proteins comprising cross-linkable inclusion body tags. After cleaving the recovered fusion protein, oxidative cross-linking is used to separate the inclusion body tag from the polypeptide of interest.

U.S. Pat. Nos. 7,678,883 and 7,794,979 to Cheng et al. disclose inclusion body tags derived from an 11 amino acid synthetic peptide (i.e. peptide "PII-2"; also known as peptide "DN1") capable of self-assembly into β-sheet tapes, ribbons, fibrils, and fibers in water has been described (Aggeli et al., *J. Amer. Chem. Soc.*, 125:9619-9628 (2003); Aggeli et al., *PNAS*, 98(21):11857-11862 (2001); Aggeli et al., *Nature*, 386:259-262 (1997); and Aggeli et al., *J. Mater Chem*, 7(7): 1135-1145 (1997).

Fusion peptides comprising a solubility tag are typically subjected to a cleavage step to separate the solubility tag from the peptide of interest. Separating the solubility tag from the peptide of interest may be particularly desirable if the presence of the tag adversely impacts the properties of the peptide of interest. However, cleavage of the fusion peptide followed by one or more purification steps adds significant cost to the overall process.

One way to reduce the cost of producing a fusion peptide comprising a solubility tag is to use an inclusion body tag that does not need to be removed during downstream processing. Preferably, the "leave on" solubility tag is capable of providing additional functionality (beyond inclusion body formation) to the peptide of interest. Such multi-functional "leave on" solubility tags would significantly reduce the cost of manufacture and provide a higher value product Small peptides may be used in material science applications based on their ability to bind to a target material. These "target surface-binding peptides" may be used to prepare peptide-based reagents (e.g., peptides of interest) designed to couple or deliver a benefit agent to the target material. Peptide-based reagents have been used to target cosmetic benefit agents to a variety of body surfaces (U.S. Pat. Nos. 7,220,405; 7,309,482; 7,285,264 and 7,807,141; U.S. Patent Application Publication Nos. 2005-0226839 A1; 2007-0196305 A1; 2006-0199206 A1; 2007-0065387 A1; 2008-0107614 A1; 2007-0110686 A1; 2006-0073111 A1; 2010-0158846; 2010-0158847; and 2010-0247589; and published PCT applications WO2008/054746; WO2004/048399; and WO2008/073368).

The problem to be solved is to provide a solubility tag that is (1) effective in preparing fusion proteins which accumulate in an insoluble form within the host cell (i.e., forming inclusion bodies), and (2) does not need to be cleaved from the fusion proteins prior to the intended use (i.e., the presence of the solubility tag in the fusion peptide/protein does not adversely impact the desired functionality of the polypeptide/protein of interest). In a preferred embodiment of the problem to be solved, the solubility tag is not removed and also provides an additional beneficial property (in addition to driving the formation of inclusion bodies) to the fusion peptide comprising a peptide of interest. Preferably the additional or enhanced property is the ability to control and/or enhance deposition and/or the binding properties of the fusion peptide for the desired target surface.

SUMMARY OF THE INVENTION

Methods and compositions are provided comprising a fusion peptide having a peptide of interest (POI) coupled to at least one multi-functional peptide solubility tag ("multi-functional inclusion body tag") that when present in the fusion protein (1) promotes inclusion body formation within the host cell, and (2) provides an additional functionality to the fusion protein comprising the peptide of interest. As such, the present multi-functional includion body tags are not removed from the fusion peptide. In one aspect, the additional functionality provided by the "leave-on tag" is a controllable and reversible solubility enabling easier downstream processing, a binding functionality for a target material, or a combination of both. In a preferred aspect, the additional functionality of the leave-on tag is a binding affinity for a first target material while the peptide of interest provide a binding functionality for a second target material, wherein the first and second target materials are not the same.

In one embodiment, a method is provided comprising:

a) providing a microbial host cell comprising a heterologous nucleic acid molecule encoding an insoluble fusion peptide comprising at least one first portion and at least one second portion, wherein said first portion comprises a multi-functional solubility tag and said second portion comprises a peptide of interest; wherein the multi-functional solubility tag has the general formula of:
  i) SEQ ID NO: 1-Spacer-[[SEQ ID NO: 1]-[Spacer]$_m$]$_n$ or
  ii) SEQ ID NO: 2-Spacer-[[SEQ ID NO: 2]-[Spacer]$_m$]$_n$
  wherein
  SEQ ID NO: 1 is Xaa1-Gln-[Xaa2]$_p$-[Phe-Xaa3-Xaa4-Xaa5]$_s$-Phe-Xaa6-[Xaa7]$_q$-[Gln]$_r$;

and
SEQ ID NO: 2 is

Xaa1-Gln-Xaa8-[Xaa4--Xaa8]$_s$-Phe-[Glu-Gln-Gln]$_r$;

wherein
Xaa1=Gln or His
Xaa2=Gln, Arg, His, or Lys;
Xaa3=Gln, His, Lys, Arg, or Glu;
Xaa4=Trp or Phe
Xaa5=Gln, His, Lys, Arg or Glu;
Xaa6=Glu, Gln, or Arg;
Xaa7=Gln or Lys;
Xaa8=Asp, Glu, Gln, His, Lys, or Arg;
p, q, and r are independently 0 or 1;
s is an integer ranging from 1 to 5;
n is an integer ranging from 1 to 10;
m=n−1; and
Spacer=a peptide linker ranging from 1 to 100 amino acids in length.

b) growing the microbial host cell under conditions whereby the insoluble fusion peptide is produced within the microbial host cell in the form of at least one inclusion body;

c) recovering the insoluble fusion peptide from the microbial host cell;

d) subjecting the insoluble fusion peptide to an aqueous medium having a first set of conditions whereby the insoluble fusion peptide becomes a soluble fusion peptide; and e) contacting the soluble fusion peptide with a first target material having a surface whereby the fusion peptide non-covalently associates with the surface of the first target material; wherein the association between the fusion peptide and the first target material is dependent upon, or enhanced by, the presence of the multi-functional solubility tag.

In another embodiment, the present method(s) comprise a multi-functional inclusion body tag selected from the group consisting of SEQ ID NOs: IBT187.1 (SEQ ID NO: 4), IBT139 (SEQ ID NO: 14), IBT201 (SEQ ID NO: 15), IBT202 (SEQ ID NO: 16), IBT203 (SEQ ID NO: 17), IBT204 (SEQ ID NO: 18), IBT205 (SEQ ID NO: 19), IBT206 (SEQ ID NO: 20), IBT207 (SEQ ID NO: 21), IBT208 (SEQ ID NO: 22), IBT209 (SEQ ID NO: 23), IBT210 (SEQ ID NO: 24), IBT212

(SEQ ID NO: 25), IBT214 (SEQ ID NO: 26), IBT216 (SEQ ID NO: 27), IBT218 (SEQ ID NO: 28), IBT220 (SEQ ID NO: 29), IBT222 (SEQ ID NO: 30), IBT223 (SEQ ID NO: 31), IBT224 (SEQ ID NO: 32), IBT225 (SEQ ID NO: 33), IBT229 (SEQ ID NO: 34), IBT230 (SEQ ID NO: 35), IBT232 (SEQ ID NO: 36), IBT233 (SEQ ID NO: 37), IBT239 (SEQ ID NO: 38), IBT241 (SEQ ID NO: 39), IBT242 (SEQ ID NO: 40), IBT247 (SEQ ID NO: 41), IBT248 (SEQ ID NO: 42), IBT249 (SEQ ID NO: 43), IBT254 (SEQ ID NO: 44), IBT255 (SEQ ID NO: 45), IBT258 (SEQ ID NO: 46), IBT259 (SEQ ID NO: 47), IBT260 (SEQ ID NO: 48), IBT261 (SEQ ID NO: 49), IBT262 (SEQ ID NO: 50, IBT263 (SEQ ID NO: 51), IBT282 (SEQ ID NO: 52), IBT283 (SEQ ID NO: 53), IBT284 (SEQ ID NO: 54), IBT287 (SEQ ID NO: 55), IBT289 (SEQ ID NO: 56), IBT290 (SEQ ID NO: 57), IBT294 (SEQ ID NO: 58), IBT295 (SEQ ID NO: 59), IBT297 (SEQ ID NO: 60), IBT298 (SEQ ID NO: 61), IBT299 (SEQ ID NO: 62), IBT310 (SEQ ID NO: 63), IBT311 (SEQ ID NO: 64), IBT312 (SEQ ID NO: 65), IBT313 (SEQ ID NO: 66), IBT314 (SEQ ID NO: 67), IBT315 (SEQ ID NO: 68), IBT316 (SEQ ID NO: 69), IBT317 (SEQ ID NO: 70), IBT320 (SEQ ID NO: 71), IBT321 (SEQ ID NO: 72), IBT326 (SEQ ID NO: 73), IBT327 (SEQ ID NO: 74), IBT332 (SEQ ID NO: 75), IBT334 (SEQ ID NO: 76), and IBT340 (SEQ ID NO: 77).

In another embodiment, a multi-function solubility tag is provided selected from the group consisting of: IBT205 (SEQ ID NO: 19), IBT206 (SEQ ID NO: 20), IBT207 (SEQ ID NO: 21), IBT208 (SEQ ID NO: 22), IBT209 (SEQ ID NO: 23), IBT210 (SEQ ID NO: 24), IBT212 (SEQ ID NO: 25), IBT214 (SEQ ID NO: 26), IBT216 (SEQ ID NO: 27), IBT218 (SEQ ID NO: 28), IBT220 (SEQ ID NO: 29), IBT222 (SEQ ID NO: 30), IBT233 (SEQ ID NO: 37), IBT242 (SEQ ID NO: 40), IBT248 (SEQ ID NO: 42), IBT249 (SEQ ID NO: 43), IBT254 (SEQ ID NO: 44), IBT255 (SEQ ID NO: 45), IBT258 (SEQ ID NO: 46), IBT259 (SEQ ID NO: 47), IBT261 (SEQ ID NO: 49), IBT262 (SEQ ID NO: 50, IBT263 (SEQ ID NO: 51), IBT299 (SEQ ID NO: 62), IBT310 (SEQ ID NO: 63), IBT311 (SEQ ID NO: 64), IBT312 (SEQ ID NO: 65), IBT313 (SEQ ID NO: 66), IBT314 (SEQ ID NO: 67), IBT315 (SEQ ID NO: 68), IBT316 (SEQ ID NO: 69), IBT317 (SEQ ID NO: 70), IBT320 (SEQ ID NO: 71), IBT321 (SEQ ID NO: 72), IBT326 (SEQ ID NO: 73), IBT327 (SEQ ID NO: 74), IBT332 (SEQ ID NO: 75), IBT334 (SEQ ID NO: 76), and IBT340 (SEQ ID NO: 77).

In another embodiment, a multi-functional inclusion body tag is provided comprising at least one core motif having an amino acid sequence selected form the group consisting of SEQ ID NOs: 80, 85, 86, 87, 88, 91, 92, 93, 94, 95, 96, 97, 98, 100, and 101.

Fusion peptides comprising the present multi-functional solubility tags and/or core motifs may be incorporated into various compositions. As such, a composition is also provided comprising a fusion peptide comprising at least one multi-functional solubility tag as defined above.

In another embodiment, a composition comprising a particle comprising the at least one of the present fusion peptides is also provided. In a preferred embodiment, the particle comprises an average particle size of 100 nm to 10 μm as measured by a light scattering method. In a further aspect, the particle is partially or completely coated with one or more of the present fusion peptides.

In another embodiment, a personal care product is provided comprising a fusion peptide comprising at least one multi-functional solubility tag as defined above.

In another embodiment, the personal care product is selected from the group consisting of a shampoos, hair gels, hair sprays, mousses, hair coloring products, hair bleaching products, hair conditioners, body washes, skin creams, lotions, skin moisturizer, sunscreens, tonics, toothpastes, dental creams, tooth gels, tooth powders, mouth washes, breath fresheners, and dental floss.

In another embodiment, the multi-functional inclusion body tag (IBT) has affinity for a first target material while the peptide of interest (POI) has affinity for a second target material, wherein the first and second target materials are not the same. As such, the fusion peptide acts as an interfacial peptide bridge coupling the first target material to a second target material. The target material(s) may vary and may include in certain embodiments films, particles, and coated particles. In one embodiment, the target material is a pigment (such as lakes, insoluble organic pigment, insoluble inorganic pigment), a body tissue, a cell surface receptor, a body tissue suitable for cosmetic personal care products (e.g., hair, skin, nail, teeth and other oral cavity tissues), a body tissue for medical or veterinary applications, a plant tissue (e.g., seeds, leaves, stems, flowers, fruit, etc.), a polymer (such as polystyrene, polyethylene, polypropylene, polytetrafluoroethylene, polyester, polyvinyl chloride, poly methyl methacrylate, polyethersulfone, polyimide, polyamide, aramids (e.g., poly para-phenylene terephthalamide ("KEVLAR®") and poly meta-phenylene terephthalamide ("NOMEX®")), poly urethanes, and polysaccharides (e.g. cellulose, cellulosic materials, starch, chitin)), minerals (e.g. silica, silicates, micas, titanium dioxide, alumina, iron oxides, clays), and metals (e.g., gold, silver), carbon surfaces such as carbon black, graphite and carbon nanotubes, to name a few.

In another embodiment, an affinity media is provided comprising a fusion peptide having at least one multi-functional solubilty tag as defined above. In a further aspect, the affinity media comprises a solid support comprising a material selected from the group consisting of a pigment, a plant tissue, a polymer, polystyrene, polyethylene, polypropylene, polytetrafluoroethylene, polyester, polyvinyl chloride, poly (methyl methacrylate), polyethersulfone, polyimide, polyamide, aramids, poly para-phenylene terephthalamide, poly meta-phenylene terephthalamide, poly urethane, polysaccharides, cellulose, starch, chitin, minerals, silica, silicates, micas, titanium dioxide, alumina, iron oxides, clays, metals, gold, silver, carbon, carbon black, graphite and carbon nanotubes. In a further aspect, the solid support is in the form of a resin, a membrane, a filter, a bead, a fiber, a foam, a film or any combination thereof.

The affinity media comprising at least one of the present fusion peptides may be used in a method to obtain a material from an aqueous matrix. As such, a method is provided comprising:

a) providing an aqueous matrix comprising a target material to be obtained from the aqueous matrix; and b) contacting the aqueous matrix with the affinity media described above whereby the target material binds to the fusion protein. In a preferred aspect, the above method further comprises step (c), eluting the bound target material from the affinity media.

In another embodiment, a biomedical or tissue engineering composition comprising one or more of the present fusion peptides or a composition comprising a particle comprising one or the present fusion peptides is also provided. In one embodiment, the portion of the fusion peptide comprising the multi-functional inclusion body tag is capable of forming a hydrogel and the second portion of the fusion peptide has affinity for a body tissue and/or a cell surface receptor. In a further embodiment, the second portion having affinity for the cell surface receptor comprises at least one RGD peptide.

BRIEF DESCRIPTION OF THE BIOLOGICAL SEQUENCES

Figure 1:
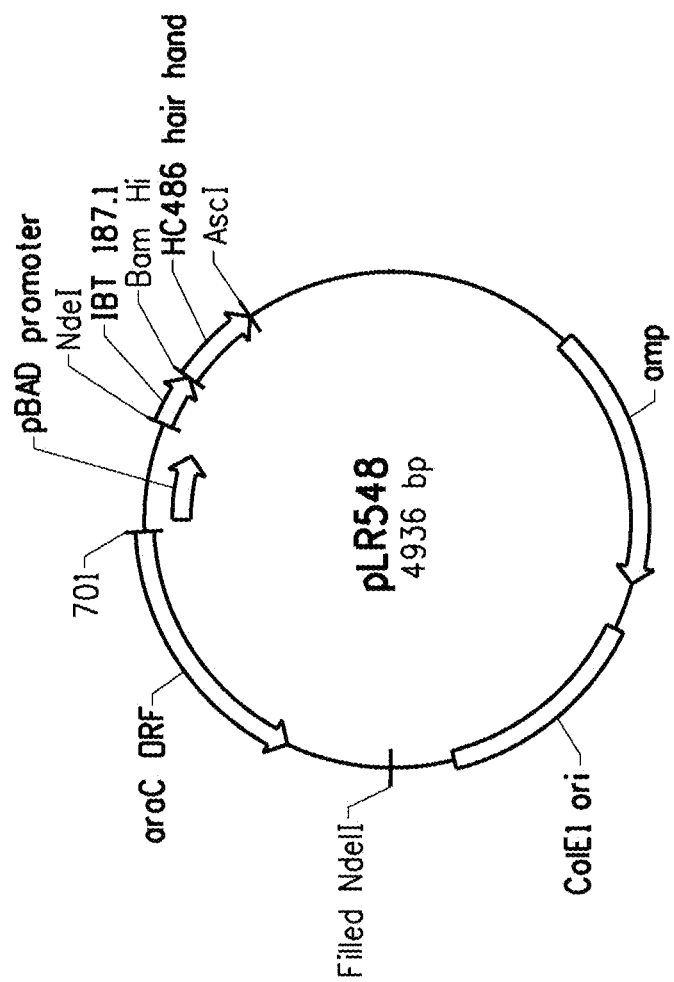
FIG. 1 is the map of plasmid pLR548 (Example 1, SEQ ID NO: 78)

The following sequences comply with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST. 25 (1998) and the sequence listing requirements of the EPC and PCT (Rules 5.2 and 49.5 (a bis), and Section 208 and Annex C of the Administrative Instructions). The symbols and format used for nucleotide and amino acid sequence data comply with the rules set forth in 37 C.F.R. §1.822.

SEQ ID NO: 1 is the amino acid sequence a structural formula for multi-functional inclusion body tags.

SEQ ID NO: 2 is the amino acid sequence a structural formula for multi-functional inclusion body tags.

SEQ ID NO: 3 is the nucleic acid sequence of a polynucleotide encoding IBT187.1.

SEQ ID NO: 4 is the amino acid sequence of IBT187.1.

SEQ ID NO: 5 is the nucleic acid sequence encoding the peptide of interest HC263.

SEQ ID NO: 6 is the amino acid sequence of the peptide of interest HC263.

SEQ ID NO: 7 is the nucleic acid sequence encoding fusion peptide IBT187.HC263.

SEQ ID NO: 8 is the amino acid sequence of fusion peptide IBT187.HC263.

SEQ ID NO: 9 is the nucleic acid sequence encoding fusion peptide IBT187.H2-TonB.G3.

SEQ ID NO: 10 is the amino acid sequence of fusion peptide IBT187.H2-TonB.G3.

SEQ ID NO: 11 is the nucleic acid sequence of a polynucleotide encoding IBT233.

SEQ ID NO: 12 is the nucleic acid sequence encoding fusion peptide IBT233.HC263.

SEQ ID NO: 13 is the amino acid sequence of fusion peptide IBT233.HC263.

SEQ ID NO: 14 is the amino acid sequence of IBT139.
SEQ ID NO: 15 is the amino acid sequence of IBT201.
SEQ ID NO: 16 is the amino acid sequence of IBT202.
SEQ ID NO: 17 is the amino acid sequence of IBT203.
SEQ ID NO: 18 is the amino acid sequence of IBT204.
SEQ ID NO: 19 is the amino acid sequence of IBT205.
SEQ ID NO: 20 is the amino acid sequence of IBT206.
SEQ ID NO: 21 is the amino acid sequence of IBT207.
SEQ ID NO: 22 is the amino acid sequence of IBT208.
SEQ ID NO: 23 is the amino acid sequence of IBT209.
SEQ ID NO: 24 is the amino acid sequence of IBT210.
SEQ ID NO: 25 is the amino acid sequence of IBT212.
SEQ ID NO: 26 is the amino acid sequence of IBT214.
SEQ ID NO: 27 is the amino acid sequence of IBT216.
SEQ ID NO: 28 is the amino acid sequence of IBT218.
SEQ ID NO: 29 is the amino acid sequence of IBT220.
SEQ ID NO: 30 is the amino acid sequence of IBT222.
SEQ ID NO: 31 is the amino acid sequence of IBT223.
SEQ ID NO: 32 is the amino acid sequence of IBT224.
SEQ ID NO: 33 is the amino acid sequence of IBT225.
SEQ ID NO: 34 is the amino acid sequence of IBT229.
SEQ ID NO: 35 is the amino acid sequence of IBT230.
SEQ ID NO: 36 is the amino acid sequence of IBT232.
SEQ ID NO: 37 is the amino acid sequence of IBT233.
SEQ ID NO: 38 is the amino acid sequence of IBT239.
SEQ ID NO: 39 is the amino acid sequence of IBT241.
SEQ ID NO: 40 is the amino acid sequence of IBT242.
SEQ ID NO: 41 is the amino acid sequence of IBT247.
SEQ ID NO: 42 is the amino acid sequence of IBT248.
SEQ ID NO: 43 is the amino acid sequence of IBT249.
SEQ ID NO: 44 is the amino acid sequence of IBT254.
SEQ ID NO: 45 is the amino acid sequence of IBT255.
SEQ ID NO: 46 is the amino acid sequence of IBT258.
SEQ ID NO: 47 is the amino acid sequence of IBT259.
SEQ ID NO: 48 is the amino acid sequence of IBT260.
SEQ ID NO: 49 is the amino acid sequence of IBT261.
SEQ ID NO: 50 is the amino acid sequence of IBT262.
SEQ ID NO: 51 is the amino acid sequence of IBT263.
SEQ ID NO: 52 is the amino acid sequence of IBT282.
SEQ ID NO: 53 is the amino acid sequence of IBT283.
SEQ ID NO: 54 is the amino acid sequence of IBT284.
SEQ ID NO: 55 is the amino acid sequence of IBT287.
SEQ ID NO: 56 is the amino acid sequence of IBT289.
SEQ ID NO: 57 is the amino acid sequence of IBT290.
SEQ ID NO: 58 is the amino acid sequence of IBT294.
SEQ ID NO: 59 is the amino acid sequence of IBT295.
SEQ ID NO: 60 is the amino acid sequence of IBT297.
SEQ ID NO: 61 is the amino acid sequence of IBT298.
SEQ ID NO: 62 is the amino acid sequence of IBT299.
SEQ ID NO: 63 is the amino acid sequence of IBT310.
SEQ ID NO: 64 is the amino acid sequence of IBT311.
SEQ ID NO: 65 is the amino acid sequence of IBT312.
SEQ ID NO: 66 is the amino acid sequence of IBT313.
SEQ ID NO: 67 is the amino acid sequence of IBT314.
SEQ ID NO: 68 is the amino acid sequence of IBT315.
SEQ ID NO: 69 is the amino acid sequence of IBT316.
SEQ ID NO: 70 is the amino acid sequence of IBT317.
SEQ ID NO: 71 is the amino acid sequence of IBT320.
SEQ ID NO: 72 is the amino acid sequence of IBT321.
SEQ ID NO: 73 is the amino acid sequence of IBT326.
SEQ ID NO: 74 is the amino acid sequence of IBT327.
SEQ ID NO: 75 is the amino acid sequence of IBT332.
SEQ ID NO: 76 is the amino acid sequence of IBT334.
SEQ ID NO: 77 is the amino acid sequence of IBT340.
SEQ ID NO: 78 is the nucleic acid sequence of plasmid pLR548.
SEQ ID NO: 79 is the nucleic acid sequence of plasmid pLD001.233.
SEQ ID NOs: 80-104 are the amino acid sequences of core motifs found in at least one of the multi-functional inclusion body tags.

SEQ ID NOs: 105-392 are the amino acid sequences of exemplary peptides that to bind at least one body surface including hair (SEQ ID NOs: 105-231), skin (SEQ ID NOs: 227-279), nail (SEQ ID NOs: 280-281), and tooth (SEQ ID NOs: 282-392).

SEQ ID NOs: 393-421 are the amino acid sequences of exemplary antimicrobial peptides.

SEQ ID NOs: 422-446 are the amino acid sequences of exemplary pigment binding peptides.

SEQ ID NOs: 447-452 are exemplary cellulose-binding peptides.

SEQ ID NOs: 453-479 are the amino acid sequences of exemplary polymer binding peptides. Specifically, SEQ ID NO: 453 binds to poly(ethylene terephthalate), SEQ ID NOs: 454-464 bind to poly(methyl methacrylate), SEQ ID NOs: 465-470 bind to Nylon, and SEQ ID NOs: 471-479 bind to poly(tetrafluoroethylene).

SEQ ID NOs: 480-495 are the amino acid sequences of exemplary clay binding peptides.

SEQ ID NO: 496 is the amino acid sequence of "AuBD", a peptide having affinity for gold.

SEQ ID NO: 497 is the amino acid sequence of fusion peptide IBT255.AuBD.

SEQ ID NO: 498 is the amino acid sequence of synthetic peptide HC353 (U.S. Patent Application Publication No. 2010-0158837; hereby incorporated by reference).

SEQ ID NO: 499 is the amino acid sequence of fusion peptide IBT255.HC263.

DETAILED DESCRIPTION OF THE INVENTION

Compositions and methods directed to the use of a multi-functional solubility tag as a component of fusion peptide/protein are provided herein, wherein the presence of the multi-functional solubility tag in the fusion peptide facilitates:

(i) producing the fusion peptide in an insoluble form (i.e., induces inclusion body formation) within a recombinant host cell;

(ii) controlling fusion peptide solubility (once recovered from the recombinant host cell) upon modulation of physiochemical conditions;

(iii) providing new or enhanced surface active properties; and (iv) increasing the overall efficiency of production.

The presence of the solubility tag in a fusion peptide provides additional beneficial functionality beyond inclusion body formation. As such, the present multi-functional solubility tags are not removed ("leave-on" peptide tags; "LOTs") from the fusion peptide and remain part of the desired peptidic fusion product.

In one embodiment, the methods and present compositions are useful for the recombinant expression and recovery of any bioactive peptides and proteins. Such peptides/proteins typically have high value in any number of applications including, but not limited to, medical, biomedical, diagnostic, personal care, and affinity applications where the peptides of interest are used as linkers to various surfaces.

In this disclosure, a number of terms and abbreviations are used. The following definitions apply unless specifically stated otherwise. Unless otherwise noted, all U.S. Patents and U.S. Patent Applications referenced herein are incorporated by reference in their entirety.

As used herein, the articles "a", "an", and "the" preceding an element or component of the invention are intended to be nonrestrictive regarding the number of instances (i.e., occurrences) of the element or component. Therefore "a", "an" and "the" should be read to include one or at least one, and the singular word form of the element or component also includes the plural unless the number is obviously meant to be singular.

The term "comprising" means the presence of the stated features, integers, steps, or components as referred to in the claims, but does not preclude the presence or addition of one or more other features, integers, steps, components or groups thereof. The term "comprising" is intended to include embodiments encompassed by the terms "consisting essentially of" and "consisting of". Similarly, the term "consisting essentially of" is intended to include embodiments encompassed by the term "consisting of".

As used herein, the term "about" modifying the quantity of an ingredient or reactant employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

Where present, all ranges are inclusive and combinable. For example, when a range of "1 to 5" is recited, the recited range should be construed as including ranges "1 to 4", "1 to 3", "1-2", "1-2 & 4-5", "1-3 & 5", and the like.

As used herein, an "inclusion body" is an intracellular deposit comprising aggregated protein found in the cytoplasm of a cell. A peptide of interest that is typically soluble under the normal physiological conditions within the host cell and/or cell lysates can be fused to one or more of the multi-functional inclusion body tags to facilitate formation of an insoluble fusion protein. In another embodiment, the peptide of interest may be partially insoluble in the host cell, but produced at relatively lows levels where significant inclusion body formation does not occur. As such, the formation of inclusion bodies will increase peptide production. In a further embodiment, fusion of the peptide of interest to one or more multi-functional inclusion body tags increases the amount of protein produced in the host cell. Formation of the inclusion body facilitates simple and efficient purification of the fusion peptide from the cell lysate using techniques well known in the art such as centrifugation and filtration.

As used herein, the terms "inclusion body tag" and "solubility tag" will be abbreviated "IBT" and will refer a peptide/polypeptide that facilitates formation of inclusion bodies when fused to a peptide of interest. The peptide of interest is typically soluble within the host cell and/or host cell lysate when not fused to an inclusion body tag. Fusion of the peptide of interest to the inclusion body tag produces a fusion protein that agglomerates into intracellular bodies (inclusion bodies) within the host cell.

As used herein, the terms "multi-functional tag", "multi-functional solubility tag", "multi-functional inclusion body tag", "leave-on tag", and "LOT" will refer to an inclusion body tag having at least one beneficial functionality beyond inclusion body formation when present in a fusion peptide. As such, the "leave-on tag" is not removed during downstream processing and becomes part of the desired peptidic fusion product. The functionality beyond inclusion body formation may include, but is not limited to, medical, biomedical, diagnostic, personal care, and affinity applications (where the peptides of interest are used as linkers to various surfaces). In one embodiment, the presence of the multi-functional solubility tag in the fusion protein provides the ability to control solubility of the fusion peptide under different physio-chemical conditions. In another embodiment, the presence of the multi-functional solubility tag in the fusion protein provides new or enhanced surface active properties. For example, the "leave on tag" may provide a binding affinity for a first target material or may enhance the binding properties of the peptide of interest (POI) for a first target material. In another embodiment, the multi-functional IBT has affinity for a first target material while the peptide of interest (POI) portion of the fusion peptide has affinity for a second target material. As such, the fusion peptide may be used as a peptidic bridge to couple a first target material to a second target material, wherein the first and second target materials are compositionally different.

As used herein, the term "spacer" will refer to a peptide within the present inclusion body tags used to separate the core motif sequences (SEQ ID NOs: 1, 2, and 80-101). In one embodiment, the spacer is 1-100 amino acids in length, preferably 3 to 60 amino acids in length, and most preferably 3 to 30 amino acids in length and is comprised of any naturally occurring L-amino acids. In one embodiment, the "spacer" is comprised of one or more L-amino acids selected from the group consisting of proline, glycine, arginine, asparagine, glutamic acid, glutamine, serine, tyrosine, tryptophan, alanine, leucine, isoleucine, threonine, histidine, lysine, aspartic acid, and combinations thereof.

As used herein, the term "peptide of interest" or "POI" is any peptide that provides a defined desired functionality (that by itself is distinct from the functionality of the multi-functional inclusion body tag), such as a binding affinity for a target material, surface or a specific molecule; a biological activity such as a growth factor or an antimicrobial; a physical modification of a surface to provide charge, hydrophobicity, chelation, dispersion, optical properties such as refractive index, color, UV protection or fluorescence or conditioning agent, and the ability to self assemble in macromolecular structures. The peptide of interest may comprise one or more distinct surface binding domains. The peptide of interest is soluble and/or difficult to accumulate within the microbial host cell when not produced in the form of a fusion peptide comprising at least one of the present multi-functional inclusion body tags.

As used herein, the terms "fusion protein", "fusion peptide", "chimeric protein", and "chimeric peptide" will be used interchangeably and will refer to a polymer of amino acids (peptide, oligopeptide, polypeptide, or protein) comprising at least two portions, each portion comprising distinct function(s). The present fusion peptides comprise at least one multi-functional solubility tag and at least one peptide of interest, wherein the presence of the mulit-functional inclusion body tag provides additional functionality (beyond inclusion body formation) to the fusion peptide. Means to prepare peptides synthetically at small scale are well known in the art (see, for example, Stewart et al., *Solid Phase Peptide Synthesis*, Pierce Chemical Co., Rockford, Ill., 1984; Bodanszky, *Principles of Peptide Synthesis*, Springer-Verlag, New York, 1984; and Pennington et al., *Peptide Synthesis Protocols*, Humana Press, Totowa, N.J., 1994). The various components of the fusion peptides (inclusion body tag, peptide of interest, and the optional peptide "spacers") described herein can be combined using carbodiimide coupling agents (see for example, Hermanson, Greg T., *Bioconiuqate Techniques*, Academic Press, New York (1996)), diacid chlorides, diisocyanates and other difunctional coupling reagents that are reactive to terminal amine and/or carboxylic acid groups on the peptides. However, chemical synthesis is often limited to peptides of less than about 50 amino acids length due to cost and/or impurities. In a preferred embodiment, the biological molecules described herein are prepared using standard recombinant DNA and molecular cloning techniques.

As used herein, the term "altering the physio-chemical conditions" will refer to making alterations to the pH, temperature, ionic composition, ionic strength of the aqueous matrix, and any combination thereof that facilitates controlled solubility of the fusion peptide comprising the multi-functional inclusion body tag. Under normal physiological conditions within the recombinant microbial host cell (typically an intracellular pH of about 6.5-about 8.0, preferably about 7.5 to about 8.0 for most neutrophiles) the multi-functional inclusion body tag induces inclusion body formation. The fusion peptide may be subjected to altered physio-chemical conditions (typically after the fusion peptide has been recovered from the host cell) to control the solubility, wherein the presence of the leave-on tag alters the solubility profile of the fusion peptide. The physio-chemical conditions may be altered one or more times to dissolve or precipitate the fusion peptide. In one embodiment, solubilized fusion peptide (in the presence of a target material) may be exposed to physio-chemical conditions that induces or enhances deposition/binding of the fusion peptide to the surface of the target material. Physico-chemical conditions that can be modified to promote the solubility or the insolubility of a fusion peptide (typically once received from the cell) may include pH, medium conductivity, salts, metal ions, polyvalent ions, chaotropes, surfactants, solvents, fusion peptide concentration, rheology modifiers, thickeners and temperature.

As used herein, the term "medium" may mean fermentation medium or a suspension medium. The fermentation medium is the medium which supports the growth of fusion peptide-producing cells. The medium is typically aqueous but may also include a water-oil emulsion. As used herein, the term "aqueous medium" refers to a medium comprising water. The solubility state of the fusion peptides recovered from the host cell is controlled by altering the physio-chemical conditions within an aqueous medium comprising the fusion peptide. Different sets of physio-chemical conditions may used and may be generally separated into three general categories: (1) a set of conditions that promotes solubility, (2) a set of conditions that promotes insolubility, and (3) a set of conditions thay may promote or enhance deposition of the fusion peptide to a target material surface (i.e., the target material is contacted with a medium comprising the fusion peptide).

As used herein, the term "benefit agent" refers to a material that promotes or enhances a useful advantage, a favorable/desirable effect or benefit. The benefit agent may be a fusion peptide or a molecule or a material associated with (or coupled to) a portion of the fusion peptide. Examples of benefits agents may include, but are not limited to conditioners, pigments, dyes, fragrances, whitening agents, bleaching agents, enzymes, pharmaceutical agents (e.g., targeted delivery of cancer treatment agents), diagnostic/labeling agents, ultraviolet light blocking agents (i.e., active agents in sunscreen protectants), affinity media, particles, and antimicrobial agents (e.g., antimicrobial peptides), to name a few.

As used herein, the term "target material" will refer to a material that receives or delivers a beneficial or desired property upon the presence of the fusion peptide. In one embodiment, the fusion peptide has affinity for a target material wherein the binding functionality is dependent upon the presence of the multi-functional inclusion boy tag (IBT), the peptide of interest (POI), or a combination of the IBT and POI. In one embodiment, the presence of the multi-functional IBT enhances the binding affinity of a POI having affinity for a target material. In another embodiment, the multi-functional IBT has affinity for a target surface and the portion of the fusion peptide comprising the peptide of interest is a benefit agent, such as a conditioning agent or antimicrobial agent (e.g., antimicrobial peptide).

The target material(s) may vary and may include in certain embodiments films, particles, and coated particles. In one embodiment, the target material may include a pigment (such as lakes, insoluble organic pigment, insoluble inorganic pigment), a body tissue suitable for cosmetic personal care products (e.g., hair, skin, nail, teeth and other oral cavity tissues), a body tissue for medical or veterinary applications, a plant tissue (e.g., seeds, leaves, stems, flowers, fruit, etc.), a polymer (such as polystyrene, polyethylene, polypropylene, polytetrafluoroethylene, polyester, polyvinyl chloride, poly methyl methacrylate, polyethersulfone, polyimide, polyamide, aramids (e.g., poly para-phenylene terephthalamide ("KEVLAR®") and poly meta-phenylene terephthalamide (NOMEX®)), poly urethanes, and polysaccharides (e.g. cellulose, cellulosic materials, starch, chitin)), minerals (e.g. silica, silicates, micas, titanium dioxide, alumina, iron oxides, clays), and metals (e.g., gold, silver), carbon surfaces such as carbon black, graphite and carbon nanotubes, to name a few.

As used herein, the term "pigment" refers to an insoluble, organic or inorganic colorant.

As used herein, the term "hair" as used herein refers to mammalian hair. In one embodiment, the "hair" is preferably human hair, eyebrows, and eyelashes.

As used herein, the term "skin" as used herein refers to mammalian skin. In one embodiment, the "skin" is preferably human skin, or substitutes for human skin, such as pig skin, VITRO-SKIN® and EPIDERM™.

As used herein, the term "nails" as used herein refers to mammalian nails, such as fingernails, toenails and other keratinaceious nail materials. In one embodiment, the "nails" are preferably human fingernails and/ortoenails.

As used herein, the term "strong affinity" or "high affinity" will refer to a binding affinity having a $K_D$ or $MB_{50}$ value of less than or equal to about $10^{-5}$ M, preferably less than or equal to about $10^{-6}$ M, more preferably less than or equal to about $10^{-7}$ M, more preferably less than or equal to about $10^{-8}$ M, even more preferably less than or equal to about $10^{-9}$ M, or most preferably less than or equal to about $10^{-10}$ M.

As used herein, "$K_D$" corresponds to the concentration of peptide at which the binding site on the target is half occupied, i.e., when the concentration of target with peptide bound (bound target material) equals the concentration of target with no peptide bound. The smaller the dissociation constant, the more tightly the peptide is bound. For example, a peptide with a nanomolar (nM) dissociation constant binds more tightly than a peptide with a micromolar (μM) dissociation constant. Certain embodiments of the invention will have a $K_D$ value of $10^{-5}$ or less.

As used herein, "$MB_{50}$" refers to the concentration of the binding peptide that gives a signal that is 50% of the maximum signal obtained in an ELISA-based binding assay. See, e.g., Example 3 of U.S. Patent Application Publication 2005/022683; hereby incorporated by reference. The $MB_{50}$ provides an indication of the strength of the binding interaction or affinity of the components of the complex. The lower the value of $MB_{50}$, the stronger, i.e., "better," the interaction of the peptide with its corresponding substrate. For example, a peptide with a nanomolar (nM) $MB_{50}$ binds more tightly than a peptide with a micromolar (μM) $MB_{50}$. Certain embodiments of the invention will have a $MB_{50}$ value of $10^{-5}$ M or less.

As used herein, the terms "bind", "binding", and "coupling" are used interchangeably and is meant to convey an association between a fusion peptide and a surface on a target material though a variety of non-covalent interactions, such as ionic bond-based (electrostatic interaction), hydrogen bond-based, hydrophobic bond-based, chelation based, biological specific affinity, a general aggregation or the formation of tertiary or quaternary structures or a combination thereof, but does not include, by proviso, covalent binding.

As used herein, the term "affinity peptide" or "target surface-binding peptide" refers to a peptide having strong affinity for a particular target material or compound. Examples may include, but are not limited to, body surface-binding peptides, pigment-binding peptides, polymer-binding peptides, various mineral-binding peptides, clay-binding peptides, cotton-binding peptides, cellulose-binding peptides, and metal-binding peptides.

As used herein, a "body surface-binding peptide" is an affinity peptide that binds with high affinity to a specified body surface. Examples may include, but are not limited to, hair-binding peptides, skin-binding peptides, nail-binding peptides, and tooth-binding peptides.

As used herein, a "hair-binding peptide" is an affinity peptide that binds with high affinity to hair.

As used herein, a "skin-binding peptide" is an affinity peptide that binds with high affinity to skin.

As used herein, a "nail-binding peptide" is an affinity peptide that binds with high affinity to fingernail or toenail.

As used herein, a "tooth-binding peptide" is an affinity peptide that binds with high affinity to tooth enamel and/or tooth pellicle. In a preferred embodiment, the tooth-binding peptide binds with high affinity to tooth enamel.

As used herein, an "antimicrobial peptide" is a peptide having the ability to kill microbial cell populations (U.S. Pat. No. 7,427,656; hereby incorporated by reference). The amino acid sequences of exemplary antimicrobial peptides are provided as SEQ ID NOs: 393-421.

As used herein, "cellulose-binding peptide" refers to an affinity peptide that binds with high affinity to cellulose. Exemplary cellulose-binding peptides are provided as SEQ ID NOs: 447-452.

As used herein, "clay-binding peptide" refers to a peptide that binds with high affinity to clay. Exemplary clay-binding peptides are provided as SEQ ID NOs: 480-495.

As used herein, "pigment-binding peptide" refers to an affinity peptide that binds with high affinity to a pigment, Examples of pigment-binding peptides are provided as SEQ ID NOs: 422-446.

As used herein, "polymer-binding peptide" refers to an affinity peptide that binds with high affinity to at least one specified polymer. Examples of polymer-binding peptides are provided herein as SEQ ID NOs: 453-479.

As used herein, "metal-binding peptide" refers to an affinity peptide that binds with high affinity to at least one metal. Examples of metal-binding peptides may include, but are not limited to, gold-binding peptides and silver-binding peptides.

As used herein, the term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). In a further embodiment, the definition of "operably linked" may also be extended to describe the products of chimeric genes, such as fusion peptides. As such, "operably linked" will also refer to the linking of a "leave on" multi-functional solubility tag to a peptide of interest (POI) to be produced, recovered and used as such or for an aqueous composition or formulation.

As used herein, the term "bioactive" refers to peptides that cause a biological response and may be used in a variety of applications including, but not limited to curative agents for diseases (e.g., insulin, interferon, interleukins, anti-angiogenic peptides) (U.S. Pat. No. 6,815,426), antimicrobial or toxin.

As used herein, the term "solubility" refers to the amount of a substance that can be dissolved in a unit volume of a liquid under specified conditions. In the present application, the term "solubility" is used to describe the ability of a peptide/fusion peptide to be resuspended in a volume of solubilization medium, e.g. (an aqueous medium such as a buffer medium) used in biochemical applications and may include Tris, saline, MES, and the like. In one embodiment, a peptide may be defined as soluble in a defined medium when it remains in solution after centrifuging the peptide-containing solution for 5 minutes at 15000 rpm (rcf=21130 g) in a standard tabletop microcentrifuge. The POI, when not coupled to the multi-functional inclusion body tag, is soluble within the host cell and/or cell lysate under normal physiological conditions. As used herein, the term "normal physiological conditions within the host cell" may be defined as an aqueous matrix having a pH of about 6.5 to about 8.0 (typical for neutrophiles) at a temperature suitable for growth of the recombinant host cell. One of ordinary skill in the art can easily determine the physiological conditions within the particule host cell used for recombinant production of the present peptides. Fusion of multi-functional inclusion body tag (IBT) to the POI results in the formation of a fusion peptide that is insoluble under normal physiological conditions within the recombinant host cell, resulting in the formation of at least one inclusion body.

The term "amino acid" refers to the basic chemical structural unit of a protein or polypeptide. The following abbreviations are used herein to identify specific amino acids:

| Amino Acid | Three-Letter Abbreviation | One-Letter Abbreviation |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any naturally-occurring amino acid (or as defined by the formulas described herein) | Xaa | X |

As used herein, the term "genetic construct" refers to a series of contiguous nucleic acids useful for modulating the genotype or phenotype of an organism. Examples of genetic constructs include but are not limited to a nucleic acid molecule, and open reading frame, a gene, a plasmid and the like.

As used herein, the terms "host cell" and "recombinant host cell" refer to a microbial cell comprising an expressible heterologous nucleic acid molecule encoding a fusion peptide having at least one of the present multi-functional inclusion body tags.

Expressible Peptides of Interest

The peptide of interest ("POI") targeted for production using the present method is one that is appreciably soluble in the recombinant host cell and/or host cell liquid lysate under normal physiological conditions. In one aspect, the peptides of interest are generally short (<300 amino acids in length) and difficult to recombinantly produce in sufficient amounts due to their solubility and/or exposure to endogenous proteolytic degradation. Fusion of the POI to at least one multi-functional inclusion body tag creates a fusion peptide that is insoluble in the host cell and/or host cell lysate under normal physiological conditions (i.e., inclusion body formation comprising the fusion peptide is observed within the grown host cell). Production of the fusion peptide is typically increased when expressed and accumulated in the form of an insoluble inclusion body as the peptide is generally more protected from endogenous proteolytic degradation. Furthermore, the insoluble fusion peptide can be easily separated from the host cell lysate using a simple separation technique such as centrifugation or filtration. The fusion peptide is not cleaved to remove multi-functional solubility tag that not only facilitates inclusion body formation but also provides surface interactions in downstream applications for forming adducts between two or more surfaces.

In general, the present multi-functional inclusion body tags can be used in a process to produce any peptide of interest that is (1) typically soluble in the cell and/or cell lysate under typical physiological conditions and/or (2) those that can be produced at significantly higher levels when expressed in the form of LOT. In one embodiment, the POI is appreciably soluble in the host cell and/or corresponding cell lysate under normal physiological and/or process conditions.

The length of the POI may vary as long as (1) the POI is appreciably soluble in the host cell and/or cell lysate, and/or (2) the amount of the POI produced is increased when expressed in the form of an insoluble fusion peptide/inclusion body.

The function of the POI is not limited by the present methods and may include, but is not limited to bioactive molecules such as curative agents for diseases (e.g., insulin, interferon, interleukins, peptide hormones, anti-angiogenic peptides, peptide toxins, and peptides (with the proviso that the peptide is not an antibody or an $F_{ab}$ portion of an antibody) that bind to and affect defined cellular targets such as receptors, channels, lipids, cytosolic proteins, and membrane proteins; see U.S. Pat. No. 6,696,089), peptides having an affinity for a particular material such as hair, skin, nail or tooth (see WIPO International Patent Application Publication Nos. WO01/079479, WO04/048399, and WO04/000257; U.S. Patent Application Publication Nos. 2005-0226839, 2010-0247457, and 2010-0247589; U.S. Pat. Nos. 7,736,633; 7,427,656; 7,309,482; 7,749,957; and 7,807,141), cellulose, iron oxides (U.S. Patent Applicatoin Publication No. 2010-0158837), silica (U.S. Patent Application Publication No. 2010-0158822), various polymers (U.S. Pat. Nos. 7,709,601; 7,700,716; 7,906,617; and 7,632,919; and U.S. Patent Application Publication No. 2007-0264720), calcium carbonate (U.S. Pat. No. 7,754,680), and clay binding peptides (U.S. Pat. No. 7,749,957), for targeted delivery of at least one benefit agent.

Examples of various affinity peptides and/or anti-microbial peptides are provided herein as amino acid sequence: SEQ ID NOs: 105-392 are exemplary body surface-binding peptides, SEQ ID NOs: 393-421 are exemplary antimicrobial peptides, SEQ ID NOs: 422-446 are exemplary pigment-binding peptides, SEQ ID NOs: 447-452 are exemplary cellulose-binding peptides, SEQ ID NOs: 453-479 are exemplary polymer-binding peptides, and SEQ ID NOs: 480-495 are exemplary clay binding peptides.

Manipulations of Physio-chemical Conditions to Control Solubility of Fusion Peptides The solubility of the fusion peptides may vary from peptide to peptide. Anyone skilled in the practice of protein chemistry can determine conditions necessary to control solubility by carrying out systematic titrations of independent parameters (pH, salt, ionic strength, fusion peptide concentration, etc.) or by a sampling of conditions involving multiple parameters using a statistical design of experiments (Atkinson, A. C. and Donev, A. N. and Tobias, R. D. (2007) *Optimum Experimental Designs, With SAS*. Oxford University Press, New York, N.Y.). Assays to characterize the physical state of the peptide can include observation for turbidity by eye or with a spectrophotometer at a chosen UV or visible wavelength, sedimentation behavior following centrifugation at a chosen centrifugal force followed by the detection of the peptide in the supernatant or the pellet with a dye assay or polyacrylamide gel electrophoresis, or by dynamic light scattering measurement with an instrument like the Malvern Zetasizer (Malvern Instruments Ltd, England). In all experiments, additional parameters should be taken into consideration such as the speed of the change of state and the effect of the initial peptide concentration.

Fusion Peptides

The multi-functional inclusion body tags are used to create chimeric polypeptides ("fusion peptides") that are insoluble when expressed under the physiological conditions within the host cell, forming inclusion bodies. One of skill in the art will recognize that the elements of the fusion protein can be structured in a variety of ways. The fusion protein will include at least one multi-functional inclusion body tag and at least one peptide of interest (POI). The fusion peptide may include one or more peptide spacers separating the core motif sequences within the multi-functional IBT or may include peptide spacers separating the IBT from the POI. The multi-functional inclusion body tag may be positioned as a leader sequence or a terminator sequence relative to the position of the peptide of interest within the fusion peptide. In another embodiment, a plurality of IBTs and POIs are used when engineering the fusion peptide.

The fusion peptide will typically be insoluble in an aqueous environment at a temperature of 0° C. to 50° C. using a pH range from pH 5 to pH 10, preferably 6 to 10, and most preferably 6 to 8. The temperature, pH, and/or ionic strength of the aqueous environment may be adjusted to obtain the desired solubility characteristics of the fusion peptide/inclusion body.

Method to Make a Peptide of Interest Using Insoluble Fusion Peptides

A genetic construct is prepared encoding a fusion peptide comprising at least one "leave-on" multi-functional inclusion body tag and at least one peptide of interest, wherein the tag(s) and the POI(s) may be separated by optional peptide spacers. Expression of the genetic construct encoding the fusion protein produces an insoluble form of the peptide of interest that accumulates in the form of inclusion bodies within the host cell. The host cell is grown for a period of time sufficient for the insoluble fusion peptide to accumulate within the cell.

The host cell is subsequently lysed using any number of techniques well known in the art. The insoluble fusion peptide/inclusion bodies are then separated from the soluble components of the cell lysate using a simple and economical technique, such as centrifugation and/or filtration.

Transformation and Expression

Construction of genetic cassettes and vectors that may be transformed into an appropriate expression host is common and well known in the art. Typically, the vector or cassette contains sequences directing transcription and translation of the relevant chimeric construct, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Transcription initiation control regions or promoters, which are useful to drive expression of the genetic constructs encoding the fusion peptides in the desired host cell are numerous and familiar to those skilled in the art. Virtually any promoter capable of driving these constructs is suitable for the present invention including, but not limited to CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, ara (pBAD), tet, trp, IPL, IPR, T7, tac, and trc (useful for expression in *Escherichia coli*) as well as the amy, apr, npr promoters and various phage promoters useful for expression in *Bacillus*.

Termination control regions may also be derived from various genes native to the preferred hosts. Optionally, a termination site may be unnecessary; however, it is most preferred if included.

Preferred host cells for expression of the fusion peptides are microbial hosts that can be found broadly within the fungal or bacterial families and which grow over a wide range of temperature, pH values, and solvent tolerances. Because the transcription, translation, and the protein biosynthetic apparatus is the same irrespective of the cellular feedstock, genes are expressed irrespective of the carbon feedstock used to generate the cellular biomass. Large-scale microbial growth and functional gene expression may utilize a wide range of simple or complex carbohydrates, organic acids and alcohols, saturated hydrocarbons such as methane or carbon dioxide in the case of photosynthetic or chemoautotrophic hosts. The functional genes may be regulated, repressed or depressed by specific growth conditions, which may include the form and amount of nitrogen, phosphorous, sulfur, oxygen, carbon or any trace micronutrient including small inorganic ions. In addition, the regulation of functional genes may be achieved by the presence or absence of specific regulatory molecules that are added to the culture and are not typically considered nutrient or energy sources. Growth rate may also be an important regulatory factor in gene expression. Examples of host strains include, but are not limited to fungal or yeast species such as *Aspergillus, Trichoderma, Saccharomyces, Pichia, Yarrowia, Candida, Hansenula*, or bacterial species such as *Salmonella, Bacillus, Acinetobacter, Zymomonas, Agrobacterium, Erythrobacter, Chlorobium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Synechococcus, Anabaena, Thiobacillus, Methanobacterium, Klebsiella*, and *Myxococcus*.

Preferred bacterial host strains include *Escherichia*, *Pseudomonas*, and *Bacillus*. In a highly preferred aspect, the bacterial host strain is *Escherichia coli*.

Fermentation Media

Fermentation media in the present invention must contain suitable carbon substrates. Suitable substrates may include, but are not limited to, monosaccharides such as glucose and fructose, disaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. It is contemplated that the source of carbon utilized may encompass a wide variety of carbon containing substrates and will only be limited by the choice of organism. Although it is contemplated that all of the above mentioned carbon substrates and mixtures thereof are suitable in the present invention, preferred carbon substrates are glucose, fructose, and sucrose.

In addition to an appropriate carbon source, fermentation media must contain suitable minerals, salts, cofactors, buffers and other components, known to those skilled in the art, suitable for the growth of the cultures and promotion of the expression of the fusion peptides.

Culture Conditions

Suitable culture conditions can be selected dependent upon the chosen production host. Typically, cells are grown at a temperature in the range of about 25° C. to about 40° C. in an appropriate medium. Suitable growth media may include common, commercially-prepared media such as Luria Bertani (LB) broth, Sabouraud Dextrose (SD) broth or Yeast medium (YM) broth. Other defined or synthetic growth media may also be used and the appropriate medium for growth of the particular microorganism will be known by one skilled in the art of microbiology or fermentation science. The use of agents known to modulate catabolite repression directly or indirectly, e.g., cyclic adenosine 2': 3'-monophosphate, may also be incorporated into the fermentation medium. Suitable pH ranges for the fermentation are typically between pH 5.0 to pH 9.0, where pH 6.0 to pH 8.0 is preferred. Fermentations may be performed under aerobic or anaerobic conditions where aerobic conditions are generally preferred.

Industrial Batch and Continuous Fermentations

A classical batch fermentation is a closed system where the composition of the medium is set at the beginning of the fermentation and not subject to artificial alterations during the fermentation. Thus, at the beginning of the fermentation the medium is inoculated with the desired organism or organisms, and fermentation is permitted to occur without adding anything to the system. Typically, a "batch" fermentation is batch with respect to the addition of carbon source and attempts are often made at controlling factors such as pH and oxygen concentration. In batch systems the metabolite and biomass compositions of the system change constantly up to the time the fermentation is stopped. Within batch cultures cells moderate through a static lag phase to a high growth log phase and finally to a stationary phase where growth rate is diminished or halted. If untreated, cells in the stationary phase will eventually die. Cells in log phase generally are responsible for the bulk of production of end product or intermediate.

A variation on the standard batch system is the Fed-Batch system. Fed-Batch fermentation processes are also suitable in the present invention and comprise a typical batch system with the exception that the substrate is added in increments as the fermentation progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch fermentations are common and well known in the art and examples may be found in Thomas D. Brock in *Biotechnology: A Textbook of Industrial Microbiology*, Second Edition (1989) Sinauer Associates, Inc., Sunderland, Mass. (hereinafter "Brock"), or Deshpande, Mukund V., *Appl. Biochem. Biotechnol.*, 36:227 (1992).

Although biomass production may be performed in batch mode, it is contemplated that the production method would be adaptable to continuous fermentation methods. Continuous fermentation is an open system where a defined fermentation medium is added continuously to a bioreactor and an equal amount of conditioned media is removed simultaneously for processing. Continuous fermentation generally maintains the cultures at a constant high density where cells are primarily in log phase growth.

Continuous fermentation allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to the medium being drawn off must be balanced against the cell growth rate in the fermentation.

It is contemplated that the present methods may be practiced using either batch, fed-batch or continuous processes and that any known mode of fermentation would be suitable.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

The meaning of abbreviations used is as follows: "min" means minute(s), "h" means hour(s), "µL" means microliter(s), "mL" means milliliter(s), "L" means liter(s), "nm" means nanometer(s), "mm" means millimeter(s), "cm" means centimeter(s), "µm" means micrometer(s), "mM" means millimolar, "M" means molar, "mmol" means millimole(s), "µmol" means micromole(s), "pmol" means picomole(s), "g" means gram(s), "µg" means microgram(s), "mg" means milligram(s), "g" means the gravitation constant, "rpm" means revolutions per minute, "DTT" means dithiothreitol, and "cat#" means catalog number.

General Methods

Standard recombinant DNA and molecular cloning techniques used herein are well known in the art and are described by Sambrook, J. and Russell, D., *Molecular Cloning: A Laboratory Manual*, Third Edition, Cold Spring Harbor Laboratory Press, Cold Spring Harbor, N.Y. (2001); and by Silhavy, T. J., Bennan, M. L. and Enquist, L. W., *Experiments with*

Gene Fusions, Cold Spring Harbor Laboratory Cold Press Spring Harbor, N.Y. (1984); and by Ausubel, F. M. et. al., *Short Protocols in Molecular Biology*, 5$^{th}$ Ed. Current Protocols and John Wiley and Sons, Inc., N.Y., 2002.

Materials and methods suitable for the maintenance and growth of bacterial cultures are also well known in the art. Techniques suitable for use in the following Examples may be found in *Manual of Methods for General Bacteriology*, Phillipp Gerhardt, R. G. E. Murray, Ralph N. Costilow, Eugene W. Nester, Willis A. Wood, Noel R. Krieg and G. Briggs Phillips, eds., American Society for Microbiology, Washington, D.C., 1994, or in Brock (supra). All reagents, restriction enzymes and materials used for the growth and maintenance of bacterial cells were obtained from BD Diagnostic Systems (Sparks, Md.), Invitrogen (Carlsbad, Calif.), Life Technologies (Rockville, Md.), QIAGEN (Valencia, Calif.) or Sigma-Aldrich Chemical Company (St. Louis, Mo.), unless otherwise specified.

Example 1

Expression Plasmid Constructs

The purpose of this example is to describe a generic construction of a plasmid encoding for the expression of a LOT peptide.

The region downstream of the promoter in each of the vectors was designed to facilitate and simplify swapping of the DNA constructs encoding multi-functional solubility tags (alone or in combination with the peptide of interest (POI). In general, the nucleic acid molecules were designed to include the appropriate NdeI/BamHIH (for region encoding the multi-functional solubility tags) and BamHI/AscI restriction sites (for region encoding POI) to facilitate insertion in the expression vector. More specific description of the construction of the various constructs is given below.
Construction of pLR557, the Expression Plasmid Encoding a Fusion Peptide Comprising the Multi-Functional Solubility Tag IBT187 Coupled to the Peptide of Interest HC263 (IBT187.HC263).

Plasmid pLR557 was derived from the commercially available plasmid pBAD-HisA (Invitrogen). pLR557 harbors the gene for the araC regulator. araC is critical for arabinose promoter function. Additionally the plasmid pLR557 comprises a ColE1 type origin of replication, a bla gene to confer ampicillin resistance and aadA-1 gene to confer spectinomycin (Spec) resistance.

To construct pLR557, a modified multiple cloning site (MCS) was cloned in pBAD-HisA. An NdeI restriction site at position 2844 was eliminated to create a single NdeI site downstream of the pBAD promoter and the resulting plasmid was named pBAD-HisA_MCSmod. The NdeI/EcoRI fragment of plasmid pKSIC4-HC77623 (U.S. Pat. No. 7,285,264) was inserted into the NdeI/EcoRI site of pBAD-HisA_MCSmod, generating plasmid pSF004_pBAD-KSIC4-HC77623. The HindIII fragment of plasmid pCL1920 (Lerner and Inouye, Nucleic Acids Research, 18:4631 (1990); GEN-BANK® Accession No. AB236930) comprising the spectinomycin resistance gene (aadA-1) was inserted into pSF004_pBAD-KSI4-HC77623, creating plasmid pLR042. Plasmid pLR557 was created from plasmid pLR042 by removing the coding region for the KSIC4-HC77623 fusion peptide and inserting the coding region (SEQ ID NO: 7) for fusion peptide IBT187-HC263 (SEQ ID NO: 8) comprising the multi-functional solubility tag IBT187 linked in tandem to the peptide of interest (POI) HC263.

Construction of pLR642, the Expression Plasmid Encoding a Fusion Peptide Comprising Solubility Tag IBT233 Coupled to the Peptide of Interest HC263 (IBT233.HC263)

pLR642 was derived from plasmid pLR042 by removing the coding region for the KSIC4-HC77623 fusion peptide and inserting the coding region (SEQ ID NO: 12) for fusion peptide IBT233.HC263 (SEQ ID NO: 13). Many additional plasmids encoding variant IBTs were constructed using similar strategy.
Construction of pLR562, the Expression Plasmid for IBT187.H2-TonB-G3 pLR562 was derived from plasmid pLR042 by removing the coding region for the KSIC4-HC77623 fusion peptide and inserting the coding region (SEQ ID NO: 9) for a multi-functional solubility tag 187 linked to the polypeptide H2-TonB-G3 (i.e., IBT187.H2-TonB-G3; SEQ ID NO: 10).
Construction of pLR565, the Expression Plasmid for LOT Comprising IBT (IBT187.1)

The plasmid pLR565 was constructed to drive the expression of the gene IBT187.1 (SEQ ID NO: 3) in *E. coli* KK2000 for the production of multi-functional peptide tag IBT187.1 (SEQ ID NO: 4). pLR565 was derived from pLR548 by introducing a stop codon after the IBT 187.1 coding sequence. pLR548 is a derivative of the pBAD expression vector (See FIG. 1 for a map of pLR548, SEQ ID NO: 78).
Construction of pLD001-233, the Expression Plasmid for IBT233

Figure 2:
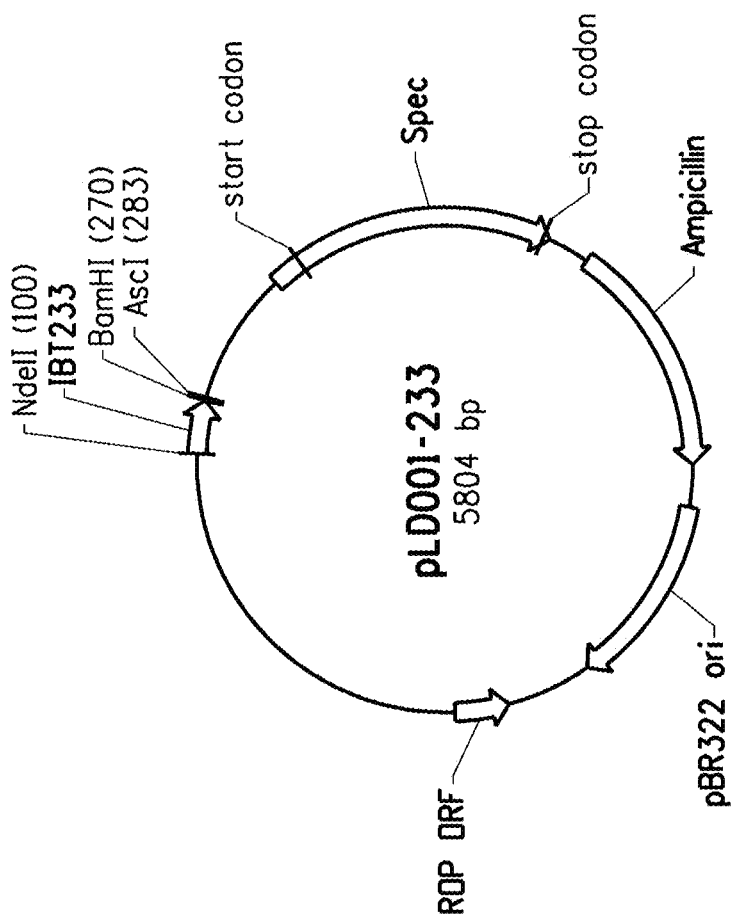
FIG. 2 is the map of plasmid pLD001-233 (Example 1, SEQ ID NO: 79)

The plasmid pLD001-233 was used to drive the expression of a polynucleotide encoding IBT233 (SEQ ID: 11) in *E. coli* BL21-AI (Invitrogen) for the production of the multi-functional inclusion body tag IBT233 (SEQ ID NO: 37). pLD001-233 is a derivative of the T7 expression vector. (See FIG. 2 for a map of pLD001-233, SEQ ID NO: 79).

Example 2

Accumulation of the Multi-functional Solubility Tags as Inclusion Bodies

The purpose of this example is to describe the production of a peptide (a multi-functional solubility tag) in a bacterial host by its accumulation as insoluble inclusion bodies.

Strain KK2000 is a derivative of *E. coli* MG1655 (ATCC 46076™) strain wherein the endogenous chromosomal copy of the araBAD operon has been deleted. The expression plasmids pLR565, pLR557, pLR642 and pLR562 described in Example 1 were individually transformed into the *E. coli* strain KK2000. Plasmid pLD001-233, containing a T7 promoter that drives expression of the gene of interest, was transformed into *E. coli* BL21-AI (Invitrogen). Approximately 30 μL of overnight cultures of individual *E. coli* transformants (both KK2000 and BL21-AI) were inoculated in 3 mL of LB medium (plus 100 μg/mL of ampicillin). The culture was grown to an OD$_{600}$ of about 0.4 and the recombinant proteins were produced by the addition of 0.2% arabinose and grown for 3 hours. To determine soluble versus insoluble cell content, the cells were lysed with CelLytic Express (a mixture of non-denaturing detergents and enzymes available from Sigma, St. Louis, USA) and soluble and insoluble fractions were analyzed on an SDS-PAGE gel. The multi-functional solubility tags IBT187.1 and IBT233 were each produced in the form of insoluble inclusion bodies.

In a similar fashion, plasmids pLR557, pLR642, and pLR562 were used to recombinantly produce insoluble fusion peptides IBT187.HC263 (SEQ ID NO: 8), IBT233.HC263 (SEQ ID NO: 13) and IBT187.H2-TonB-G3 (SEQ ID NO: 10), respectively.

Example 3

Production and Purification of Inclusion Bodies Produced from IBT187.1, IBT233, IBT187.HC263, IBT233.HC263, and IBT187.H2-TonB-G3

The purpose of this example is to describe a general process for the production and recovery of the insoluble peptides from the fermentation of the microbial host to the recovery and purification of the inclusion bodies.

The cells containing the two different inclusion body tags and three different fusion peptide constructs were each grown at 37° C. for 2 hr in 1 liter autoinduction media ($Na_2HPO_4$, 7.1 g; $KH_2PO_4$, 6.8 g; $(NH_4)_2SO_4$, 3.3 g; $MgSO_4$, 0.36 g; Tryptone, 9.2 g; Yeast Extract, 4.6 g; NaCl, 4.6 g; glycerol, 7.5 g; D-glucose, 0.75 g; and L-arabinose, 0.5 g).

The cells were harvested by centrifugation and lysed in 200 mL lysis buffer (50 mM Tris pH 7.5, 10 mM EDTA, 50 mg lysozyme), followed by sonication on ice for 40 seconds. The suspensions were incubated at 37° C. with shaking for 30 min, followed by being frozen overnight at −20° C. Upon thawing, the inclusion bodies were harvested by centrifugation. The inclusion body pellets were resuspended and washed with 200 mL of wash solution (50 mM Tris pH 7.5, 100 mM NaCl, 2 mM EDTA), and harvested by centrifugation. The inclusion body pellets were washed with 200 mL of water, harvested by centrifugation, and lyophilized.

All the above constructs formed inclusion bodies and remained as pellets under the conditions of harvest and washes.

Example 4

Solubilization of Solubility Tags IBT187.1, IBT233, and Fusion Peptides IBT187.HC263, IBT233.HC263, and IBT187.H2-TonB-G3 at pH 10

The purpose of this example is to describe the solubilization of representative peptides by resuspension of inclusion bodies at alkaline pH.

Constructs comprising multi-functional solubility tags IBT187.1 and IBT233 and fusion peptides IBT187.HC263, IBT233.HC263, and IBT187.H2-TonB-G3 were individually expressed as inclusion bodies in E. coli. This indicates that under normal physiological conditions (around neutral pH and in the presence of salt as found in the cells) these peptides would be in insoluble form as observed in Example 3. The recovered inclusion bodies were tested for solubility in de-ionized water adjusted to pH 10 with sodium hydroxide.

In each case the inclusion bodies were solubilized at 20 μM concentration of the inclusion bodies.

Example 5

Additional Multifuntional Inclusion Body Tags Designed to Have Controllable Solubility The purpose of this example is to demonstrate that additional peptide solubility tags and/or fusion peptides comprising such multi-functional solubility tags can be prepared from structurally similar peptide tags. The present solubility tags and/or fusion peptides comprising at least one of the solubility tags are processable by controlling their solubility via changing of the physio-chemical conditions of the medium.

Variants of inclusion body tag IBT139 (SEQ ID NO: 14; see U.S. Pat. Nos. 7,678,883 and 7,794,979) were prepared. IBT139 and the variant peptide tags derived from IBT139 were prepared and tested for controllable solubility. Table 1 provides data on the various multi-functional solubility tags.

TABLE 1

| Peptide Tag Name | Amino Acid Sequence[1] | SEQ ID NO: | Core Motif(s) | SEQ ID NO(s): of Core Motif(s) |
|---|---|---|---|---|
| IBT139 | MQQRFQWQFEQQPRGQQRFQWQFEQQPRGQQRFQWQFEQQPEGQQRFQWQFEQQGSDP | 14 | QQRFQWQFEQQ | 89 |
| IBT187.1 | MQQKFKWKFQQQPRGQQKFKWKFQQQPRGQQKFKWKFQQQPEGQQKFKWKFQKQ | 4 | QQKFKWKFQQQ QQKFKWKFQKQ | 99 102 |
| IBT201 | MASQQRFQWQFQQQPRGQQRFQWQFQQQPEGQQRFQWQFQQQGPGSDP | 15 | QQRFQWQFQQQ | 90 |
| IBT202 | MASQQRFQWQFQQQPRGQQRFQWQFQQQPRGQQRFQWQFQQQPEGQQRFQWQFQQGPGSDP | 16 | QQRFQWQFQQQ | 90 |
| IBT203 | MASQQRFQWQFQQQPRGQQRFQWQFQQQPEGQQRFQWQFQQQGPGSGGAGSPGSAGGPGSDP | 17 | QQRFQWQFQQQ | 90 |
| IBT204 | MASQQRFQWQFQQQPRGQQRFQWQFQQQPRGQQRFQWQFQQQPEGQQRFQWQFQQQGPGSGGAGSPGSAGGPGSDP | 18 | QQRFQWQFQQQ | 90 |
| IBT205 | MASQQRFQWQFRQQPRGQQQFRWQFQQQPEGQQRFQWQFRQQGPGSGGAGSPGSAGGPGSDP | 19 | QQRFQWQFRQQ QQQFRWQFQQQ | 92 86 |
| IBT206 | MASQQQFRWQFQQQPRGQQRFQWQFRQQPEGQQQFQWRFQQQGPGSGGAGSPGSAGGPGSDP | 20 | QQQFRWQFQQQ QQRFQWQFRQQ | 86 92 |
| IBT207 | MASQQRFRWRFQQQPRGQQRFEWEFQQQPRGQQRFRWRFQQQPEGQQRFEWEFQQQGPGSDP | 21 | QQRFRWRFQQQ QQRFEWEFQQQ | 98 100 |
| IBT208 | MASQQRFRWRFQQQPRGQQRFEWEFQQQPRGQQRFRWRFQQQPEGQQRFEWEFQQQGPGSGGAGSPGSAGGPGSDP | 22 | QQRFRWRFQQQ QQRFEWEFQQQ | 98 100 |

TABLE 1-continued

| Peptide Tag Name | Amino Acid Sequence[1] | SEQ ID NO: | Core Motif(s) | SEQ ID NO(s): of Core Motif(s) |
|---|---|---|---|---|
| IBT209 | MAS<u>QQRFQWQFQWQFEQQ</u>PRG<u>QQRFQWQFQWQFEQQ</u>PEG<u>QQRFQWQFQWQFEQQ</u>GPGSDP | 23 | QQRFQWQFQWQFEQQ | 91 |
| IBT210 | MAS<u>QQRFQWQFQWQFEQQ</u>PRG<u>QQRFQWQFQWQFEQQ</u>PEG<u>QQRFQWQFQWQFEQQ</u>GPGSGGAGSPGSAGGPGSDP | 24 | QQRFQWQFQWQFEQQ | 91 |
| IBT212 | MAS<u>QQRFRWQFQWQFEQQ</u>PRG<u>QQRFRWQFQWQFEQQ</u>PEG<u>QQRFRWQFQWQFEQQ</u>GPGSGGAGSPGSAGGPGSDP | 25 | QQRFRWQFQWQFEQQ | 96 |
| IBT214 | MAS<u>QQRFRWQFRWQFEQQ</u>PRG<u>QQRFQWQFRWQFEQQ</u>PEG<u>QQRFRWQFRWQFEQQ</u>GPGSGGAGSPGSAGGPGSDP | 26 | QQRFRWQFRWQFEQQ<br>QQRFQWQFRWQFEQQ | 97<br>93 |
| IBT216 | MAS<u>QQRFQWQFRWQFEQQ</u>PRG<u>QQRFRWQFRWQFEQQ</u>PEG<u>QQRFQWQFRWQFEQQ</u>GPGSGGAGSPGSAGGPGSDP | 27 | QQRFQWQFRWQFEQQ<br>QQRFRWQFRWQFEQQ | 93<br>97 |
| IBT218 | MAS<u>QQRFQFQFQFEQQ</u>PRG<u>QQRFQFQFQFEQQ</u>PEG<u>QQRFQFQFQFEQQ</u>GPGSGGAGSPGSAGGPGSDP | 28 | QQRFQFQFQFEQQ | 88 |
| IBT220 | MAS<u>QQRFRFRFQFEQQ</u>PRG<u>QQRFRFQFQFEQQ</u>PEG<u>QQRFRFRFQFEQQ</u>GPGSGGAGSPGSAGGPGSDP | 29 | QQRFRFRFQFEQQ<br>QQRFRFQFQFEQQ | 95<br>94 |
| IBT222 | MAS<u>QQRFRFQFQFEQQ</u>PRG<u>QQRFRFRFQFEQQ</u>PEG<u>QQRFRFQFQFEQQ</u>GPGSGGAGSPGSAGGPGSDP | 30 | QQRFRFQFQFEQQ<br>QQRFRFRFQFEQQ | 94<br>95 |
| IBT223 | MAS<u>QQRFQWQFEQQ</u>PRG<u>QQRFQWQFEQQ</u>PRG<u>QQRFQWQFEQQ</u>PEG<u>QQRFQWQFEQQ</u>GSDP | 31 | QQRFQWQFEQQ | 89 |
| IBT224 | MAS<u>QQRFQWQFQQQ</u>PRG<u>QQRFQWQFQQQ</u>PRG<u>QQRFQWQFQQQ</u>PEG<u>QQRFQWQFQQQ</u>GSGSDP | 32 | QQRFQWQFQQQ | 90 |
| IBT225 | MAS<u>QQRFQWQFQQQ</u>PRG<u>QQRFQWQFQQQ</u>PRG<u>QQRFQWQFQQQ</u>PEG<u>QQRFQWQFQQQ</u>GPGSGGAGSPGSAGGPGSGSDP | 33 | QQRFQWQFQQQ | 90 |
| IBT229 | MAS<u>QQHFQWQFEQQ</u>PRG<u>QQHFQWQFEQQ</u>PRG<u>QQHFQWQFEQQ</u>PEG<u>QQHFQWQFEQQ</u>GSDP | 34 | QQHFQWQFEQQ | 83 |
| IBT230 | MAS<u>QQHFQWQFEQQ</u>PRG<u>QQHFQWQFEQQ</u>PRG<u>QQHFQWQFEQQ</u>PEG<u>QQHFQWQFEQQ</u>GPGSGGAGSPGSAGGPGSDP | 35 | QQHFQWQFEQQ | 83 |
| IBT232 | MAS<u>QQHFHWQFEQQ</u>PRG<u>QQHFHWQFEQQ</u>PRG<u>QQHFHWQFEQQ</u>PEG<u>QQHFHWQFEQQ</u>GSDP | 36 | QQHFHWQFEQQ | 82 |
| IBT233 | MAS<u>HQHFHWQFEQQ</u>PRG<u>HQHFHWQFEQQ</u>PRG<u>HQHFHWQFEQQ</u>PEG<u>HQHFHWQFEQQ</u>GS | 37 | HQHFHWQFEQQ | 80 |
| IBT239 | MAS<u>QQRFQWQFEQQ</u>PRG<u>QQRFQWQFEQQ</u>PRG<u>QQRFQWQFEQQ</u>PEG<u>QQRFQWQFEQQ</u>GPGSGGAGSPGSAGGPGSDP | 38 | QQRFQWQFEQQ | 89 |
| IBT241 | MAS<u>QQHFHWQFEQQ</u>PRG<u>QQHFHWQFEQQ</u>PRG<u>QQHFHWQFEQQ</u>PEG<u>QQHFHWQFEQQ</u>GPGSGGAGSPGSAGGPGSDP | 39 | QQHFHWQFEQQ | 82 |
| IBT242 | MAS<u>HQHFHWQFEQQ</u>PRG<u>HQHFHWQFEQQ</u>PRG<u>HQHFHWQFEQQ</u>PEG<u>HQHFHWQFEQQ</u>GPGSGGAGSPGSAGGPGSDP | 40 | HQHFHWQFEQQ | 80 |
| IBT247 | MAS<u>QQHFHWQFEQQ</u>PRG<u>QQHFHWQFEQQ</u>PRG<u>QQHFHWQFEQQ</u>PRG<u>QQHFHWQFEQQ</u>PRRGPGSGGAGSPGSAGGPGS | 41 | QQHFHWQFEQQ | 82 |
| IBT248 | MAS<u>HQHFHWQFEQQ</u>PRG<u>HQHFHWQFEQQ</u>PRG<u>HQHFHWQFEQQ</u>PRG<u>HQHFHWQFEQQ</u>PRRGPGSGGAGSPGSAGGPGS | 42 | HQHFHWQFEQQ | 80 |
| IBT249 | MAS<u>QQRFQWQFEQQ</u>GGAGQGGLGSQGAGQGAG<u>QQRFQWQFEQQ</u>GGAGQGGYGGLGSQGAGRGGQGAG<u>QQRFQWQFEQQ</u>GPGSGGAGSPGSAGGPGSDP | 43 | QQRFQWQFEQQ | 89 |
| IBT254 | MAS<u>QQHFHWQFEQQ</u>GGAGQGGLGSQGAGQGAG<u>QQHFHWQFEQQ</u>GGAGQGGYGGLGSQGAGRGGQGAG<u>QQHFHWQFEQQ</u>GPGSGGAGSPGSAGGPGSDP | 44 | QQHFHWQFEQQ | 82 |

TABLE 1-continued

| Peptide Tag Name | Amino Acid Sequence[1] | SEQ ID NO: | Core Motif(s) | SEQ ID NO(s): of Core Motif(s) |
|---|---|---|---|---|
| IBT255 | MAS<u>HQHFHWQFEQQ</u>GGAGQGGLGSQGAGQGAG<u>HQHFHWQFEQQ</u>GAGQGGYGGLGSQGAGRGGQGAG<u>HQHFHWQFEQQ</u>GAGQGGYGGLGSQGAGRGGLGGQGAG<u>HQHFHWQFEQQ</u>GPSGGAGSPGSAGGPGSDP | 45 | HQHFHWQFEQQ | 80 |
| IBT258 | MAS<u>QQQFQWQFEQQ</u>PEG<u>QQQFQWQFEQQ</u>PEG<u>QQQFQWQFEQQ</u>GPSGGAGSPGSAGGPGS | 46 | QQQFQWQFEQQ | 85 |
| IBT259 | MAS<u>QQQFRWRFEQQ</u>PEG<u>QQQFEWEFEQQ</u>PRG<u>QQQFRWRFEQQ</u>PEG<u>QQQFEWEFEQQ</u>GPSGGAGSPGSAGGPGS | 47 | QQQFRWRFEQQ<br>QQQFEWEFEQQ | 87<br>101 |
| IBT260 | MAS<u>QQHFHWQFEQQ</u>PEG<u>QQHFHWQFEQQ</u>PRG<u>QQHFHWQFEQQ</u>PEG<u>QQHFHWQFEQQ</u>GPSGGAGSPGSAGGPGS | 48 | QQHFHWQFEQQ | 82 |
| IBT261 | MAS<u>HQHFHWQFEQQ</u>PEG<u>HQHFHWQFEQQ</u>PRG<u>HQHFHWQFEQQ</u>PEG<u>HQHFHWQFEQQ</u>GPSGGAGSPGSAGGPGS | 49 | HQHFHWQFEQQ | 80 |
| IBT262 | MAS<u>QQRFRWRFQQQ</u>GGAGQGGLGSQGAGQGAG<u>QQRFEWEFQQQ</u>GGAGQGGYGGLGSQGAGRGGQGAG<u>QQRFRWRFQQQ</u>GGAGQGGYGGLGSQGAGRGGLGGQGAG<u>QQRFEWEFQQQ</u>GPSGGAGSPGSAGGPGSDP | 50 | QQRFRWRFQQQ<br>QQRFEWEFQQQ | 98<br>100 |
| IBT263 | MAS<u>QQRFRWRFQQQ</u>GGAGQGGLGSQGAGQGAG<u>QQRFEWEFQQQ</u>GGAGQGGYGGLGSQGAGRGGQGAG<u>QQRFRWRFQQQ</u>GGAGQGGYGGLGSQGAGRGGLGGQGAG<u>QQRFEWEFQQQ</u>GPSGGAGSPGSAGGPGSGPGSGGAGSPGSAGGPGSDP | 51 | QQRFRWRFQQQ<br>QQRFEWEGQQQ | 98<br>100 |
| IBT282 | MAS<u>QQHFHWHFQQQ</u>PRG<u>QQHFHWHFQQQ</u>PEG<u>QQHFHWHFQQQ</u>GPSGGAGSPGSAGGPGS | 52 | QQHFHWHFQQQ | 82 |
| IBT283 | MAS<u>QQHFHWHFQQQ</u>PRG<u>QQKFKWKFQQQ</u>PEG<u>QQHFHWHFQQQ</u>GPSGGAGSPGSAGGPGS | 53 | QQHFHWHFQQQ<br>WWKFKWKFQQQ | 82<br>99 |
| IBT284 | MAS<u>QQKFHWHFQQQ</u>PRG<u>QQKFHWHFQQQ</u>PEG<u>QQKFHWHFQQQ</u>GPSGGAGSPGSAGGPGS | 54 | QQKFHWHFQQQ | 84 |
| IBT287 | MAS<u>QQKFKWKFQQQ</u>PRG<u>QQKFKWKFQQQ</u>PEG<u>QQKFKWKFQQQ</u>GPSGGAGSPGSAGGPGS | 55 | QQKFKWKFQQQ | 99 |
| IBT289 | MAS<u>QQKFKWKFQQQ</u>PRG<u>QQHFHWHFQQQ</u>PEG<u>QQKFKWKFQQQ</u>GPSGGAGSPGSAGGPGS | 56 | QQKFKWKFQQQ<br>QQHFHWHFQQQ | 99<br>81 |
| IBT290 | MAS<u>QQKFHWKFQQQ</u>PRG<u>QQKFHWKFQQQ</u>PEG<u>QQKFHWKFQQQ</u>GPSGGAGSPGSAGGPGS | 57 | QQKFHWKFQQQ | 103 |
| IBT294 | MASGPCG<u>QQHFHWHFQQQ</u>PRG<u>QQKFKWKFQQQ</u>PEG<u>QQHFHWHFQQQ</u>GPSGGAGSPGSAGGPGS | 58 | QQHFHWHFQQQ<br>QQKFKWKFQQQ | 82<br>99 |
| IBT295 | MASGPCG<u>QQKFHWHFQQQ</u>PRG<u>QQKFHWHFQQQ</u>PEG<u>QQKFHWHFQQQ</u>GPSGGAGSPGSAGGPGS | 59 | QQKFHWHFQQQ | 84 |
| IBT297 | MASGPCG<u>QQKFKWKFQQQ</u>PRG<u>QQKFKWKFQQQ</u>PRG<u>QQKFKWKFQQQ</u>PEG<u>QQKFKWKFQKQ</u>GPSGGAGSPGSAGGPGS | 60 | QQKFKWKFQQQ<br>QQKFKWKFQKQ | 99<br>102 |
| IBT298 | MASGPCG<u>QQRFQWQFEQQ</u>PRG<u>QQRFQWQFEQQ</u>PRG<u>QQRFQWQFEQQ</u>PEG<u>QQRFQWQFEQQ</u>GPSGGAGSPGSAGGPGS | 61 | QQRFQWQFEQQ | 89 |
| IBT299 | MASGPCG<u>QQRFQWQFEQQ</u>GGAGQGGLGSQGAGQGAG<u>QQRFQWQFEQQ</u>GGAGQGGYGGLGSQGAGRGGQGAG<u>QQRFQWQFEQQ</u>GGAGQGGYGGLGSQGAGRGGLGGQGAG<u>QQRFQWQFEQQ</u>GPSGGAGSPGSAGGPGS | 62 | QQRFQWQFEQQ | 89 |
| IBT310 | MAS<u>HQHFHWQFEQQ</u>GGAGQGGLGSQGAGQGAG<u>HQHFHWQFEQQ</u>GGAGQGGYGGLGSQGAGRGGQGAG<u>HQHFHWQFEQQ</u>GGAGQGGYGGLGSQGAGRGGLGGQGAG<u>HQHFHWQFEQQ</u>GPRSGGAGSPGSAGGPGSGPGSGGAGSPGSAGGPGSDP | 63 | HQHFHWQFEQQ | 80 |
| IBT311 | MAS<u>HQHFHWQFEQQ</u>GGAGQGGLGSQGAGQGAG<u>HQHFHWQFEQQ</u>GGAGQGGYGGLGSQGAGRGGQGAG<u>HQHFHWQFEQQ</u>GGAGQGGYGGLGSQGAGRGGLGGQGAG<u>HQHFHWQFEQQ</u>GPRSAHSPGHSAGHPGSDP | 64 | HQHFHWQFEQQ | 80 |
| IBT312 | MAS<u>HQHFHWQFEQQ</u>GGAGQGGLGSQGAGQGAG<u>HQHFHWQFEQQ</u>GGAGQGGYGGLGSQGAGRGGQGAG<u>HQHFHWQFEQQ</u>GGAGQGGYGGLGSQGAGRGGLGGQGAG<u>HQHFHWQFEQQ</u>GPRSGAHSPGSAHPGSHPGSGHAGSPHSAGHPGSDP | 65 | HQHFHWQFEQQ | 80 |
| IBT313 | MAS<u>HQHFHWQFEQQ</u>GGAGQGGLGSQGAGQGAG<u>HQHFHWQFEQQ</u>GGAGQGGYGGLGSQGAGRGGQGAG<u>HQHFHWQFEQQ</u>GGAGQGGYGGLGSQGAGRGGLGGQGAG<u>HQHFHWQFEQQ</u>GPSGASPGSDP | 66 | HQHFHWQFEQQ | 80 |

TABLE 1-continued

| Peptide Tag Name | Amino Acid Sequence[1] | SEQ ID NO: | Core Motif(s) | SEQ ID NO(s): of Core Motif(s) |
|---|---|---|---|---|
| IBT314 | MAS<u>HQHFHWQFEQQ</u>GGAGQGGLGSQGAGQGAG<u>HQHFHWQFEQQ</u>GGAGQGGYGGLG SQGAGRGGQGAG<u>HQHFHWQFEQQ</u>GGAGQGGYGGLGSQGAGRGGLGGQGAG<u>HQHFH WQFEQQ</u>GPHSGHSGSDP | 67 | HQHFHWQFEQQ | 80 |
| IBT315 | MAS<u>HQHFHWQFEQQ</u>GGAGQGGYGGLGSQGAGRGGQGAG<u>HQHFHWQFEQQ</u>GPGSGG AGSPGSAGGPGS | 68 | HQHFHWQFEQQ | 80 |
| IBT316 | MAS<u>HQHFHWQFEQQ</u>GGAGQGGYGGLGSQGAGRGGQGAG<u>HQHFHWQFEQQ</u>GGAGQG GYGGLGSQGAGRGGLGGQGAG<u>HQHFHWQFEQQ</u>GPGSGGAGSPGSAGGPGS | 69 | HQHFHWQFEQQ | 80 |
| IBT317 | MAS<u>HQKFHWQFEQQ</u>GGAGQGGLGSQGAGQGAG<u>HQKFHWQFEQQ</u>GGAGQGGYGGLG SQGAGRGGQGAG<u>HQKFHWQFEQQ</u>GGAGQGGYGGLGSQGAGRGGLGGQGAG<u>HQKFH WQFEQQ</u>GPGSGGAGSPGSAGGPGS | 70 | HQKFHWQFEQQ | 104 |
| IBT320 | MAS<u>HQHFHWQFEQQ</u>GGAGQGGLGSQGAGQGAG<u>HQHFHWQFEQQ</u>GGAGQGGLGSQG AGQGAG<u>HQHFHWQFEQQ</u>GGAGQGGLGSQGAGQGAG<u>HQHFHWQFEQQ</u>GPGSGGAGS PGSAGGPGS | 71 | HQHFHWQFEQQ | 80 |
| IBT321 | MAS<u>HQHFHWQFEQQ</u>GGAGQGGYGGLGSQGAGRGGLGGQGAG<u>HQHFHWQFEQQ</u>GGA GQGGYGGLGSQGAGRGGLGGQGAG<u>HQHFHWQFEQQ</u>GGAGQGGYGGLGSQGAGRGG LGGQGAG<u>HQHFHWQFEQQ</u>GPGSGGAGSPGSAGGPGS | 72 | HQHFHWQFEQQ | 80 |
| IBT326 | M<u>QQRFQWQFEQQ</u>NGKT<u>QQRFQWQFEQQ</u>GS | 73 | QQRFQWQFEQQ | 89 |
| IBT327 | M<u>QQRFQWQFEQQ</u>YNGK<u>QQRFQWQFEQQ</u>GS | 74 | QQRFQWQFEQQ | 89 |
| IBT332 | MAS<u>HQHFHWQFEQQ</u>GGAGQGGLGCQGAGQGAG<u>HQHFHWQFEQQ</u>GGAGQGGYGGLG CQGAGRGGQGAG<u>HQHFHWQFEQQ</u>GGAGQGGYGGLGCQGAGRGGLGGQGAG<u>HQHFH WQFEQQ</u>GPRSGAHSPGHSAGHPGS | 75 | HQHFHWQFEQQ | 80 |
| IBT334 | MAS<u>HQHFHWQFEQQ</u>GPGSGGAGSPGSAGGPGSHDHKNQKETHQRHAAGPGSGGAG SPGSAGGPGS<u>HQHFHWQFEQQ</u>GPGSGGAGSPGSAGGPGSTAEIQSSKNPNPHPQR SWTNGPGSGGAGSPGSAGGPGS<u>HQHFHWQFEQQ</u>GPGSGGAGSPGSAGGPGSTPPE LAHTPHHLAQTRLTDRGPGSGGAGSPGSAGGPGS<u>HQHFHWQFEQQ</u>GPGSGGAGSP GSAGGPGS | 76 | HQHFHWQFEQQ | 80 |
| IBT340 | MAS<u>HQHFHWQFEQQ</u>GGAGQGGLGCQGAGQGAG<u>HQHFHWQFEQQ</u>GGAGQGGYGGLG CQGAGRGGQGAG<u>HQHFHWQFEQQ</u>GGAGQGGYGGLGCQGAGRGGLGGQGAG<u>HQHFH WQFEQQ</u>GPGSGGAGSPGSAGGPGS | 77 | HQHFHWQFEQQ | 80 |

[1] = core motif(s) underlined.

The multi-functional solubility tags in Table 1 can be defined by the following general structures:

SEQ ID NO: 1-Spacer-[[SEQ ID NO: 1]-[Spacer]$_m$]$_n$ or

SEQ ID NO: 2-Spacer-[[SEQ ID NO: 2]-[Spacer]$_m$]$_n$ wherein SEQ ID NO:1 and SEQ ID NO: 2 represent core motifs within each peptide tag;

SEQ ID NO: 1 is

Xaa1-Gln-[Xaa2]$_p$-[Phe-Xaa3-Xaa4-Xaa5]$_s$-Phe-Xaa6-[Xaa7]$_q$-[Gln]$_r$;

and
SEQ ID NO: 2 is

Xaa1-Gln-Xaa8-[Xaa4--Xaa8]$_s$-Phe-[Glu-Gln-Gln]$_r$;

wherein
Xaa1=Gln or His;
Xaa2=Gln, Arg, His, or Lys;
Xaa3=Gln, His, Lys, Arg, or Glu;
Xaa4=Trp or Phe;
Xaa5=Gln, His, Lys, Arg or Glu;
Xaa6=Glu, Gln, or Arg;
Xaa7=Gln or Lys;
Xaa8=Asp, Glu, Gln, His, Lys, or Arg;
p, q, and r are independently 0 or 1;
s is an integer ranging from 1 to 5;
n is an integer ranging from 1 to 10;
m=n−1; and
Spacer=a peptide linker ranging from 1 to 100 amino acids in length.

The IBT139-derived variant inclusion body tags in Table 1 were prepared using standard molecular biology techniques. These multi-functional solubility tags were prepared using several approaches including, but not limited to, varying the amino acid composition of the core motifs, changing the number of core motif sequences, selecting different combinations of core motifs, altering the length and composition of the peptide spacers separating the core motifs.

The solubility and insolubility characteristics of the IBTs fused to the soluble peptide of interest (POI) HC263 were evaluated. All the peptides were expressed in E. coli as inclusion bodies indicating their insolubility at neutral pH. Their controllable solubility by using pH (in this case pH 12) was assessed by making a 1-2 mL suspension of fusion peptide in water (~1-2 mg/mL), adjusting the pH to 12 with NaOH, separating the insoluble fraction (pellet) from the soluble fraction (supernatant) by centrifugation (10 min at 15,000×g) and assaying the supernatant by polyacrylamide gel electrophoresis to confirm the solubilization of the peptide. The soluble fraction supernatants were transferred to a new tube and the control of re-insolubilization was assessed by shifting the pH to pH 7.5 by 20 mM Tris 50 mM NaCl, separating the insoluble fraction (pellet) from the soluble fraction (supernatant) by centrifugation (10 min at 15,000×g) and assaying the insoluble fraction (pellet) by polyacrylamide gel electrophoresis to confirm that the fusion peptide was once again insoluble.

All of the multi-functional IBTs tested as fusions to peptide HC263 formed inclusion bodies inside *E. coli*, could be solubilized at pH 12 and rendered insoluble at pH 7.5 in presence of 50 mM NaCl, thus satisfying the functional feature of controllable solubility of the multi-functional solubility tags.

Example 6

Solubility Tags Providing Additional Functionality

The purpose of this example is to demonstrate that the solubility tags (defined by SEQ ID NO: 1 and SEQ ID NO: 2; Example 5) that are not removed from the peptide of interest ("leave on tags"; LOTs) provide additional functionality to the fusion protein beyond inclusion body formation and controllable solubility during downstream processing. More specifically, the presence of the multi-functional solubility tag can be used to functionalize a target surface by controlling or enhancing deposition of the fusion peptide on a surface via the presence of the multi-functional solubility tag.

The peptide of interest (POI) may be selected to have a binding affinity for a first target material. When coupled to a multi-functional solubility tag providing a binding affinity for a second target material (wherein the first and second materials are different) the resulting fusion peptide enables one to couple the first and second target materials. In one embodiment, the present example demonstrates the ability of fusion proteins comprising the present multi-functional solubility tags to act as bridging agents between the two target materials.

Seven peptides were subjected to a magnetic bead assay described in this example to illustrate the concept that a "leave-on" solubility tag (multi-functional solubility tags and/or fusion peptides comprising such peptide tags) has targeted surface activity. The peptides and their associated functionalities are listed in Table 2.

TABLE 2

Peptides and their associated functionalities

| Peptide Name (SEQ ID NO:) | Classification | Target material affinity (predicted) | Function(s) |
| --- | --- | --- | --- |
| IBT187.1 (SEQ ID NO: 4) | Multi-functional Inclusion Body Tag (IBT) | Silica (e.g. silica particles) | Presence in fusion peptides responsible for inclusion body formation when coupled to a peptide of interest. |
| HC263 (SEQ ID NO: 6) | Peptide of Interest (POI) | Cobalt-nitrilotriacetic acid resin (e.g. Co-NTA coated magnetic beads) | HC263 contains a hex-his tag (His6) that is predicted to bind to Co-NTA resins. |
| IBT187.HC263 (SEQ ID NO: 8) | Fusion peptide (IBT-POI) | Silica particles and Co-NTA coated magnetic beads | IBT187 predicted to bind to silica while HC263 predicted to bind to Co-NTA resin coated magnetic beads |
| IBT187.H2-TonB-G3 (SEQ ID NO: 10) | Fusion peptide (IBT-POI) | Silica (e.g., silica particles only) | Same sequence as fusion peptide IBT187.HC263 except lacking the His6 tag. Predicted to bind to silica only. |
| IBT233 (SEQ ID NO: 37) | Multi-functional Inclusion Body Tag (IBT) | Silica (e.g., silica particles only) | Presence in fusion peptides responsible for inclusion body formation when coupled to a peptide of interest. |
| IBT233.HC263 (SEQ ID NO: 13) | Fusion peptide (IBT-POI) | Silica particles and Co-NTA coated magnetic beads | IBT233 predicted to bind to silica while the His6 portion of HC263 predicted to bind to Co-NTA resin coated magnetic beads. |
| HC353 (SEQ ID NO: 298) | Peptide of Interest (POI) | Hair and iron oxide particles (with silica coating) | HC353 contains a hair-binding domain (HP2-TonB-Grey3) linked to an iron oxide pigment particle binding domain |

The seven peptides were individually dissolved in water adjusted to pH 10 with sodium hydroxide at peptide concentrations of 20 µM each as described in Example 4. One mL of the peptide solution was transferred to 1.8-mL microfuge tubes. Silica particles (i.e., Schott glass, approximately 600 nm average diameter particles) were added to a final concentration of 0.5% (w/v). The mixtures were incubated for 60 minutes with agitation. KCl was added to 50 mM concentration to promote insolubility of the "leave on" multi-functional solubility tag and the mixtures were incubated with agitation for an additional 60 minutes. The particles were spun down for 1 minute at 13000 rpm in a centrifuge. The supernatant was discarded and the resulting particle pellet resuspended in 1 mL of pH 10 water. The particles were spun down for 1 min at 13000 rpm in a centrifuge to remove any remaining unbound peptide. The supernatant was discarded and the resulting particle pellet was resuspended in 1 mL of 10 mM MES, pH 5 buffer. Five microliters of magnetic DYNABEADS® TALON™ (magnetic beads coated with Co-NTA resin; Invitrogen, Carlsbad, Calif., Cat #101.01D) were washed according to manufacturer's instructions. The TALON™ technology is comprised of a tetradentate metal chelator which binds to the imidazole rings of a poly histidine peptide chain resin. Approximately 100 µL of silica particle suspension, 5 µL of TALON™ beads and 500 µL of TALON™ binding buffer (50 mM Na-phosphate, pH 8.0, 300 mM NaCl, 0.01% TWEEN®-20) were mixed in a 1.8-mL microfuge tube. After 10 minutes of gentle mixing, the tubes were placed vertically on a magnet (Dynal magnetic particle concentrator, Invitrogen, Cat #120.20D). The magnetic TALON™ beads travel to the center of the magnet as a globule and unbound silica drops to the bottom of the tube. The tubes were rotated around their axis (while still on magnet) to apply shear force on the particles. In the case of peptide-mediated binding of the two particle types to each other, all the particles would travel to the center of the tubes, and could not be broken up via rotating the tubes. There is also a noticeable color change, silica alone is white, TALON™ beads are brown, and the mixed particles are more orange in color. Table 3 below shows which peptides in the magnetic bead assay described in Example 6 were able to facilitate binding between the two types of target materials (i.e., silica particles and Co-NTA coated magnetic particles).

TABLE 3

Description and functions of multi-functional inclusion body tags, fusion peptides, and peptides of interest

| Peptide ID (SEQ ID NO:) | Composition | Expected functions | Observed Surface-binding Activity[1] |
|---|---|---|---|
| No peptide | — | control | — |
| IBT187.1 (SEQ ID NO: 4) | Multi-functional inclusion body tag (IBT) | Silica only | — |
| HC263 (SEQ ID NO: 6) | Peptide of Interest (POI) | Co-NTA coated magnetic beads | — |
| IBT187.HC263 (SEQ ID NO: 8) | Fusion peptide (IBT-POI) | Silica (particles) and Co-NTA coated magnetic beads | ++++ |
| IBT187.H2-TonB-G3 (SEQ ID NO: 10) | Fusion peptide (IBT-POI) | Silica only | + |
| IBT233 (SEQ ID NO: 37) | Multi-functional inclusion body tag (IBT) | Silica only | — |
| IBT233.HC263 (SEQ ID NO: 13) | Fusion peptide (IBT-POI) | Silica (particles) and Co-NTA coated magnetic beads | ++++ |
| HC353 (SEQ ID NO: 298) | Peptide of Interest (POI) | Hair and Iron Oxide particles | — |

[1]= Note:
++++ refers to strong binding between particle types that cannot be disrupted by rotating tubes. + refers to very weak binding that can largely be disrupted by rotating tubes. — refers to no observable binding even before rotating tubes.

Figure 3:
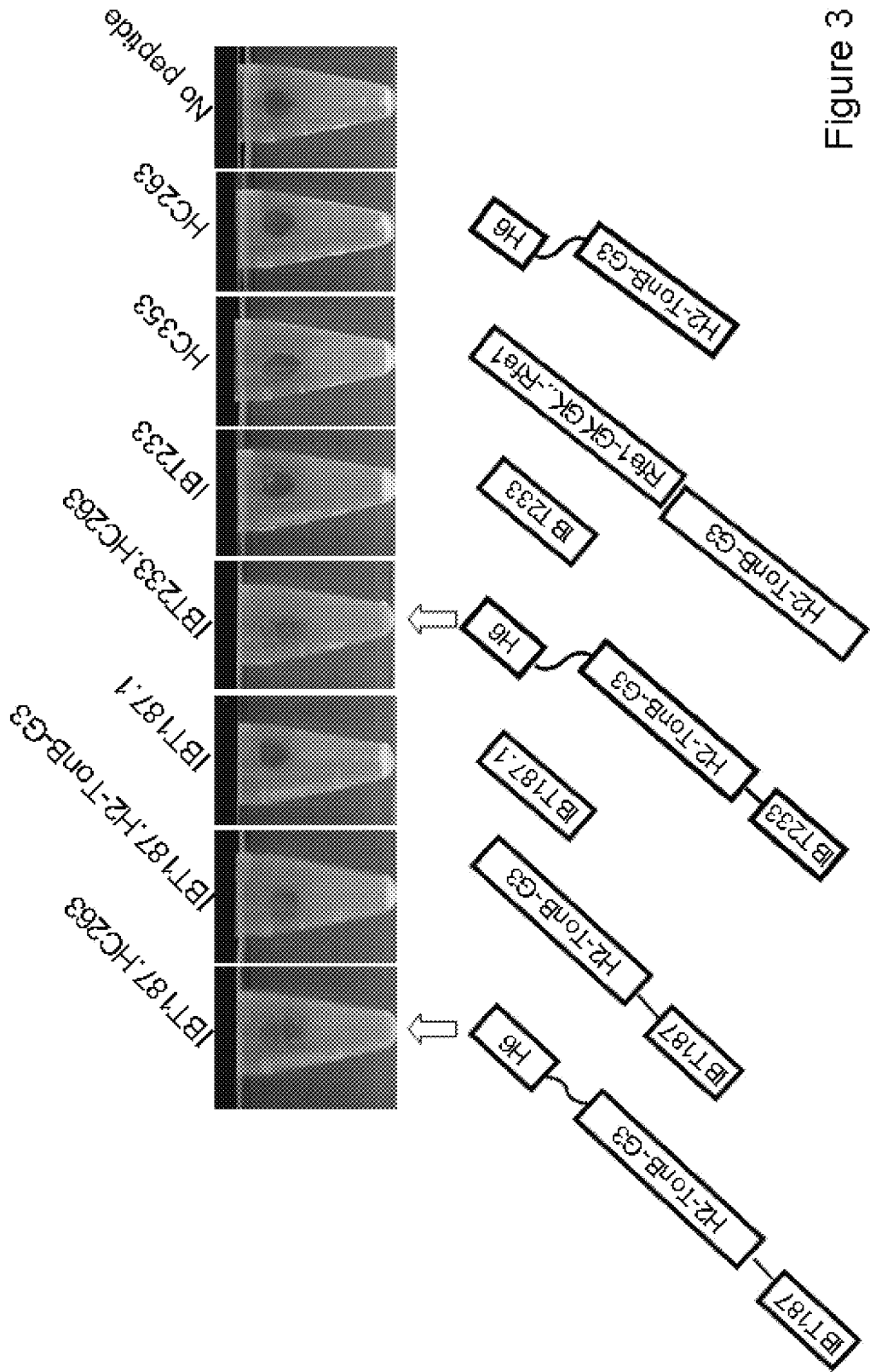
FIG. 3 comprises an image of spins tubes illustrating the effects of the various fusion peptides on binding two different surfaces together non-covalently. Only peptides with specific binding domains for the two respective surfaces can anchor the particles together.

The results of magnetic bead assay described in Example 6 and Table 3 are also shown in FIG. 3 and indicate that both binding domains (IBT & POI) must be present for the peptide to link the two particle types together.

IBT187.1 and IBT233 are excellent examples of multi-functional "leave on" peptidic solubility tags that (when coupled to a peptide of interest having surface binding activity) facilitate insoluble inclusion body formation, exhibit reversible solubility, and have demonstrated surface binding activity.

Example 7

Fusion Peptide IBT233.HC263 Can Mediate Binding Between Two Target Materials

The purpose of this example is to demonstrate an example of bridging the surfaces of two target materials using a fusion peptide comprising a multi-functional inclusion body tag having affinity for a first target material (a pigment) and a peptide of interest having affinity for a second target material (a body surface, such as hair).

Fusion peptide IBT233.HC263 (SEQ ID NO: 13) contains two engineered structural domains: an inclusion body tag (IBT233; SEQ ID NO: 37)) and a POI (HC263; SEQ ID NO: 6).

The constructs comprising IBT233 and the physio-chemical environment are described in Examples 1-5 for its use as a multi-functional (tri-functional in this case) inclusion body tag. The three functions of IBT233 (when incorporated in a fusion peptide) are:

1. It promotes fusion peptide insolubility in the *E. coli* cells to facilitate inclusion body formation (Example 2);

2. It provides reversible and controllable solubility for the fusion peptide (Examples 2, 3, 4 and 5); and 3. It provides surface binding activity for silica (Example 6).

In addition to the multi-functional inclusion body tag domain, IBT233.HC263 comprises peptide of interest HC263, which contains two sub-domains; one of which binds to hair and the other hex-His (His6) tag that binds to Co-NTA coated magnetic beads.

This example shows that fusion peptide IBT233.HC263 (SEQ ID NO: 13) can be used to bind pigments to hair. IBT233.HC263 was dissolved in pH 10 water (as described above) at a concentration of 0.5 mg/mL and allowed to gently shake for 1 hour at room temperature (~22° C.). Silica-coated red iron oxide pigments (with an average particle size distribution 200 nm) were added to the IBT233.HC263 containing solution to 0.1% final conc. (w/v) and incubated for 90 min under gentle shaking. KCl was added to 50 mM and the mixture was incubated overnight. The samples were spun down at 10,000 rpm for 2 min in a microfuge, and the supernatant discarded. The mixture was resuspended in pH 10 de-ionized water, vortexed, and spun down again. The supernatant was discarded and the samples were resuspended in 1 mL of 10 mM MES buffer, pH 5. Hair tresses (natural white hair bundle of about 2.5 cm length and 0.5 cm width; International Hair Importers and Products, Bellerose, N.Y.) were added to the microfuge tube containing the fusion peptide-pigment adducts. The hair was incubated for 15 minutes with intermittent vortexing. The tresses were removed and washed under running tap water and gentle embrocation. The hair was dried and the color was measured in X-rite SP64 spectrophotometer, measuring L*, a*, b* values according to Commission Internationale d'Eclairage (CIELAB76).

The experiment was carried out in triplicate, along with no-peptide controls, where everything was carried out identically except no peptide was added to the pigment.

TABLE 4

Color update in the presence of fusion peptide IBT233.HC263

| Sample | Color Uptake (ΔE) | Standard Deviation |
|---|---|---|
| No peptide (control) | 4.9 | 1.4 |
| IBT233.HC263 (SEQ ID NO: 13) | 26.7 | 2.1 |

This example shows that the fusion peptide including the inclusion body tag and the hair-binding domain can mediate the binding of a pigment particle to hair and thus demonstrates the multifunctional role of the inclusion body tag.

Example 8

Fusion Peptide IBT255.AuBD Mediates Binding Between Two Target Materials

The purpose of this example is to demonstrate bridging the surfaces of two target materials using a fusion peptide comprising a multi-functional inclusion body tag having affinity for a first target material to (glass) and a peptide of interest (POI) having affinity for a second target material (gold particle).

Fusion peptide IBT255.AuBD (SEQ ID NO: 497) was prepared using standard cloning and expression techniques similar to those described in Examples 1-3. IBT255.AuBD contains two engineered structural domains: an inclusion body tag (IBT255; SEQ ID NO: 45) and a POI (AuBD, binding to gold; SEQ ID NO: 496).

The constructs comprising IBT255 and the physio-chemical environment are described in Examples 1-5 for its use as a multi-functional (tri-functional in this case) inclusion body tag. The three functions of IBT255 (when incorporated in a fusion peptide) are:

1. It promotes fusion peptide insolubility in the *E. coli* cells to facilitate inclusion body formation (Example 2);
2. It provides reversible solubility for the fusion peptide (Examples 2, 3, 4 and 5); and
3. It provides surface binding activity for gold (see Brown, S., (1997) *Nat. Biotechnol.* 15:269-172).

This example shows that fusion peptide IBT255.AuBD (SEQ ID NO: 497) can be used to bind gold particles to glass. IBT255.AuBD was dissolved in pH 10 water (as described above) at a concentration of 0.5 mg/mL and allowed to gently shake for 1 hour at room temperature (~22° C.). 200 microliters of the solution were spotted onto a microscope glass slide and allowed to incubate for 1 hour at room temperature. The solution was decanted and the glass slide rinsed extensively with distilled water. As a control, the peptide comprised of IBT255 (SEQ ID NO: 45) alone was treated in the same manner as described for the fusion peptide. 200 microliters of a dilute solution (1OD) of 40 nm gold particles in water (Naked Gold, BioAssay Works) were spotted onto the glass slide and incubated for 1 hour at room temperature. The solution was decanted and the glass slide rinsed extensively with distilled water.

Results: On the glass slide incubated with IBT255.AuBD a purple circle (comprised of gold particles of 40 nm size) coinciding with the area of peptide application was visible, indicating the binding of gold particles to the glass. In the case of IBT255 alone, such a purple color was not evident. The experiment shows that IBT255.AuBD is able to anchor gold particles to the glass surface, where IBT255 binds to glass, and the AuBD binds to the gold particles.

Example 9

Accumulation of the Fusion Peptide IBT255.HC263 as Inclusion Bodies in *Bacillus megaterium*

The purpose of this example is to describe the production of a fusion peptide (including multi-functional solubility tag IBT255; SEQ ID NO: 45) in the Gram positive bacterial host *Bacillus megaterium* as insoluble inclusion bodies.

The gene for IBT255.HC263 was ordered from DNA2.0 (Menlo Park, Calif.) codon-optimized for expression in *B. megaterium*. The amino acid sequence of fusion peptide IBT255.HC263 is provided as SEQ ID NO: 499. The gene was cloned into plasmid $pP_{T7}$ (using the kit T7 RNA polymerase expression system for *Bacillus megaterium*' from Mo Bi Tec GmbH, Goettingen, Germany) with restriction sites BsrGI and NaeI at the 5' and 3' end of the gene, respectively. The plasmid was transformed into *B. megaterium* protoplasts based on the suppliers instructions (Mo Bi Tec GmbH). Colonies were inoculated into 3 mL cultures LB/Tet (10 μg/mL)/Chloramphenicol (4.5 mg/mL), induced by addition of 0.5% D-xylose (w/v) when the $OD_{600}$ reached about 0.5 and allowed to grow for another 3 hours. To determine soluble versus insoluble cell content, the cells were lysed with 1 μL of READY-LYSE™ (a recombinant lysozyme preparation available from Epicentre, Madison, Wis.) at 37° C. for 10 min. Soluble and insoluble fractions were analyzed on an SDS-PAGE gel. The fusion product was all found in the insoluble fraction, showing that the tag IBT255 drives its fusion partner into insoluble inclusion bodies in multiple organisms (*E. coli* and *B. megaterium*).

The invention claimed is:

1. A method comprising:
   a) providing a microbial host cell comprising a heterologous nucleic acid molecule encoding an insoluble fusion peptide comprising at least one first portion and at least one second portion, wherein said first portion comprises a multi-functional solubility tag and said second portion comprises a peptide of interest; wherein the multi-functional solubility tag comprises at least two core motifs independently selected from the group consisting of SEQ ID NOs: 80-104;
   b) growing the microbial host cell under conditions whereby the insoluble fusion peptide is produced within the microbial host cell in the form of at least one inclusion body;
   c) recovering the insoluble fusion peptide from the microbial host cell;
   d) subjecting the insoluble fusion peptide to an aqueous medium having a pH at which the insoluble fusion peptide becomes a soluble fusion peptide;
   e) contacting the soluble fusion peptide with a first target material having a surface whereby the fusion peptide non-covalently associates, with a KD or MBs0 value of less than or equal to about 10-5 M, with the surface of the first target material; wherein the association between the fusion peptide and the first target material is dependent upon, or enhanced by, the presence of the multi-functional solubility tag; and
   (f) altering the pH in step (d) to promote or enhance deposition of the soluble fusion peptide on the surface of the first target material.

2. The method of claim 1 wherein pH is increased.

3. The method of claim 1 wherein pH is decreased.

4. The method of claim 1 wherein pH is altered by at least one pH unit.

5. The method of claim 1 wherein the second portion of the fusion peptide is an antimicrobial agent.

6. The method of claim 1 wherein the second portion of the fusion peptide has an affinity for a second target material; wherein the first target material and the second target material are different.

7. The method of claim 1 wherein the first target material is a particle having an average particle size ranging from 100 nm to 10 µas measured by a light scattering method.

8. The method of claim 1 wherein the first target material is selected from the group consisting of a pigment, a body tissue, a cell surface receptor, hair, skin, nail, teeth, oral cavity tissues, plant tissue, a polymer, polystyrene, polyethylene, polypropylene, polytetrafluoroethylene, polyester, polyvinyl chloride, poly (methyl methacrylate), polyethersulfone, polyimide, polyamide, aramids, poly para-phenylene terephthalamide, poly meta-phenylene terephthalamide, poly urethanes, polysaccharides, cellulose, starch, chitin, minerals, silica, silicates, micas, titanium dioxide, alumina, iron oxides, clays, metals, gold, silver, carbon, carbon black, graphite, and carbon nanotubes.

9. The method of claim 6 wherein the second target material is a keratin-containing material selected from the group consisting of skin, nail, and hair.

10. The method of claim 1 wherein the multi-functional solubility tag comprises an amino acid sequence selected from the group consisting of SEQ ID NOs: 4, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66 67, 68, 69, 70, 71, 72, 73, 74, 75, 76, and 77.

11. The method of claim 1 where the multi-functional solubility tag comprises an amino acid sequence selected from the group consisting of SEQ ID NOs: 19, 20, 21, 22, 23, 24, 25, 26, 27, 28, 29, 30, 37, 40, 42, 43, 44, 45, 46, 47, 49, 50, 51, 62, 63, 64, 65, 66 67, 68, 69, 70, 71, 72, 73, 74, 75, 76, and 77.

* * * * *

SEQUENCE LISTING

```
<160> NUMBER OF SEQ ID NOS: 499

<210> SEQ ID NO 1
<211> LENGTH: 27
<212> TYPE: PRT
<213> ORGANISM: artificial sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Gln or His
<220> FEATURE:
<221> NAME/KEY: MISC_FEATURE
<222> LOCATION: (3)..(3)
<223> OTHER INFORMATION: Gln, Arg, His or Lys
<220> FEATURE:
<221> NAME/KEY: MISC_FEATURE
<222> LOCATION: (3)..(3)
<223> OTHER INFORMATION: Optionally present
<220> FEATURE:
<221> NAME/KEY: MISC_FEATURE
<222> LOCATION: (5)..(5)
<223> OTHER INFORMATION: Gln, His, Lys, Arg, or Glu
<220> FEATURE:
<221> NAME/KEY: MISC_FEATURE
<222> LOCATION: (6)..(6)
<223> OTHER INFORMATION: Trp or Phe
<220> FEATURE:
<221> NAME/KEY: MISC_FEATURE
```

```
<222> LOCATION: (7)..(7)
<223> OTHER INFORMATION: Gln, His, Lys, Arg or Glu
<220> FEATURE:
<221> NAME/KEY: MISC_FEATURE
<222> LOCATION: (8)..(11)
<223> OTHER INFORMATION: optionally present
<220> FEATURE:
<221> NAME/KEY: MISC_FEATURE
<222> LOCATION: (9)..(9)
<223> OTHER INFORMATION: Gln, His, Lys, Arg, or Glu
<220> FEATURE:
<221> NAME/KEY: MISC_FEATURE
<222> LOCATION: (10)..(10)
<223> OTHER INFORMATION: Trp or Phe
<220> FEATURE:
<221> NAME/KEY: MISC_FEATURE
<222> LOCATION: (11)..(11)
<223> OTHER INFORMATION: Gln, His, Lys, Arg or Glu
<220> FEATURE:
<221> NAME/KEY: MISC_FEATURE
<222> LOCATION: (12)..(15)
<223> OTHER INFORMATION: optionally present
<220> FEATURE:
<221> NAME/KEY: MISC_FEATURE
<222> LOCATION: (13)..(13)
<223> OTHER INFORMATION: Gln, His, Lys, Arg, or Glu
<220> FEATURE:
<221> NAME/KEY: MISC_FEATURE
<222> LOCATION: (14)..(14)
<223> OTHER INFORMATION: Trp or Phe
<220> FEATURE:
<221> NAME/KEY: MISC_FEATURE
<222> LOCATION: (15)..(15)
<223> OTHER INFORMATION: Gln, His, Lys, Arg or Glu
<220> FEATURE:
<221> NAME/KEY: MISC_FEATURE
<222> LOCATION: (16)..(19)
<223> OTHER INFORMATION: optionally present
<220> FEATURE:
<221> NAME/KEY: MISC_FEATURE
<222> LOCATION: (17)..(17)
<223> OTHER INFORMATION: Gln, His, Lys, Arg, or Glu
<220> FEATURE:
<221> NAME/KEY: MISC_FEATURE
<222> LOCATION: (18)..(18)
<223> OTHER INFORMATION: Trp or Phe
<220> FEATURE:
<221> NAME/KEY: MISC_FEATURE
<222> LOCATION: (19)..(19)
<223> OTHER INFORMATION: Gln, His, Lys, Arg or Glu
<220> FEATURE:
<221> NAME/KEY: MISC_FEATURE
<222> LOCATION: (20)..(23)
<223> OTHER INFORMATION: optionally present
<220> FEATURE:
<221> NAME/KEY: MISC_FEATURE
<222> LOCATION: (21)..(21)
<223> OTHER INFORMATION: Gln, His, Lys, Arg, or Glu
<220> FEATURE:
<221> NAME/KEY: MISC_FEATURE
<222> LOCATION: (22)..(22)
<223> OTHER INFORMATION: Trp or Phe
<220> FEATURE:
<221> NAME/KEY: MISC_FEATURE
<222> LOCATION: (23)..(23)
<223> OTHER INFORMATION: Gln, His, Lys, Arg or Glu
<220> FEATURE:
<221> NAME/KEY: MISC_FEATURE
<222> LOCATION: (25)..(25)
<223> OTHER INFORMATION: Glu, Gln, or Arg
<220> FEATURE:
<221> NAME/KEY: MISC_FEATURE
<222> LOCATION: (26)..(26)
<223> OTHER INFORMATION: Gln or Lys
<220> FEATURE:
<221> NAME/KEY: MISC_FEATURE
<222> LOCATION: (26)..(26)
<223> OTHER INFORMATION: optionally present
<220> FEATURE:
```

<221> NAME/KEY: MISC_FEATURE
<222> LOCATION: (27)..(27)
<223> OTHER INFORMATION: optionally present

<400> SEQUENCE: 1

Xaa Gln Xaa Phe Xaa Xaa Xaa Phe Xaa Xaa Xaa Phe Xaa Xaa Xaa Phe
1               5                   10                  15

Xaa Xaa Xaa Phe Xaa Xaa Xaa Phe Xaa Xaa Gln
            20                  25

<210> SEQ ID NO 2
<211> LENGTH: 17
<212> TYPE: PRT
<213> ORGANISM: artificial sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Gln or His
<220> FEATURE:
<221> NAME/KEY: MISC_FEATURE
<222> LOCATION: (3)..(3)
<223> OTHER INFORMATION: Asp, Glu, Gln, His, Lys or Arg
<220> FEATURE:
<221> NAME/KEY: MISC_FEATURE
<222> LOCATION: (4)..(4)
<223> OTHER INFORMATION: Trp or Phe
<220> FEATURE:
<221> NAME/KEY: MISC_FEATURE
<222> LOCATION: (5)..(5)
<223> OTHER INFORMATION: Asp, Glu, Gln, His, Lys or Arg
<220> FEATURE:
<221> NAME/KEY: MISC_FEATURE
<222> LOCATION: (6)..(7)
<223> OTHER INFORMATION: optionally present
<220> FEATURE:
<221> NAME/KEY: MISC_FEATURE
<222> LOCATION: (6)..(6)
<223> OTHER INFORMATION: Trp or Phe
<220> FEATURE:
<221> NAME/KEY: MISC_FEATURE
<222> LOCATION: (7)..(7)
<223> OTHER INFORMATION: Asp, Glu, Gln, His, Lys or Arg
<220> FEATURE:
<221> NAME/KEY: MISC_FEATURE
<222> LOCATION: (8)..(9)
<223> OTHER INFORMATION: optionally present
<220> FEATURE:
<221> NAME/KEY: MISC_FEATURE
<222> LOCATION: (8)..(8)
<223> OTHER INFORMATION: Trp or Phe
<220> FEATURE:
<221> NAME/KEY: MISC_FEATURE
<222> LOCATION: (9)..(9)
<223> OTHER INFORMATION: Asp, Glu, Gln, His, Lys or Arg
<220> FEATURE:
<221> NAME/KEY: MISC_FEATURE
<222> LOCATION: (10)..(11)
<223> OTHER INFORMATION: optionally present
<220> FEATURE:
<221> NAME/KEY: MISC_FEATURE
<222> LOCATION: (10)..(10)
<223> OTHER INFORMATION: Trp or Phe
<220> FEATURE:
<221> NAME/KEY: MISC_FEATURE
<222> LOCATION: (11)..(11)
<223> OTHER INFORMATION: Asp, Glu, Gln, His, Lys or Arg
<220> FEATURE:
<221> NAME/KEY: MISC_FEATURE
<222> LOCATION: (12)..(13)
<223> OTHER INFORMATION: optionally present
<220> FEATURE:
<221> NAME/KEY: MISC_FEATURE
<222> LOCATION: (12)..(12)
<223> OTHER INFORMATION: Trp or Phe

```
<220> FEATURE:
<221> NAME/KEY: MISC_FEATURE
<222> LOCATION: (13)..(13)
<223> OTHER INFORMATION: Asp, Glu, Gln, His, Lys or Arg
<220> FEATURE:
<221> NAME/KEY: MISC_FEATURE
<222> LOCATION: (15)..(17)
<223> OTHER INFORMATION: optionally present

<400> SEQUENCE: 2

Xaa Gln Xaa Xaa Xaa Xaa Xaa Xaa Xaa Xaa Xaa Xaa Xaa Phe Glu Gln
1               5                   10                  15

Gln

<210> SEQ ID NO 3
<211> LENGTH: 168
<212> TYPE: DNA
<213> ORGANISM: Artificial Sequence
<220> FEATURE:
<223> OTHER INFORMATION: Synthetic Construct   IBT187.1

<400> SEQUENCE: 3
atgcagcaga aatttaaatg gaaatttcag cagcagccgc gcggccagca gaaatttaaa      60
tggaaatttc agcagcagcc gcgcggccag cagaaattta atggaaatt tcagcagcag     120 ccggaaggcc agcagaaatt taaatggaaa tttcagaagc agtgataa                   168

<210> SEQ ID NO 4
<211> LENGTH: 54
<212> TYPE: PRT
<213> ORGANISM: Artificial Sequence
<220> FEATURE:
<223> OTHER INFORMATION: Synthetic Construct   IBT187.1

<400> SEQUENCE: 4

Met Gln Gln Lys Phe Lys Trp Lys Phe Gln Gln Gln Pro Arg Gly Gln
1               5                   10                  15

Gln Lys Phe Lys Trp Lys Phe Gln Gln Gln Pro Arg Gly Gln Gln Lys
            20                  25                  30

Phe Lys Trp Lys Phe Gln Gln Gln Pro Glu Gly Gln Gln Lys Phe Lys
        35                  40                  45

Trp Lys Phe Gln Lys Gln
    50

<210> SEQ ID NO 5
<211> LENGTH: 270
<212> TYPE: DNA
<213> ORGANISM: Artificial Sequence
<220> FEATURE:
<223> OTHER INFORMATION: Synthetic Construct

<400> SEQUENCE: 5
ccgtctgctc agtctcagct gccggacaaa cattctggcc tgcacgagcg tgctccgcag      60
cgttacggtc cggaaccgga gccggagccg gaaccaatcc ctgaaccacc gaaagaggct     120
ccggtagtga ttgagaaacc taaaccgaaa ccaaagccga agccgaaacc gccggctcac     180
gatcataaga accagaaaga gacgcaccag cgtcacgctg cgggttctgg tggtggcggt     240
tcccctcacc accaccatca ccactgataa                                      270

<210> SEQ ID NO 6
<211> LENGTH: 88
<212> TYPE: PRT
<213> ORGANISM: Artificial Sequence
```

<220> FEATURE:
<223> OTHER INFORMATION: Synthetic Construct HC263

<400> SEQUENCE: 6

```
Pro Ser Ala Gln Ser Gln Leu Pro Asp Lys His Ser Gly Leu His Glu
1               5                   10                  15

Arg Ala Pro Gln Arg Tyr Gly Pro Glu Pro Glu Pro Glu Pro
            20                  25                  30

Ile Pro Glu Pro Pro Lys Glu Ala Pro Val Val Ile Glu Lys Pro Lys
        35                  40                  45

Pro Lys Pro Lys Pro Lys Pro Lys Pro Pro Ala His Asp His Lys Asn
    50                  55                  60

Gln Lys Glu Thr His Gln Arg His Ala Ala Gly Ser Gly Gly Gly Gly
65                  70                  75                  80

Ser Pro His His His His His His
                85
```

<210> SEQ ID NO 7
<211> LENGTH: 399
<212> TYPE: DNA
<213> ORGANISM: Artificial Sequence
<220> FEATURE:
<223> OTHER INFORMATION: Synthetic Construct IBT187.HC263

<400> SEQUENCE: 7

```
atgcagcaga aatttaaatg gaaatttcag cagcagccgc gcggccagca gaaatttaaa      60
tggaaatttc agcagcagcc ggaaggccag cagaaattta atggaaattt cagcagcag     120
ggatccgacc cgtctgctca gtctcagctg ccggacaaac attctggcct gcacgagcgt    180
gctccgcagc gttacggtcc ggaaccggag ccggagccgg aaccaatccc tgaaccaccg    240
aaagaggctc cggtagtgat tgagaaacct aaaccgaaac caaagccgaa gccgaaaccg    300
ccggctcacg atcataagaa ccagaaagag acgcaccagc gtcacgctgc gggttctggt    360
ggtggcggtt cccctcacca ccaccatcac cactgataa                           399
```

<210> SEQ ID NO 8
<211> LENGTH: 131
<212> TYPE: PRT
<213> ORGANISM: Artificial Sequence
<220> FEATURE:
<223> OTHER INFORMATION: Synthetic Construct, IBT187.HC263

<400> SEQUENCE: 8

```
Met Gln Gln Lys Phe Lys Trp Lys Phe Gln Gln Gln Pro Arg Gly Gln
1               5                   10                  15

Gln Lys Phe Lys Trp Lys Phe Gln Gln Gln Pro Glu Gly Gln Gln Lys
            20                  25                  30

Phe Lys Trp Lys Phe Gln Gln Gln Gly Ser Asp Pro Ser Ala Gln Ser
        35                  40                  45

Gln Leu Pro Asp Lys His Ser Gly Leu His Glu Arg Ala Pro Gln Arg
    50                  55                  60

Tyr Gly Pro Glu Pro Glu Pro Glu Pro Glu Pro Ile Pro Glu Pro Pro
65                  70                  75                  80

Lys Glu Ala Pro Val Val Ile Glu Lys Pro Lys Pro Lys Pro Lys Pro
                85                  90                  95

Lys Pro Lys Pro Pro Ala His Asp His Lys Asn Gln Lys Glu Thr His
            100                 105                 110

Gln Arg His Ala Ala Gly Ser Gly Gly Gly Gly Ser Pro His His His
```

His His His
    130

<210> SEQ ID NO 9
<211> LENGTH: 381
<212> TYPE: DNA
<213> ORGANISM: Artificial Sequence
<220> FEATURE:
<223> OTHER INFORMATION: Synthetic Construct IBT187.H2-TonB.G3

<400> SEQUENCE: 9

| | |
|---|---|
| atgcagcaga aatttaaatg gaaatttcag cagcagccgc gcggccagca gaaatttaaa | 60 |
| tggaaatttc agcagcagcc ggaaggccag cagaaattta atggaaattt cagcagcag | 120 |
| ggatccgatc catctgaggg ctccgaatct ggtgcacagt ctcagctgcc tgacaagcac | 180 |
| agcggcctgc acgagcgtgc tccgcagcgt tacggtccgg agccggaacc ggagcctgaa | 240 |
| ccgattccgg agccgccgaa agaagcccca gtggttattg aaaaaccgaa accgaagccg | 300 |
| aaaccaaaac ctaaaccacc ggcccatgac acaagaacca gaaagaaac ccaccagcgt | 360 |
| cacgcggctg gcggcggtta a | 381 |

<210> SEQ ID NO 10
<211> LENGTH: 126
<212> TYPE: PRT
<213> ORGANISM: Artificial Sequence
<220> FEATURE:
<223> OTHER INFORMATION: Synthetic Construct IBT187.H2-TonB-G3

<400> SEQUENCE: 10

Met Gln Gln Lys Phe Lys Trp Lys Phe Gln Gln Gln Pro Arg Gly Gln
1               5                   10                  15

Gln Lys Phe Lys Trp Lys Phe Gln Gln Gln Pro Glu Gly Gln Gln Lys
            20                  25                  30

Phe Lys Trp Lys Phe Gln Gln Gln Gly Ser Asp Pro Ser Glu Gly Ser
        35                  40                  45

Glu Ser Gly Ala Gln Ser Gln Leu Pro Asp Lys His Ser Gly Leu His
    50                  55                  60

Glu Arg Ala Pro Gln Arg Tyr Gly Pro Glu Pro Glu Pro Glu Pro Glu
65                  70                  75                  80

Pro Ile Pro Glu Pro Pro Lys Glu Ala Pro Val Val Ile Glu Lys Pro
                85                  90                  95

Lys Pro Lys Pro Lys Pro Lys Pro Lys Pro Pro Ala His Asp His Lys
            100                 105                 110

Asn Gln Lys Glu Thr His Gln Arg His Ala Ala Gly Gly Gly
        115                 120                 125

<210> SEQ ID NO 11
<211> LENGTH: 174
<212> TYPE: DNA
<213> ORGANISM: Artificial Sequence
<220> FEATURE:
<223> OTHER INFORMATION: Synthetic Construct IBT233

<400> SEQUENCE: 11

| | |
|---|---|
| atggcgagcc accaacactt tcactggcaa ttcgagcaac agccacgcgg tcatcagcat | 60 |
| tttcattggc agttcgagca gcagccgcgt ggccaccagc acttccactg gcagtttgaa | 120 |
| caacagccgg agggtcatca acattttcac tggcaattcg acaacaggg atcc | 174 |

<210> SEQ ID NO 12
<211> LENGTH: 447
<212> TYPE: DNA
<213> ORGANISM: Artificial Sequence
<220> FEATURE:
<223> OTHER INFORMATION: Synthetic Construct IBT233.HC263

<400> SEQUENCE: 12

```
atggcgagcc accaacactt tcactggcaa ttcgagcaac agccacgcgg tcatcagcat    60
tttcattggc agttcgagca gcagccgcgt ggccaccagc acttccactg gcagtttgaa   120
caacagccgg agggtcatca acattttcac tggcaattcg aacaacaggg atccgacccg   180
tctgctcagt ctcagctgcc ggacaaacat tctggcctgc acgagcgtgc tccgcagcgt   240
tacggtccgg aaccggagcc ggagccggaa ccaatccctg aaccaccgaa agaggctccg   300
gtagtgattg agaaacctaa accgaaacca aagccgaagc cgaaaccgcc ggctcacgat   360
cataagaacc agaaagagac gcaccagcgt cacgctgcgg ttctggtgg tggcggttcc   420 cctcaccacc accatcacca ctgataa                                       447
```

<210> SEQ ID NO 13
<211> LENGTH: 147
<212> TYPE: PRT
<213> ORGANISM: Artificial Sequence
<220> FEATURE:
<223> OTHER INFORMATION: Synthetic Construct

<400> SEQUENCE: 13

```
Met Ala Ser His Gln His Phe His Trp Gln Phe Glu Gln Gln Pro Arg
1               5                   10                  15

Gly His Gln His Phe His Trp Gln Phe Glu Gln Gln Pro Arg Gly His
            20                  25                  30

Gln His Phe His Trp Gln Phe Glu Gln Gln Pro Glu Gly His Gln His
        35                  40                  45

Phe His Trp Gln Phe Glu Gln Gln Gly Ser Asp Pro Ser Ala Gln Ser
    50                  55                  60

Gln Leu Pro Asp Lys His Ser Gly Leu His Glu Arg Ala Pro Gln Arg
65                  70                  75                  80

Tyr Gly Pro Glu Pro Glu Pro Glu Pro Ile Pro Glu Pro Pro
                85                  90                  95

Lys Glu Ala Pro Val Val Ile Glu Lys Pro Lys Pro Lys Pro Lys Pro
                100                 105                 110

Lys Pro Lys Pro Pro Ala His Asp His Lys Asn Gln Lys Glu Thr His
            115                 120                 125

Gln Arg His Ala Ala Gly Ser Gly Gly Gly Ser Pro His His His
        130                 135                 140

His His His
145
```

<210> SEQ ID NO 14
<211> LENGTH: 58
<212> TYPE: PRT
<213> ORGANISM: Artificial Sequence
<220> FEATURE:
<223> OTHER INFORMATION: Synthetic Construct IBT139

<400> SEQUENCE: 14

```
Met Gln Gln Arg Phe Gln Trp Gln Phe Glu Gln Gln Pro Arg Gly Gln
1               5                   10                  15
```

Gln Arg Phe Gln Trp Gln Phe Glu Gln Gln Pro Arg Gly Gln Arg
            20                  25                  30

Phe Gln Trp Gln Phe Glu Gln Gln Pro Glu Gly Gln Gln Arg Phe Gln
        35                  40                  45

Trp Gln Phe Glu Gln Gln Gly Ser Asp Pro
    50                  55

<210> SEQ ID NO 15
<211> LENGTH: 48
<212> TYPE: PRT
<213> ORGANISM: Artificial Sequence
<220> FEATURE:
<223> OTHER INFORMATION: Synthetic Construct IBT201

<400> SEQUENCE: 15

Met Ala Ser Gln Gln Arg Phe Gln Trp Gln Phe Gln Gln Pro Arg
1               5                   10                  15

Gly Gln Gln Arg Phe Gln Trp Gln Phe Gln Gln Pro Glu Gly Gln
            20                  25                  30

Gln Arg Phe Gln Trp Gln Phe Gln Gln Gly Pro Gly Ser Asp Pro
        35                  40                  45

<210> SEQ ID NO 16
<211> LENGTH: 62
<212> TYPE: PRT
<213> ORGANISM: Artificial Sequence
<220> FEATURE:
<223> OTHER INFORMATION: Synthetic Construct IBT202

<400> SEQUENCE: 16

Met Ala Ser Gln Gln Arg Phe Gln Trp Gln Phe Gln Gln Gln Pro Arg
1               5                   10                  15

Gly Gln Gln Arg Phe Gln Trp Gln Phe Gln Gln Gln Pro Arg Gly Gln
            20                  25                  30

Gln Arg Phe Gln Trp Gln Phe Gln Gln Gln Pro Glu Gly Gln Gln Arg
        35                  40                  45

Phe Gln Trp Gln Phe Gln Gln Gln Gly Pro Gly Ser Asp Pro
    50                  55                  60

<210> SEQ ID NO 17
<211> LENGTH: 62
<212> TYPE: PRT
<213> ORGANISM: Artificial Sequence
<220> FEATURE:
<223> OTHER INFORMATION: Synthetic Construct IBT203

<400> SEQUENCE: 17

Met Ala Ser Gln Gln Arg Phe Gln Trp Gln Phe Gln Gln Gln Pro Arg
1               5                   10                  15

Gly Gln Gln Arg Phe Gln Trp Gln Phe Gln Gln Pro Glu Gly Gln
            20                  25                  30

Gln Arg Phe Gln Trp Gln Phe Gln Gln Gln Gly Pro Gly Ser Gly Gly
        35                  40                  45

Ala Gly Ser Pro Gly Ser Ala Gly Gly Pro Gly Ser Asp Pro
    50                  55                  60

<210> SEQ ID NO 18
<211> LENGTH: 76
<212> TYPE: PRT
<213> ORGANISM: Artificial Sequence
<220> FEATURE:
<223> OTHER INFORMATION: Synthetic Construct IBT204

```
<400> SEQUENCE: 18

Met Ala Ser Gln Gln Arg Phe Gln Trp Gln Phe Gln Gln Pro Arg
1               5                   10                  15

Gly Gln Gln Arg Phe Gln Trp Gln Phe Gln Gln Pro Arg Gly Gln
                20                  25                  30

Gln Arg Phe Gln Trp Gln Phe Gln Gln Pro Glu Gly Gln Gln Arg
            35                  40                  45

Phe Gln Trp Gln Phe Gln Gln Gly Pro Gly Ser Gly Gly Ala Gly
        50                  55                  60

Ser Pro Gly Ser Ala Gly Gly Pro Gly Ser Asp Pro
65                  70                  75

<210> SEQ ID NO 19
<211> LENGTH: 62
<212> TYPE: PRT
<213> ORGANISM: Artificial Sequence
<220> FEATURE:
<223> OTHER INFORMATION: Synthetic Construct  IBT205

<400> SEQUENCE: 19

Met Ala Ser Gln Gln Arg Phe Gln Trp Gln Phe Arg Gln Gln Pro Arg
1               5                   10                  15

Gly Gln Gln Gln Phe Arg Trp Gln Phe Gln Gln Pro Glu Gly Gln
                20                  25                  30

Gln Arg Phe Gln Trp Gln Phe Arg Gln Gln Gly Pro Gly Ser Gly Gly
            35                  40                  45

Ala Gly Ser Pro Gly Ser Ala Gly Gly Pro Gly Ser Asp Pro
        50                  55                  60

<210> SEQ ID NO 20
<211> LENGTH: 62
<212> TYPE: PRT
<213> ORGANISM: Artificial Sequence
<220> FEATURE:
<223> OTHER INFORMATION: Synthetic Construct  IBT206

<400> SEQUENCE: 20

Met Ala Ser Gln Gln Gln Phe Arg Trp Gln Phe Gln Gln Pro Arg
1               5                   10                  15

Gly Gln Gln Arg Phe Gln Trp Gln Phe Arg Gln Pro Glu Gly Gln
                20                  25                  30

Gln Gln Phe Gln Trp Arg Phe Gln Gln Gln Gly Pro Gly Ser Gly Gly
            35                  40                  45

Ala Gly Ser Pro Gly Ser Ala Gly Gly Pro Gly Ser Asp Pro
        50                  55                  60

<210> SEQ ID NO 21
<211> LENGTH: 62
<212> TYPE: PRT
<213> ORGANISM: Artificial Sequence
<220> FEATURE:
<223> OTHER INFORMATION: Synthetic Construct  IBT207

<400> SEQUENCE: 21

Met Ala Ser Gln Gln Arg Phe Arg Trp Arg Phe Gln Gln Gln Pro Arg
1               5                   10                  15

Gly Gln Gln Arg Phe Glu Trp Glu Phe Gln Gln Pro Arg Gly Gln
                20                  25                  30

Gln Arg Phe Arg Trp Arg Phe Gln Gln Gln Pro Glu Gly Gln Gln Arg
```

Phe Glu Trp Glu Phe Gln Gln Gln Gly Pro Gly Ser Asp Pro
    50                  55                  60

<210> SEQ ID NO 22
<211> LENGTH: 76
<212> TYPE: PRT
<213> ORGANISM: Artificial Sequence
<220> FEATURE:
<223> OTHER INFORMATION: Synthetic Construct IBT208

<400> SEQUENCE: 22

Met Ala Ser Gln Gln Arg Phe Arg Trp Arg Phe Gln Gln Gln Pro Arg
1               5                   10                  15

Gly Gln Gln Arg Phe Glu Trp Glu Phe Gln Gln Gln Pro Arg Gly Gln
                20                  25                  30

Gln Arg Phe Arg Trp Arg Phe Gln Gln Gln Pro Glu Gly Gln Gln Arg
            35                  40                  45

Phe Glu Trp Glu Phe Gln Gln Gln Gly Pro Gly Ser Gly Gly Ala Gly
    50                  55                  60

Ser Pro Gly Ser Ala Gly Gly Pro Gly Ser Asp Pro
65                  70                  75

<210> SEQ ID NO 23
<211> LENGTH: 60
<212> TYPE: PRT
<213> ORGANISM: Artificial Sequence
<220> FEATURE:
<223> OTHER INFORMATION: Synthetic Construct IBT209

<400> SEQUENCE: 23

Met Ala Ser Gln Gln Arg Phe Gln Trp Gln Phe Gln Trp Gln Phe Glu
1               5                   10                  15

Gln Gln Pro Arg Gly Gln Gln Arg Phe Gln Trp Gln Phe Gln Trp Gln
                20                  25                  30

Phe Glu Gln Gln Pro Glu Gly Gln Gln Arg Phe Gln Trp Gln Phe Gln
            35                  40                  45

Trp Gln Phe Glu Gln Gln Gly Pro Gly Ser Asp Pro
    50                  55                  60

<210> SEQ ID NO 24
<211> LENGTH: 74
<212> TYPE: PRT
<213> ORGANISM: Artificial Sequence
<220> FEATURE:
<223> OTHER INFORMATION: Synthetic Construct IBT210

<400> SEQUENCE: 24

Met Ala Ser Gln Gln Arg Phe Gln Trp Gln Phe Gln Trp Gln Phe Glu
1               5                   10                  15

Gln Gln Pro Arg Gly Gln Gln Arg Phe Gln Trp Gln Phe Gln Trp Gln
                20                  25                  30

Phe Glu Gln Gln Pro Glu Gly Gln Gln Arg Phe Gln Trp Gln Phe Gln
            35                  40                  45

Trp Gln Phe Glu Gln Gln Gly Pro Gly Ser Gly Gly Ala Gly Ser Pro
    50                  55                  60

Gly Ser Ala Gly Gly Pro Gly Ser Asp Pro
65                  70

<210> SEQ ID NO 25

<211> LENGTH: 74
<212> TYPE: PRT
<213> ORGANISM: Artificial Sequence
<220> FEATURE:
<223> OTHER INFORMATION: Synthetic Construct IBT212

<400> SEQUENCE: 25

Met Ala Ser Gln Gln Arg Phe Arg Trp Gln Phe Gln Trp Gln Phe Glu
1               5                   10                  15

Gln Gln Pro Arg Gly Gln Gln Arg Phe Arg Trp Gln Phe Gln Trp Gln
            20                  25                  30

Phe Glu Gln Gln Pro Glu Gly Gln Gln Arg Phe Arg Trp Gln Phe Gln
        35                  40                  45

Trp Gln Phe Glu Gln Gln Gly Pro Gly Ser Gly Gly Ala Gly Ser Pro
    50                  55                  60

Gly Ser Ala Gly Gly Pro Gly Ser Asp Pro
65                  70

<210> SEQ ID NO 26
<211> LENGTH: 74
<212> TYPE: PRT
<213> ORGANISM: Artificial Sequence
<220> FEATURE:
<223> OTHER INFORMATION: Synthetic Construct IBT214

<400> SEQUENCE: 26

Met Ala Ser Gln Gln Arg Phe Arg Trp Gln Phe Arg Trp Gln Phe Glu
1               5                   10                  15

Gln Gln Pro Arg Gly Gln Gln Arg Phe Gln Trp Gln Phe Arg Trp Gln
            20                  25                  30

Phe Glu Gln Gln Pro Glu Gly Gln Gln Arg Phe Arg Trp Gln Phe Arg
        35                  40                  45

Trp Gln Phe Glu Gln Gln Gly Pro Gly Ser Gly Gly Ala Gly Ser Pro
    50                  55                  60

Gly Ser Ala Gly Gly Pro Gly Ser Asp Pro
65                  70

<210> SEQ ID NO 27
<211> LENGTH: 74
<212> TYPE: PRT
<213> ORGANISM: Artificial Sequence
<220> FEATURE:
<223> OTHER INFORMATION: Synthetic Construct IBT216

<400> SEQUENCE: 27

Met Ala Ser Gln Gln Arg Phe Gln Trp Gln Phe Arg Trp Gln Phe Glu
1               5                   10                  15

Gln Gln Pro Arg Gly Gln Gln Arg Phe Arg Trp Gln Phe Arg Trp Gln
            20                  25                  30

Phe Glu Gln Gln Pro Glu Gly Gln Gln Arg Phe Gln Trp Gln Phe Arg
        35                  40                  45

Trp Gln Phe Glu Gln Gln Gly Pro Gly Ser Gly Gly Ala Gly Ser Pro
    50                  55                  60

Gly Ser Ala Gly Gly Pro Gly Ser Asp Pro
65                  70

<210> SEQ ID NO 28
<211> LENGTH: 68
<212> TYPE: PRT
<213> ORGANISM: Artificial Sequence
<220> FEATURE:

-continued

<223> OTHER INFORMATION: Synthetic Construct IBT218

<400> SEQUENCE: 28

```
Met Ala Ser Gln Gln Arg Phe Gln Phe Gln Phe Glu Gln Gln
1               5                   10                  15

Pro Arg Gly Gln Gln Arg Phe Gln Phe Gln Phe Glu Gln Gln
            20                  25                  30

Pro Glu Gly Gln Gln Arg Phe Gln Phe Gln Phe Glu Gln Gln
        35                  40                  45

Gly Pro Gly Ser Gly Gly Ala Gly Ser Pro Gly Ser Ala Gly Gly Pro
    50                  55                  60

Gly Ser Asp Pro
65
```

<210> SEQ ID NO 29
<211> LENGTH: 68
<212> TYPE: PRT
<213> ORGANISM: Artificial Sequence
<220> FEATURE:
<223> OTHER INFORMATION: Synthetic Construct IBT220

<400> SEQUENCE: 29

```
Met Ala Ser Gln Gln Arg Phe Arg Phe Arg Phe Gln Phe Glu Gln Gln
1               5                   10                  15

Pro Arg Gly Gln Gln Arg Phe Arg Phe Gln Phe Gln Phe Glu Gln Gln
            20                  25                  30

Pro Glu Gly Gln Gln Arg Phe Arg Phe Arg Phe Gln Phe Glu Gln Gln
        35                  40                  45

Gly Pro Gly Ser Gly Gly Ala Gly Ser Pro Gly Ser Ala Gly Gly Pro
    50                  55                  60

Gly Ser Asp Pro
65
```

<210> SEQ ID NO 30
<211> LENGTH: 68
<212> TYPE: PRT
<213> ORGANISM: Artificial Sequence
<220> FEATURE:
<223> OTHER INFORMATION: Synthetic Construct IBT222

<400> SEQUENCE: 30

```
Met Ala Ser Gln Gln Arg Phe Arg Phe Gln Phe Gln Phe Glu Gln Gln
1               5                   10                  15

Pro Arg Gly Gln Gln Arg Phe Arg Phe Arg Phe Gln Phe Glu Gln Gln
            20                  25                  30

Pro Glu Gly Gln Gln Arg Phe Arg Phe Gln Phe Gln Phe Glu Gln Gln
        35                  40                  45

Gly Pro Gly Ser Gly Gly Ala Gly Ser Pro Gly Ser Ala Gly Gly Pro
    50                  55                  60

Gly Ser Asp Pro
65
```

<210> SEQ ID NO 31
<211> LENGTH: 60
<212> TYPE: PRT
<213> ORGANISM: Artificial Sequence
<220> FEATURE:
<223> OTHER INFORMATION: Synthetic Construct IBT223

<400> SEQUENCE: 31

```
Met Ala Ser Gln Gln Arg Phe Gln Trp Gln Phe Glu Gln Gln Pro Arg
1               5                   10                  15

Gly Gln Gln Arg Phe Gln Trp Gln Phe Glu Gln Pro Arg Gly Gln
                20                  25                  30

Gln Arg Phe Gln Trp Gln Phe Glu Gln Gln Pro Glu Gly Gln Arg
            35                  40                  45

Phe Gln Trp Gln Phe Glu Gln Gln Gly Ser Asp Pro
        50                  55                  60
```

<210> SEQ ID NO 32
<211> LENGTH: 62
<212> TYPE: PRT
<213> ORGANISM: Artificial Sequence
<220> FEATURE:
<223> OTHER INFORMATION: Synthetic Construct IBT224

<400> SEQUENCE: 32

```
Met Ala Ser Gln Gln Arg Phe Gln Trp Gln Phe Gln Gln Gln Pro Arg
1               5                   10                  15

Gly Gln Gln Arg Phe Gln Trp Gln Phe Gln Gln Gln Pro Arg Gly Gln
                20                  25                  30

Gln Arg Phe Gln Trp Gln Phe Gln Gln Gln Pro Glu Gly Gln Gln Arg
            35                  40                  45

Phe Gln Trp Gln Phe Gln Gln Gly Ser Gly Ser Asp Pro
        50                  55                  60
```

<210> SEQ ID NO 33
<211> LENGTH: 78
<212> TYPE: PRT
<213> ORGANISM: Artificial Sequence
<220> FEATURE:
<223> OTHER INFORMATION: Synthetic Construct IBT225

<400> SEQUENCE: 33

```
Met Ala Ser Gln Gln Arg Phe Gln Trp Gln Phe Gln Gln Gln Pro Arg
1               5                   10                  15

Gly Gln Gln Arg Phe Gln Trp Gln Phe Gln Gln Pro Arg Gly Gln
                20                  25                  30

Gln Arg Phe Gln Trp Gln Phe Gln Gln Pro Glu Gly Gln Gln Arg
            35                  40                  45

Phe Gln Trp Gln Phe Gln Gln Gly Pro Gly Ser Gly Gly Ala Gly
        50                  55                  60

Ser Pro Gly Ser Ala Gly Gly Pro Gly Ser Gly Ser Asp Pro
65                  70                  75
```

<210> SEQ ID NO 34
<211> LENGTH: 60
<212> TYPE: PRT
<213> ORGANISM: Artificial Sequence
<220> FEATURE:
<223> OTHER INFORMATION: Synthetic Construct IBT229

<400> SEQUENCE: 34

```
Met Ala Ser Gln Gln His Phe Gln Trp Gln Phe Glu Gln Gln Pro Arg
1               5                   10                  15

Gly Gln Gln His Phe Gln Trp Gln Phe Glu Gln Gln Pro Arg Gly Gln
                20                  25                  30

Gln His Phe Gln Trp Gln Phe Glu Gln Gln Pro Glu Gly Gln Gln His
            35                  40                  45

Phe Gln Trp Gln Phe Glu Gln Gln Gly Ser Asp Pro
```

<210> SEQ ID NO 35
<211> LENGTH: 76
<212> TYPE: PRT
<213> ORGANISM: Artificial Sequence
<220> FEATURE:
<223> OTHER INFORMATION: Synthetic Construct IBT230

<400> SEQUENCE: 35

Met Ala Ser Gln Gln His Phe Gln Trp Gln Phe Glu Gln Gln Pro Arg
1               5                   10                  15

Gly Gln Gln His Phe Gln Trp Gln Phe Glu Gln Gln Pro Arg Gly Gln
            20                  25                  30

Gln His Phe Gln Trp Gln Phe Glu Gln Gln Pro Glu Gly Gln Gln His
        35                  40                  45

Phe Gln Trp Gln Phe Glu Gln Gln Gly Pro Gly Ser Gly Gly Ala Gly
    50                  55                  60

Ser Pro Gly Ser Ala Gly Gly Pro Gly Ser Asp Pro
65                  70                  75

<210> SEQ ID NO 36
<211> LENGTH: 60
<212> TYPE: PRT
<213> ORGANISM: Artificial Sequence
<220> FEATURE:
<223> OTHER INFORMATION: Synthetic Construct IBT232

<400> SEQUENCE: 36

Met Ala Ser Gln Gln His Phe His Trp Gln Phe Glu Gln Gln Pro Arg
1               5                   10                  15

Gly Gln Gln His Phe His Trp Gln Phe Glu Gln Gln Pro Arg Gly Gln
            20                  25                  30

Gln His Phe His Trp Gln Phe Glu Gln Gln Pro Glu Gly Gln Gln His
        35                  40                  45

Phe His Trp Gln Phe Glu Gln Gln Gly Ser Asp Pro
    50                  55                  60

<210> SEQ ID NO 37
<211> LENGTH: 58
<212> TYPE: PRT
<213> ORGANISM: Artificial Sequence
<220> FEATURE:
<223> OTHER INFORMATION: Synthetic Construct IBT233

<400> SEQUENCE: 37

Met Ala Ser His Gln His Phe His Trp Gln Phe Glu Gln Gln Pro Arg
1               5                   10                  15

Gly His Gln His Phe His Trp Gln Phe Glu Gln Gln Pro Arg Gly His
            20                  25                  30

Gln His Phe His Trp Gln Phe Glu Gln Gln Pro Glu Gly His Gln His
        35                  40                  45

Phe His Trp Gln Phe Glu Gln Gln Gly Ser
    50                  55

<210> SEQ ID NO 38
<211> LENGTH: 76
<212> TYPE: PRT
<213> ORGANISM: Artificial Sequence
<220> FEATURE:
<223> OTHER INFORMATION: Synthetic Construct IBT239

```
<400> SEQUENCE: 38

Met Ala Ser Gln Gln Arg Phe Gln Trp Gln Phe Glu Gln Gln Pro Arg
1               5                   10                  15

Gly Gln Gln Arg Phe Gln Trp Gln Phe Glu Gln Gln Pro Arg Gly Gln
                20                  25                  30

Gln Arg Phe Gln Trp Gln Phe Glu Gln Gln Pro Glu Gln Gln Arg
            35                  40                  45

Phe Gln Trp Gln Phe Glu Gln Gln Gly Pro Gly Ser Gly Gly Ala Gly
        50                  55                  60

Ser Pro Gly Ser Ala Gly Gly Pro Gly Ser Asp Pro
65                  70                  75

<210> SEQ ID NO 39
<211> LENGTH: 76
<212> TYPE: PRT
<213> ORGANISM: Artificial Sequence
<220> FEATURE:
<223> OTHER INFORMATION: Synthetic Construct IBT241

<400> SEQUENCE: 39

Met Ala Ser Gln Gln His Phe His Trp Gln Phe Glu Gln Gln Pro Arg
1               5                   10                  15

Gly Gln Gln His Phe His Trp Gln Phe Glu Gln Gln Pro Arg Gly Gln
                20                  25                  30

Gln His Phe His Trp Gln Phe Glu Gln Gln Pro Glu Gln Gln His
            35                  40                  45

Phe His Trp Gln Phe Glu Gln Gln Gly Pro Gly Ser Gly Gly Ala Gly
        50                  55                  60

Ser Pro Gly Ser Ala Gly Gly Pro Gly Ser Asp Pro
65                  70                  75

<210> SEQ ID NO 40
<211> LENGTH: 76
<212> TYPE: PRT
<213> ORGANISM: Artificial Sequence
<220> FEATURE:
<223> OTHER INFORMATION: Synthetic Construct IBT242

<400> SEQUENCE: 40

Met Ala Ser His Gln His Phe His Trp Gln Phe Glu Gln Gln Pro Arg
1               5                   10                  15

Gly His Gln His Phe His Trp Gln Phe Glu Gln Gln Pro Arg Gly His
                20                  25                  30

Gln His Phe His Trp Gln Phe Glu Gln Gln Pro Glu His Gln His
            35                  40                  45

Phe His Trp Gln Phe Glu Gln Gln Gly Pro Gly Ser Gly Gly Ala Gly
        50                  55                  60

Ser Pro Gly Ser Ala Gly Gly Pro Gly Ser Asp Pro
65                  70                  75

<210> SEQ ID NO 41
<211> LENGTH: 77
<212> TYPE: PRT
<213> ORGANISM: ARTIFICIAL SEQUENCE
<220> FEATURE:
<223> OTHER INFORMATION: synthetic construct IBT247

<400> SEQUENCE: 41

Met Ala Ser Gln Gln His Phe His Trp Gln Phe Glu Gln Gln Pro Arg
1               5                   10                  15
```

Gly Gln Gln His Phe His Trp Gln Phe Glu Gln Gln Pro Arg Gly Gln
                20                  25                  30

Gln His Phe His Trp Gln Phe Glu Gln Gln Pro Arg Gly Gln Gln His
                35                  40                  45

Phe His Trp Gln Phe Glu Gln Gln Pro Arg Arg Gly Pro Gly Ser Gly
    50                  55                  60

Gly Ala Gly Ser Pro Gly Ser Ala Gly Gly Pro Gly Ser
65                  70                  75

<210> SEQ ID NO 42
<211> LENGTH: 77
<212> TYPE: PRT
<213> ORGANISM: ARTIFICIAL SEQUENCE
<220> FEATURE:
<223> OTHER INFORMATION: synthetic construct IBT248

<400> SEQUENCE: 42

Met Ala Ser His Gln His Phe His Trp Gln Phe Glu Gln Gln Pro Arg
1               5                   10                  15

Gly His Gln His Phe His Trp Gln Phe Glu Gln Gln Pro Arg Gly His
                20                  25                  30

Gln His Phe His Trp Gln Phe Glu Gln Gln Pro Arg Gly His Gln His
                35                  40                  45

Phe His Trp Gln Phe Glu Gln Gln Pro Arg Arg Gly Pro Gly Ser Gly
    50                  55                  60

Gly Ala Gly Ser Pro Gly Ser Ala Gly Gly Pro Gly Ser
65                  70                  75

<210> SEQ ID NO 43
<211> LENGTH: 136
<212> TYPE: PRT
<213> ORGANISM: Artificial Sequence
<220> FEATURE:
<223> OTHER INFORMATION: Synthetic Construct IBT249

<400> SEQUENCE: 43

Met Ala Ser Gln Gln Arg Phe Gln Trp Gln Phe Glu Gln Gln Gly Gly
1               5                   10                  15

Ala Gly Gln Gly Gly Leu Gly Ser Gln Gly Ala Gly Gln Gly Ala Gly
                20                  25                  30

Gln Gln Arg Phe Gln Trp Gln Phe Glu Gln Gln Gly Gly Ala Gly Gln
                35                  40                  45

Gly Gly Tyr Gly Gly Leu Gly Ser Gln Gly Ala Gly Arg Gly Gly Gln
    50                  55                  60

Gly Ala Gly Gln Gln Arg Phe Gln Trp Gln Phe Glu Gln Gln Gly Gly
65                  70                  75                  80

Ala Gly Gln Gly Gly Tyr Gly Gly Leu Gly Ser Gln Gly Ala Gly Arg
                85                  90                  95

Gly Gly Leu Gly Gly Gln Gly Ala Gly Gln Gln Arg Phe Gln Trp Gln
                100                 105                 110

Phe Glu Gln Gln Gly Pro Gly Ser Gly Gly Ala Gly Ser Pro Gly Ser
        115                 120                 125

Ala Gly Gly Pro Gly Ser Asp Pro
        130                 135

<210> SEQ ID NO 44
<211> LENGTH: 136
<212> TYPE: PRT

```
<213> ORGANISM: Artificial Sequence
<220> FEATURE:
<223> OTHER INFORMATION: Synthetic Construct IBT254

<400> SEQUENCE: 44

Met Ala Ser Gln Gln His Phe His Trp Gln Phe Glu Gln Gln Gly Gly
1               5                   10                  15

Ala Gly Gln Gly Gly Leu Gly Ser Gln Gly Ala Gly Gln Gly Ala Gly
            20                  25                  30

Gln Gln His Phe His Trp Gln Phe Glu Gln Gln Gly Gly Ala Gly Gln
        35                  40                  45

Gly Gly Tyr Gly Gly Leu Gly Ser Gln Gly Ala Gly Arg Gly Gly Gln
    50                  55                  60

Gly Ala Gly Gln Gln His Phe His Trp Gln Phe Glu Gln Gln Gly Gly
65                  70                  75                  80

Ala Gly Gln Gly Gly Tyr Gly Gly Leu Gly Ser Gln Gly Ala Gly Arg
                85                  90                  95

Gly Gly Leu Gly Gly Gln Gly Ala Gly Gln Gln His Phe His Trp Gln
            100                 105                 110

Phe Glu Gln Gln Gly Pro Gly Ser Gly Gly Ala Gly Ser Pro Gly Ser
        115                 120                 125

Ala Gly Gly Pro Gly Ser Asp Pro
    130                 135

<210> SEQ ID NO 45
<211> LENGTH: 136
<212> TYPE: PRT
<213> ORGANISM: Artificial Sequence
<220> FEATURE:
<223> OTHER INFORMATION: Synthetic Construct IBT255

<400> SEQUENCE: 45

Met Ala Ser His Gln His Phe His Trp Gln Phe Glu Gln Gln Gly Gly
1               5                   10                  15

Ala Gly Gln Gly Gly Leu Gly Ser Gln Gly Ala Gly Gln Gly Ala Gly
            20                  25                  30

His Gln His Phe His Trp Gln Phe Glu Gln Gln Gly Gly Ala Gly Gln
        35                  40                  45

Gly Gly Tyr Gly Gly Leu Gly Ser Gln Gly Ala Gly Arg Gly Gly Gln
    50                  55                  60

Gly Ala Gly His Gln His Phe His Trp Gln Phe Glu Gln Gln Gly Gly
65                  70                  75                  80

Ala Gly Gln Gly Gly Tyr Gly Gly Leu Gly Ser Gln Gly Ala Gly Arg
                85                  90                  95

Gly Gly Leu Gly Gly Gln Gly Ala Gly His Gln His Phe His Trp Gln
            100                 105                 110

Phe Glu Gln Gln Gly Pro Gly Ser Gly Gly Ala Gly Ser Pro Gly Ser
        115                 120                 125

Ala Gly Gly Pro Gly Ser Asp Pro
    130                 135

<210> SEQ ID NO 46
<211> LENGTH: 60
<212> TYPE: PRT
<213> ORGANISM: ARTIFICIAL SEQUENCE
<220> FEATURE:
<223> OTHER INFORMATION: synthetic construct IBT258

<400> SEQUENCE: 46
```

Met Ala Ser Gln Gln Gln Phe Gln Trp Gln Phe Glu Gln Pro Glu
1               5                   10                  15

Gly Gln Gln Gln Phe Gln Trp Gln Phe Glu Gln Pro Glu Gly Gln
            20                  25                  30

Gln Gln Phe Gln Trp Gln Phe Glu Gln Gln Gly Pro Gly Ser Gly Gly
            35                  40                  45

Ala Gly Ser Pro Gly Ser Ala Gly Gly Pro Gly Ser
        50                  55                  60

<210> SEQ ID NO 47
<211> LENGTH: 74
<212> TYPE: PRT
<213> ORGANISM: ARTIFICIAL SEQUENCE
<220> FEATURE:
<223> OTHER INFORMATION: synthetic construct IBT259

<400> SEQUENCE: 47

Met Ala Ser Gln Gln Gln Phe Arg Trp Arg Phe Glu Gln Gln Pro Glu
1               5                   10                  15

Gly Gln Gln Gln Phe Glu Trp Glu Phe Glu Gln Gln Pro Arg Gly Gln
            20                  25                  30

Gln Gln Phe Arg Trp Arg Phe Glu Gln Gln Pro Glu Gly Gln Gln Gln
            35                  40                  45

Phe Glu Trp Glu Phe Glu Gln Gln Gly Pro Gly Ser Gly Gly Ala Gly
        50                  55                  60

Ser Pro Gly Ser Ala Gly Gly Pro Gly Ser
65                  70

<210> SEQ ID NO 48
<211> LENGTH: 74
<212> TYPE: PRT
<213> ORGANISM: ARTIFICIAL SEQUENCE
<220> FEATURE:
<223> OTHER INFORMATION: synthetic construct IBT260

<400> SEQUENCE: 48

Met Ala Ser Gln Gln His Phe His Trp Gln Phe Glu Gln Gln Pro Glu
1               5                   10                  15

Gly Gln Gln His Phe His Trp Gln Phe Glu Gln Gln Pro Arg Gly Gln
            20                  25                  30

Gln His Phe His Trp Gln Phe Glu Gln Gln Pro Glu Gly Gln Gln His
            35                  40                  45

Phe His Trp Gln Phe Glu Gln Gln Gly Pro Gly Ser Gly Gly Ala Gly
        50                  55                  60

Ser Pro Gly Ser Ala Gly Gly Pro Gly Ser
65                  70

<210> SEQ ID NO 49
<211> LENGTH: 74
<212> TYPE: PRT
<213> ORGANISM: ARTIFICIAL SEQUENCE
<220> FEATURE:
<223> OTHER INFORMATION: synthetic construct IBT261

<400> SEQUENCE: 49

Met Ala Ser His Gln His Phe His Trp Gln Phe Glu Gln Gln Pro Glu
1               5                   10                  15

Gly His Gln His Phe His Trp Gln Phe Glu Gln Gln Pro Arg Gly His
            20                  25                  30

Gln His Phe His Trp Gln Phe Glu Gln Gln Pro Glu Gly His Gln His
         35                  40                  45

Phe His Trp Gln Phe Glu Gln Gln Gly Pro Gly Ser Gly Gly Ala Gly
 50                  55                  60

Ser Pro Gly Ser Ala Gly Gly Pro Gly Ser
 65                  70

<210> SEQ ID NO 50
<211> LENGTH: 136
<212> TYPE: PRT
<213> ORGANISM: Artificial Sequence
<220> FEATURE:
<223> OTHER INFORMATION: Synthetic Construct IBT262

<400> SEQUENCE: 50

Met Ala Ser Gln Gln Arg Phe Arg Trp Arg Phe Gln Gln Gln Gly Gly
 1               5                  10                  15

Ala Gly Gln Gly Gly Leu Gly Ser Gln Gly Ala Gly Gln Gly Ala Gly
                20                  25                  30

Gln Gln Arg Phe Glu Trp Glu Phe Gln Gln Gly Gly Ala Gly Gln
         35                  40                  45

Gly Gly Tyr Gly Gly Leu Gly Ser Gln Gly Ala Gly Arg Gly Gly Gln
 50                  55                  60

Gly Ala Gly Gln Gln Arg Phe Arg Trp Arg Phe Gln Gln Gln Gly Gly
 65                  70                  75                  80

Ala Gly Gln Gly Gly Tyr Gly Gly Leu Gly Ser Gln Gly Ala Gly Arg
                85                  90                  95

Gly Gly Leu Gly Gly Gln Gly Ala Gly Gln Gln Arg Phe Glu Trp Glu
            100                 105                 110

Phe Gln Gln Gln Gly Pro Gly Ser Gly Gly Ala Gly Ser Pro Gly Ser
        115                 120                 125

Ala Gly Gly Pro Gly Ser Asp Pro
    130                 135

<210> SEQ ID NO 51
<211> LENGTH: 154
<212> TYPE: PRT
<213> ORGANISM: Artificial Sequence
<220> FEATURE:
<223> OTHER INFORMATION: Synthetic Construct IBT263

<400> SEQUENCE: 51

Met Ala Ser Gln Gln Arg Phe Arg Trp Arg Phe Gln Gln Gln Gly Gly
 1               5                  10                  15

Ala Gly Gln Gly Gly Leu Gly Ser Gln Gly Ala Gly Gln Gly Ala Gly
                20                  25                  30

Gln Gln Arg Phe Glu Trp Glu Phe Gln Gln Gly Gly Ala Gly Gln
         35                  40                  45

Gly Gly Tyr Gly Gly Leu Gly Ser Gln Gly Ala Gly Arg Gly Gly Gln
 50                  55                  60

Gly Ala Gly Gln Gln Arg Phe Arg Trp Arg Phe Gln Gln Gln Gly Gly
 65                  70                  75                  80

Ala Gly Gln Gly Gly Tyr Gly Gly Leu Gly Ser Gln Gly Ala Gly Arg
                85                  90                  95

Gly Gly Leu Gly Gly Gln Gly Ala Gly Gln Gln Arg Phe Glu Trp Glu
            100                 105                 110

Phe Gln Gln Gln Gly Pro Gly Ser Gly Gly Ala Gly Ser Pro Gly Ser
        115                 120                 125

```
Ala Gly Gly Pro Gly Ser Gly Pro Gly Ser Gly Gly Ala Gly Ser Pro
    130                 135                 140

Gly Ser Ala Gly Gly Pro Gly Ser Asp Pro
145                 150

<210> SEQ ID NO 52
<211> LENGTH: 60
<212> TYPE: PRT
<213> ORGANISM: ARTIFICIAL SEQUENCE
<220> FEATURE:
<223> OTHER INFORMATION: synthetic construct IBT282

<400> SEQUENCE: 52

Met Ala Ser Gln Gln His Phe His Trp His Phe Gln Gln Gln Pro Arg
1               5                   10                  15

Gly Gln Gln His Phe His Trp His Phe Gln Gln Gln Pro Glu Gly Gln
            20                  25                  30

Gln His Phe His Trp His Phe Gln Gln Gln Pro Gly Ser Gly Gly
        35                  40                  45

Ala Gly Ser Pro Gly Ser Ala Gly Gly Pro Gly Ser
    50                  55                  60

<210> SEQ ID NO 53
<211> LENGTH: 60
<212> TYPE: PRT
<213> ORGANISM: ARTIFICIAL SEQUENCE
<220> FEATURE:
<223> OTHER INFORMATION: synthetic construct IBT283

<400> SEQUENCE: 53

Met Ala Ser Gln Gln His Phe His Trp His Phe Gln Gln Gln Pro Arg
1               5                   10                  15

Gly Gln Gln Lys Phe Lys Trp Lys Phe Gln Gln Gln Pro Glu Gly Gln
            20                  25                  30

Gln His Phe His Trp His Phe Gln Gln Gln Gly Pro Gly Ser Gly Gly
        35                  40                  45

Ala Gly Ser Pro Gly Ser Ala Gly Gly Pro Gly Ser
    50                  55                  60

<210> SEQ ID NO 54
<211> LENGTH: 60
<212> TYPE: PRT
<213> ORGANISM: ARTIFICIAL SEQUENCE
<220> FEATURE:
<223> OTHER INFORMATION: synthetic construct IBT284

<400> SEQUENCE: 54

Met Ala Ser Gln Gln Lys Phe His Trp His Phe Gln Gln Gln Pro Arg
1               5                   10                  15

Gly Gln Gln Lys Phe His Trp His Phe Gln Gln Gln Pro Glu Gly Gln
            20                  25                  30

Gln Lys Phe His Trp His Phe Gln Gln Gln Gly Pro Gly Ser Gly Gly
        35                  40                  45

Ala Gly Ser Pro Gly Ser Ala Gly Gly Pro Gly Ser
    50                  55                  60

<210> SEQ ID NO 55
<211> LENGTH: 60
<212> TYPE: PRT
<213> ORGANISM: ARTIFICIAL SEQUENCE
<220> FEATURE:
```

<223> OTHER INFORMATION: synthetic construct IBT287

<400> SEQUENCE: 55

Met Ala Ser Gln Gln Lys Phe Lys Trp Lys Phe Gln Gln Gln Pro Arg
1               5                   10                  15

Gly Gln Gln Lys Phe Lys Trp Lys Phe Gln Gln Pro Glu Gly Gln
            20                  25                  30

Gln Lys Phe Lys Trp Lys Phe Gln Gln Gln Gly Pro Gly Ser Gly Gly
        35                  40                  45

Ala Gly Ser Pro Gly Ser Ala Gly Gly Pro Gly Ser
    50                  55                  60

<210> SEQ ID NO 56
<211> LENGTH: 60
<212> TYPE: PRT
<213> ORGANISM: ARTIFICIAL SEQUENCE
<220> FEATURE:
<223> OTHER INFORMATION: synthetic construct IBT289

<400> SEQUENCE: 56

Met Ala Ser Gln Gln Lys Phe Lys Trp Lys Phe Gln Gln Gln Pro Arg
1               5                   10                  15

Gly Gln Gln His Phe His Trp His Phe Gln Gln Gln Pro Glu Gly Gln
            20                  25                  30

Gln Lys Phe Lys Trp Lys Phe Gln Gln Gln Gly Pro Gly Ser Gly Gly
        35                  40                  45

Ala Gly Ser Pro Gly Ser Ala Gly Gly Pro Gly Ser
    50                  55                  60

<210> SEQ ID NO 57
<211> LENGTH: 60
<212> TYPE: PRT
<213> ORGANISM: ARTIFICIAL SEQUENCE
<220> FEATURE:
<223> OTHER INFORMATION: synthetic construct IBT290

<400> SEQUENCE: 57

Met Ala Ser Gln Gln Lys Phe His Trp Lys Phe Gln Gln Gln Pro Arg
1               5                   10                  15

Gly Gln Gln Lys Phe His Trp Lys Phe Gln Gln Gln Pro Glu Gly Gln
            20                  25                  30

Gln Lys Phe His Trp Lys Phe Gln Gln Gln Gly Pro Gly Ser Gly Gly
        35                  40                  45

Ala Gly Ser Pro Gly Ser Ala Gly Gly Pro Gly Ser
    50                  55                  60

<210> SEQ ID NO 58
<211> LENGTH: 64
<212> TYPE: PRT
<213> ORGANISM: ARTIFICIAL SEQUENCE
<220> FEATURE:
<223> OTHER INFORMATION: synthetic construct IBT294

<400> SEQUENCE: 58

Met Ala Ser Gly Pro Cys Gly Gln Gln His Phe His Trp His Phe Gln
1               5                   10                  15

Gln Gln Pro Arg Gly Gln Gln Lys Phe Lys Trp Lys Phe Gln Gln Gln
            20                  25                  30

Pro Glu Gly Gln Gln His Phe His Trp His Phe Gln Gln Gln Gly Pro
        35                  40                  45

Gly Ser Gly Gly Ala Gly Ser Pro Gly Ser Ala Gly Gly Pro Gly Ser
    50                  55                  60

<210> SEQ ID NO 59
<211> LENGTH: 64
<212> TYPE: PRT
<213> ORGANISM: ARTIFICIAL SEQUENCE
<220> FEATURE:
<223> OTHER INFORMATION: synthetic construct IBT295

<400> SEQUENCE: 59

Met Ala Ser Gly Pro Cys Gly Gln Gln Lys Phe His Trp His Phe Gln
1               5                   10                  15

Gln Gln Pro Arg Gly Gln Gln Lys Phe His Trp His Phe Gln Gln Gln
            20                  25                  30

Pro Glu Gly Gln Gln Lys Phe His Trp His Phe Gln Gln Gln Gly Pro
        35                  40                  45

Gly Ser Gly Gly Ala Gly Ser Pro Gly Ser Ala Gly Gly Pro Gly Ser
    50                  55                  60

<210> SEQ ID NO 60
<211> LENGTH: 78
<212> TYPE: PRT
<213> ORGANISM: ARTIFICIAL SEQUENCE
<220> FEATURE:
<223> OTHER INFORMATION: synthetic construct IBT297

<400> SEQUENCE: 60

Met Ala Ser Gly Pro Cys Gly Gln Gln Lys Phe Lys Trp Lys Phe Gln
1               5                   10                  15

Gln Gln Pro Arg Gly Gln Gln Lys Phe Lys Trp Lys Phe Gln Gln Gln
            20                  25                  30

Pro Arg Gly Gln Gln Lys Phe Lys Trp Lys Phe Gln Gln Gln Pro Glu
        35                  40                  45

Gly Gln Gln Lys Phe Lys Trp Lys Phe Gln Lys Gln Gly Pro Gly Ser
    50                  55                  60

Gly Gly Ala Gly Ser Pro Gly Ser Ala Gly Gly Pro Gly Ser
65                  70                  75

<210> SEQ ID NO 61
<211> LENGTH: 78
<212> TYPE: PRT
<213> ORGANISM: ARTIFICIAL SEQUENCE
<220> FEATURE:
<223> OTHER INFORMATION: synthetic construct IBT298

<400> SEQUENCE: 61

Met Ala Ser Gly Pro Cys Gly Gln Gln Arg Phe Gln Trp Gln Phe Glu
1               5                   10                  15

Gln Gln Pro Arg Gly Gln Gln Arg Phe Gln Trp Gln Phe Glu Gln Gln
            20                  25                  30

Pro Arg Gly Gln Gln Arg Phe Gln Trp Gln Phe Glu Gln Gln Pro Glu
        35                  40                  45

Gly Gln Gln Arg Phe Gln Trp Gln Phe Glu Gln Gln Gly Pro Gly Ser
    50                  55                  60

Gly Gly Ala Gly Ser Pro Gly Ser Ala Gly Gly Pro Gly Ser
65                  70                  75

<210> SEQ ID NO 62
<211> LENGTH: 138
<212> TYPE: PRT

<213> ORGANISM: ARTIFICIAL SEQUENCE
<220> FEATURE:
<223> OTHER INFORMATION: synthetic construct IBT299

<400> SEQUENCE: 62

```
Met Ala Ser Gly Pro Cys Gly Gln Gln Arg Phe Gln Trp Gln Phe Glu
1               5                   10                  15
Gln Gln Gly Gly Ala Gly Gln Gly Gly Leu Gly Ser Gln Gly Ala Gly
            20                  25                  30
Gln Gly Ala Gly Gln Gln Arg Phe Gln Trp Gln Phe Glu Gln Gln Gly
        35                  40                  45
Gly Ala Gly Gln Gly Gly Tyr Gly Gly Leu Gly Ser Gln Gly Ala Gly
    50                  55                  60
Arg Gly Gly Gln Gly Ala Gly Gln Gln Arg Phe Gln Trp Gln Phe Glu
65                  70                  75                  80
Gln Gln Gly Gly Ala Gly Gln Gly Gly Tyr Gly Gly Leu Gly Ser Gln
                85                  90                  95
Gly Ala Gly Arg Gly Gly Leu Gly Gly Gln Gly Ala Gly Gln Gln Arg
            100                 105                 110
Phe Gln Trp Gln Phe Glu Gln Gln Gly Pro Gly Ser Gly Gly Ala Gly
        115                 120                 125
Ser Pro Gly Ser Ala Gly Gly Pro Gly Ser
    130                 135
```

<210> SEQ ID NO 63
<211> LENGTH: 154
<212> TYPE: PRT
<213> ORGANISM: Artificial Sequence
<220> FEATURE:
<223> OTHER INFORMATION: Synthetic Construct IBT310

<400> SEQUENCE: 63

```
Met Ala Ser His Gln His Phe His Trp Gln Phe Glu Gln Gln Gly Gly
1               5                   10                  15
Ala Gly Gln Gly Gly Leu Gly Ser Gln Gly Ala Gly Gln Gly Ala Gly
            20                  25                  30
His Gln His Phe His Trp Gln Phe Glu Gln Gln Gly Gly Ala Gly Gln
        35                  40                  45
Gly Gly Tyr Gly Gly Leu Gly Ser Gln Gly Ala Gly Arg Gly Gly Gln
    50                  55                  60
Gly Ala Gly His Gln His Phe His Trp Gln Phe Glu Gln Gln Gly Gly
65                  70                  75                  80
Ala Gly Gln Gly Gly Tyr Gly Gly Leu Gly Ser Gln Gly Ala Gly Arg
                85                  90                  95
Gly Gly Leu Gly Gly Gln Gly Ala Gly His Gln His Phe His Trp Gln
            100                 105                 110
Phe Glu Gln Gln Gly Pro Arg Ser Gly Gly Ala Gly Ser Pro Gly Ser
        115                 120                 125
Ala Gly Gly Pro Gly Ser Gly Pro Gly Ser Gly Ala Gly Ser Pro
    130                 135                 140
Gly Ser Ala Gly Gly Pro Gly Ser Asp Pro
145                 150
```

<210> SEQ ID NO 64
<211> LENGTH: 136
<212> TYPE: PRT
<213> ORGANISM: Artificial Sequence
<220> FEATURE:

-continued

<223> OTHER INFORMATION: Synthetic Construct IBT311

<400> SEQUENCE: 64

Met Ala Ser His Gln His Phe His Trp Gln Phe Glu Gln Gln Gly Gly
1               5                   10                  15

Ala Gly Gln Gly Gly Leu Gly Ser Gln Gly Ala Gly Gln Gly Ala Gly
            20                  25                  30

His Gln His Phe His Trp Gln Phe Glu Gln Gln Gly Gly Ala Gly Gln
        35                  40                  45

Gly Gly Tyr Gly Gly Leu Gly Ser Gln Gly Ala Gly Arg Gly Gly Gln
    50                  55                  60

Gly Ala Gly His Gln His Phe His Trp Gln Phe Glu Gln Gln Gly Gly
65                  70                  75                  80

Ala Gly Gln Gly Gly Tyr Gly Gly Leu Gly Ser Gln Gly Ala Gly Arg
                85                  90                  95

Gly Gly Leu Gly Gly Gln Gly Ala Gly His Gln His Phe His Trp Gln
            100                 105                 110

Phe Glu Gln Gln Gly Pro Arg Ser Gly Ala His Ser Pro Gly His Ser
        115                 120                 125

Ala Gly His Pro Gly Ser Asp Pro
    130                 135

<210> SEQ ID NO 65
<211> LENGTH: 154
<212> TYPE: PRT
<213> ORGANISM: Artificial Sequence
<220> FEATURE:
<223> OTHER INFORMATION: Synthetic Construct  IBT312

<400> SEQUENCE: 65

Met Ala Ser His Gln His Phe His Trp Gln Phe Glu Gln Gln Gly Gly
1               5                   10                  15

Ala Gly Gln Gly Gly Leu Gly Ser Gln Gly Ala Gly Gln Gly Ala Gly
            20                  25                  30

His Gln His Phe His Trp Gln Phe Glu Gln Gln Gly Gly Ala Gly Gln
        35                  40                  45

Gly Gly Tyr Gly Gly Leu Gly Ser Gln Gly Ala Gly Arg Gly Gly Gln
    50                  55                  60

Gly Ala Gly His Gln His Phe His Trp Gln Phe Glu Gln Gln Gly Gly
65                  70                  75                  80

Ala Gly Gln Gly Gly Tyr Gly Gly Leu Gly Ser Gln Gly Ala Gly Arg
                85                  90                  95

Gly Gly Leu Gly Gly Gln Gly Ala Gly His Gln His Phe His Trp Gln
            100                 105                 110

Phe Glu Gln Gln Gly Pro Arg Ser Gly Ala His Ser Pro Gly Ser
        115                 120                 125

Ala His Gly Pro Gly Ser His Pro Gly Ser Gly His Ala Gly Ser Pro
    130                 135                 140

His Ser Ala Gly His Pro Gly Ser Asp Pro
145                 150

<210> SEQ ID NO 66
<211> LENGTH: 128
<212> TYPE: PRT
<213> ORGANISM: Artificial Sequence
<220> FEATURE:
<223> OTHER INFORMATION: Synthetic Construct IBT313

-continued

```
<400> SEQUENCE: 66

Met Ala Ser His Gln His Phe His Trp Gln Phe Glu Gln Gln Gly Gly
1               5                   10                  15

Ala Gly Gln Gly Gly Leu Gly Ser Gln Gly Ala Gly Gln Gly Ala Gly
            20                  25                  30

His Gln His Phe His Trp Gln Phe Glu Gln Gln Gly Gly Ala Gly Gln
        35                  40                  45

Gly Gly Tyr Gly Gly Leu Gly Ser Gln Gly Ala Gly Arg Gly Gly Gln
    50                  55                  60

Gly Ala Gly His Gln His Phe His Trp Gln Phe Glu Gln Gln Gly Gly
65                  70                  75                  80

Ala Gly Gln Gly Gly Tyr Gly Gly Leu Gly Ser Gln Gly Ala Gly Arg
                85                  90                  95

Gly Gly Leu Gly Gly Gln Gly Ala Gly His Gln His Phe His Trp Gln
            100                 105                 110

Phe Glu Gln Gln Gly Pro Gly Ser Gly Ala Ser Pro Gly Ser Asp Pro
        115                 120                 125

<210> SEQ ID NO 67
<211> LENGTH: 128
<212> TYPE: PRT
<213> ORGANISM: Artificial Sequence
<220> FEATURE:
<223> OTHER INFORMATION: Synthetic Construct IBT314

<400> SEQUENCE: 67

Met Ala Ser His Gln His Phe His Trp Gln Phe Glu Gln Gln Gly Gly
1               5                   10                  15

Ala Gly Gln Gly Gly Leu Gly Ser Gln Gly Ala Gly Gln Gly Ala Gly
            20                  25                  30

His Gln His Phe His Trp Gln Phe Glu Gln Gln Gly Gly Ala Gly Gln
        35                  40                  45

Gly Gly Tyr Gly Gly Leu Gly Ser Gln Gly Ala Gly Arg Gly Gly Gln
    50                  55                  60

Gly Ala Gly His Gln His Phe His Trp Gln Phe Glu Gln Gln Gly Gly
65                  70                  75                  80

Ala Gly Gln Gly Gly Tyr Gly Gly Leu Gly Ser Gln Gly Ala Gly Arg
                85                  90                  95

Gly Gly Leu Gly Gly Gln Gly Ala Gly His Gln His Phe His Trp Gln
            100                 105                 110

Phe Glu Gln Gln Gly Pro His Ser Gly His Ser His Gly Ser Asp Pro
        115                 120                 125

<210> SEQ ID NO 68
<211> LENGTH: 67
<212> TYPE: PRT
<213> ORGANISM: ARTIFICIAL SEQUENCE
<220> FEATURE:
<223> OTHER INFORMATION: synthetic construct IBT315

<400> SEQUENCE: 68

Met Ala Ser His Gln His Phe His Trp Gln Phe Glu Gln Gln Gly Gly
1               5                   10                  15

Ala Gly Gln Gly Gly Tyr Gly Gly Leu Gly Ser Gln Gly Ala Gly Arg
            20                  25                  30

Gly Gly Gln Gly Ala Gly His Gln His Phe His Trp Gln Phe Glu Gln
        35                  40                  45
```

-continued

```
Gln Gly Pro Gly Ser Gly Gly Ala Gly Ser Pro Gly Ser Ala Gly Gly
        50                  55                  60
Pro Gly Ser
65

<210> SEQ ID NO 69
<211> LENGTH: 105
<212> TYPE: PRT
<213> ORGANISM: ARTIFICIAL SEQUENCE
<220> FEATURE:
<223> OTHER INFORMATION: synthetic construct IBT316

<400> SEQUENCE: 69

Met Ala Ser His Gln His Phe His Trp Gln Phe Glu Gln Gln Gly Gly
1               5                   10                  15

Ala Gly Gln Gly Gly Tyr Gly Gly Leu Gly Ser Gln Gly Ala Gly Arg
            20                  25                  30

Gly Gly Gln Gly Ala Gly His Gln His Phe His Trp Gln Phe Glu Gln
        35                  40                  45

Gln Gly Gly Ala Gly Gln Gly Gly Tyr Gly Gly Leu Gly Ser Gln Gly
    50                  55                  60

Ala Gly Arg Gly Gly Leu Gly Gly Gln Gly Ala Gly His Gln His Phe
65                  70                  75                  80

His Trp Gln Phe Glu Gln Gln Gly Pro Gly Ser Gly Gly Ala Gly Ser
                85                  90                  95

Pro Gly Ser Ala Gly Gly Pro Gly Ser
            100                 105

<210> SEQ ID NO 70
<211> LENGTH: 134
<212> TYPE: PRT
<213> ORGANISM: ARTIFICIAL SEQUENCE
<220> FEATURE:
<223> OTHER INFORMATION: synthetic construct IBT317

<400> SEQUENCE: 70

Met Ala Ser His Gln Lys Phe His Trp Gln Phe Glu Gln Gln Gly Gly
1               5                   10                  15

Ala Gly Gln Gly Gly Leu Gly Ser Gln Gly Ala Gly Gln Gly Ala Gly
            20                  25                  30

His Gln Lys Phe His Trp Gln Phe Glu Gln Gln Gly Gly Ala Gly Gln
        35                  40                  45

Gly Gly Tyr Gly Gly Leu Gly Ser Gln Gly Ala Gly Arg Gly Gly Gln
    50                  55                  60

Gly Ala Gly His Gln Lys Phe His Trp Gln Phe Glu Gln Gln Gly Gly
65                  70                  75                  80

Ala Gly Gln Gly Gly Tyr Gly Gly Leu Gly Ser Gln Gly Ala Gly Arg
                85                  90                  95

Gly Gly Leu Gly Gly Gln Gly Ala Gly His Gln Lys Phe His Trp Gln
            100                 105                 110

Phe Glu Gln Gln Gly Pro Gly Ser Gly Gly Ala Gly Ser Pro Gly Ser
        115                 120                 125

Ala Gly Gly Pro Gly Ser
    130

<210> SEQ ID NO 71
<211> LENGTH: 119
<212> TYPE: PRT
<213> ORGANISM: ARTIFICIAL SEQUENCE
```

```
<220> FEATURE:
<223> OTHER INFORMATION: synthetic construct IBT320

<400> SEQUENCE: 71
```

| Met<br>1 | Ala | Ser | His | Gln<br>5 | His | Phe | His | Trp | Gln<br>10 | Phe | Glu | Gln | Gln | Gly<br>15 | Gly |
|---|---|---|---|---|---|---|---|---|---|---|---|---|---|---|---|
| Ala | Gly | Gln | Gly<br>20 | Gly | Leu | Gly | Ser | Gln<br>25 | Gly | Ala | Gly | Gln | Gly<br>30 | Ala | Gly |
| His | Gln | His<br>35 | Phe | His | Trp | Gln | Phe<br>40 | Glu | Gln | Gln | Gly | Gly<br>45 | Ala | Gly | Gln |
| Gly | Gly<br>50 | Leu | Gly | Ser | Gln | Gly<br>55 | Ala | Gly | Gln | Gly | Ala<br>60 | Gly | His | Gln | His |
| Phe<br>65 | His | Trp | Gln | Phe | Glu<br>70 | Gln | Gln | Gly | Gly | Ala<br>75 | Gly | Gln | Gly | Gly | Leu<br>80 |
| Gly | Ser | Gln | Gly | Ala<br>85 | Gly | Gln | Gly | Ala | Gly<br>90 | His | Gln | His | Phe | His<br>95 | Trp |
| Gln | Phe | Glu | Gln<br>100 | Gln | Gly | Pro | Gly | Ser<br>105 | Gly | Gly | Ala | Gly | Ser<br>110 | Pro | Gly |
| Ser | Ala | Gly | Gly<br>115 | Pro | Gly | Ser | | | | | | | | | |

```
<210> SEQ ID NO 72
<211> LENGTH: 146
<212> TYPE: PRT
<213> ORGANISM: ARTIFICIAL SEQUENCE
<220> FEATURE:
<223> OTHER INFORMATION: synthetic construct IBT321

<400> SEQUENCE: 72
```

| Met<br>1 | Ala | Ser | His | Gln<br>5 | His | Phe | His | Trp | Gln<br>10 | Phe | Glu | Gln | Gln | Gly<br>15 | Gly |
|---|---|---|---|---|---|---|---|---|---|---|---|---|---|---|---|
| Ala | Gly | Gln | Gly<br>20 | Gly | Tyr | Gly | Gly | Leu<br>25 | Gly | Ser | Gln | Gly | Ala<br>30 | Gly | Arg |
| Gly | Gly | Leu<br>35 | Gly | Gly | Gln | Gly | Ala<br>40 | Gly | His | Gln | His | Phe<br>45 | His | Trp | Gln |
| Phe | Glu<br>50 | Gln | Gln | Gly | Gly | Ala<br>55 | Gly | Gln | Gly | Gly | Tyr<br>60 | Gly | Gly | Leu | Gly |
| Ser<br>65 | Gln | Gly | Ala | Gly | Arg<br>70 | Gly | Gly | Leu | Gly | Gly<br>75 | Gln | Gly | Ala | Gly | His<br>80 |
| Gln | His | Phe | His | Trp<br>85 | Gln | Phe | Glu | Gln | Gln<br>90 | Gly | Gly | Ala | Gly | Gln<br>95 | Gly |
| Gly | Tyr | Gly | Gly<br>100 | Leu | Gly | Ser | Gln | Gly<br>105 | Ala | Gly | Arg | Gly | Gly<br>110 | Leu | Gly |
| Gly | Gln | Gly<br>115 | Ala | Gly | His | Gln | His<br>120 | Phe | His | Trp | Gln | Phe<br>125 | Glu | Gln | Gln |
| Gly | Pro<br>130 | Gly | Ser | Gly | Gly | Ala<br>135 | Gly | Ser | Pro | Gly | Ser<br>140 | Ala | Gly | Gly | Pro |
| Gly<br>145 | Ser | | | | | | | | | | | | | | |

```
<210> SEQ ID NO 73
<211> LENGTH: 29
<212> TYPE: PRT
<213> ORGANISM: ARTIFICIAL SEQUENCE
<220> FEATURE:
<223> OTHER INFORMATION: synthetic construct IBT326

<400> SEQUENCE: 73
```

Met Gln Gln Arg Phe Gln Trp Gln Phe Glu Gln Gln Asn Gly Lys Thr
1               5                   10                  15

Gln Gln Arg Phe Gln Trp Gln Phe Glu Gln Gln Gly Ser
            20                  25

<210> SEQ ID NO 74
<211> LENGTH: 29
<212> TYPE: PRT
<213> ORGANISM: ARTIFICIAL SEQUENCE
<220> FEATURE:
<223> OTHER INFORMATION: synthetic construct IBT327

<400> SEQUENCE: 74

Met Gln Gln Arg Phe Gln Trp Gln Phe Glu Gln Gln Tyr Asn Gly Lys
1               5                   10                  15

Gln Gln Arg Phe Gln Trp Gln Phe Glu Gln Gln Gly Ser
            20                  25

<210> SEQ ID NO 75
<211> LENGTH: 134
<212> TYPE: PRT
<213> ORGANISM: ARTIFICIAL SEQUENCE
<220> FEATURE:
<223> OTHER INFORMATION: synthetic construct IBT332

<400> SEQUENCE: 75

Met Ala Ser His Gln His Phe His Trp Gln Phe Glu Gln Gln Gly Gly
1               5                   10                  15

Ala Gly Gln Gly Gly Leu Gly Cys Gln Gly Ala Gly Gln Gly Ala Gly
            20                  25                  30

His Gln His Phe His Trp Gln Phe Glu Gln Gln Gly Gly Ala Gly Gln
        35                  40                  45

Gly Gly Tyr Gly Gly Leu Gly Cys Gln Gly Ala Gly Arg Gly Gly Gln
    50                  55                  60

Gly Ala Gly His Gln His Phe His Trp Gln Phe Glu Gln Gln Gly Gly
65                  70                  75                  80

Ala Gly Gln Gly Gly Tyr Gly Gly Leu Gly Cys Gln Gly Ala Gly Arg
                85                  90                  95

Gly Gly Leu Gly Gly Gln Gly Ala Gly His Gln His Phe His Trp Gln
            100                 105                 110

Phe Glu Gln Gln Gly Pro Arg Ser Gly Ala His Ser Pro Gly His Ser
        115                 120                 125

Ala Gly His Pro Gly Ser
    130

<210> SEQ ID NO 76
<211> LENGTH: 228
<212> TYPE: PRT
<213> ORGANISM: ARTIFICIAL SEQUENCE
<220> FEATURE:
<223> OTHER INFORMATION: synthetic construct IBT334

<400> SEQUENCE: 76

Met Ala Ser His Gln His Phe His Trp Gln Phe Glu Gln Gln Gly Pro
1               5                   10                  15

Gly Ser Gly Gly Ala Gly Ser Pro Gly Ser Ala Gly Gly Pro Gly Ser
            20                  25                  30

His Asp His Lys Asn Gln Lys Glu Thr His Gln Arg His Ala Ala Gly
        35                  40                  45

Pro Gly Ser Gly Gly Ala Gly Ser Pro Gly Ser Ala Gly Gly Pro Gly

```
                    50                  55                  60
Ser His Gln His Phe His Trp Gln Phe Glu Gln Gln Gly Pro Gly Ser
 65                  70                  75                  80

Gly Gly Ala Gly Ser Pro Gly Ser Ala Gly Gly Pro Gly Ser Thr Ala
                 85                  90                  95

Glu Ile Gln Ser Ser Lys Asn Pro Asn Pro His Pro Gln Arg Ser Trp
            100                 105                 110

Thr Asn Gly Pro Gly Ser Gly Gly Ala Gly Ser Pro Gly Ser Ala Gly
        115                 120                 125

Gly Pro Gly Ser His Gln His Phe His Trp Gln Phe Glu Gln Gln Gly
    130                 135                 140

Pro Gly Ser Gly Gly Ala Gly Ser Pro Gly Ser Ala Gly Gly Pro Gly
145                 150                 155                 160

Ser Thr Pro Pro Glu Leu Ala His Thr Pro His His Leu Ala Gln Thr
                165                 170                 175

Arg Leu Thr Asp Arg Gly Pro Gly Ser Gly Gly Ala Gly Ser Pro Gly
            180                 185                 190

Ser Ala Gly Gly Pro Gly Ser His Gln His Phe His Trp Gln Phe Glu
        195                 200                 205

Gln Gln Gly Pro Gly Ser Gly Gly Ala Gly Ser Pro Gly Ser Ala Gly
    210                 215                 220

Gly Pro Gly Ser
225

<210> SEQ ID NO 77
<211> LENGTH: 134
<212> TYPE: PRT
<213> ORGANISM: ARTIFICIAL SEQUENCE
<220> FEATURE:
<223> OTHER INFORMATION: synthetic construct IBT340

<400> SEQUENCE: 77

Met Ala Ser His Gln His Phe His Trp Gln Phe Glu Gln Gln Gly Gly
  1               5                  10                  15

Ala Gly Gln Gly Gly Leu Gly Cys Gln Gly Ala Gly Gln Gly Ala Gly
             20                  25                  30

His Gln His Phe His Trp Gln Phe Glu Gln Gln Gly Gly Ala Gly Gln
         35                  40                  45

Gly Gly Tyr Gly Gly Leu Gly Cys Gln Gly Ala Gly Arg Gly Gly Gln
     50                  55                  60

Gly Ala Gly His Gln His Phe His Trp Gln Phe Glu Gln Gln Gly Gly
 65                  70                  75                  80

Ala Gly Gln Gly Gly Tyr Gly Gly Leu Gly Cys Gln Gly Ala Gly Arg
                 85                  90                  95

Gly Gly Leu Gly Gly Gln Gly Ala Gly His Gln His Phe His Trp Gln
            100                 105                 110

Phe Glu Gln Gln Gly Pro Gly Ser Gly Gly Ala Gly Ser Pro Gly Ser
        115                 120                 125

Ala Gly Gly Pro Gly Ser
    130

<210> SEQ ID NO 78
<211> LENGTH: 4936
<212> TYPE: DNA
<213> ORGANISM: Artificial Sequence
<220> FEATURE:
<223> OTHER INFORMATION: Synthetic Construct pLR548
```

<400> SEQUENCE: 78

```
aagaaaccaa ttgtccatat tgcatcagac attgccgtca ctgcgtcttt tactggctct      60
tctcgctaac caaaccggta accccgctta ttaaaagcat tctgtaacaa agcgggacca     120
aagccatgac aaaaacgcgt aacaaaagtg tctataatca cggcagaaaa gtccacattg     180
attatttgca cggcgtcaca ctttgctatg ccatagcatt tttatccata agattagcgg     240
atcttacctg acgcttttta tcgcaactct ctactgtttc tccatacccg ttttttgggc     300
taacaggagg aattacatat gcagcagaaa tttaaatgga aatttcagca gcagccgcgc     360
ggccagcaga atttaaatg gaaatttcag cagcagccgc gcggccagca gaaatttaaa      420
tggaaatttc agcagcagcc ggaaggccag cagaaattta atggaaatt tcagaagcag      480
ggatccgatc catctgaggg ctccgaatct ggtgcacagt ctcagctgcc tgacaagcac     540
agcggcctgc acgagcgtgc tccgcagcgt tacggtccgg agccggaacc ggagcctgaa     600
ccgattccgg agccgccgaa agaagcccca gtggttattg aaaaaccgaa accgaagccg     660
aaaccaaaac ctaaaccacc ggcccatgac acaagaacc agaaagaaac ccaccagcgt      720
cacgcggctg gcgcggtta aggcgcgccg acccagcttt cttgtacaaa gtggttgatt      780
cgaggctgct aacaaagccc gaaaggaagc tgagttggct gctgccaccg ctgagcaata     840
actagcataa ccccttgggg cctctaaacg ggtcttgagg gtttttgc tgaaaggagg       900
aactatatcc ggatatccac aggacgggtg tggtcgccat gatcgcgtag tcgatagtgg     960
ctccaagtag cgaagcgagc aggactgggc ggcggccaaa gcggtcggac agtgctccga    1020
gaacgggtgc gcatagaaat tgcatcaacg catatagcgc tagcagcacg ccatagtgac    1080
tggcgatgct gtcggaatgg acgatatccc gcaagaggcc cggcagtacc ggcataacca    1140
agcctatgcc tacagcatcc agggtgacgg tgccgaggat gacgatgagc gcattgttag    1200
atttcataca cggtgcctga ctgcgttagc aatttaactg tgataaacta ccgcattaaa    1260
gcttatcgat gataagctgt caaacatgag aattcgaagc ttggctgttt tggcggatga    1320
gagaagattt tcagcctgat acagattaaa tcagaacgca gaagcggtct gataaaacag    1380
aatttgcctg gcggcagtag cgcggtggtc ccacctgacc ccatgccgaa ctcagaagtg    1440
aaacgccgta gcgccgatgg tagtgtgggg tctccccatg cgagagtagg gaactgccag    1500
gcatcaaata aaacgaaagg ctcagtcgaa agactgggcc tttcgtttta tctgttgttt    1560
gtcggtgaac gctctcctga gtaggacaaa tccgccggga gcggatttga acgttgcgaa    1620
gcaacgccc ggagggtggc gggcaggacg cccgccataa actgccaggc atcaaattaa     1680
gcagaaggcc atcctgacgg atggcctttt tgcgtttcta caaactcttt tgtttatttt    1740
tctaaataca ttcaaatatg tatccgctca tgagacaata accctgataa atgcttcaat    1800
aatattgaaa aaggaagagt atgagtattc aacatttccg tgtcgccctt attcccttt     1860
ttgcggcatt ttgccttcct gttttttgctc acccagaaac gctggtgaaa gtaaaagatg    1920
ctgaagatca gttgggtgca cgagtgggtt acatcgaact ggatctcaac agcggtaaga    1980
tccttgagag ttttcgcccc gaagaacgtt ttccaatgat gagcactttt aaagttctgc    2040
tatgtggcgc ggtattatcc cgtgttgacg ccgggcaaga gcaactcggt cgccgcatac    2100
actattctca gaatgacttg gttgagtact caccagtcac agaaaagcat cttacggatg    2160
gcatgacagt aagagaatta tgcagtgctg ccataaccat gagtgataac actgcggcca    2220
acttacttct gacaacgatc ggaggaccga aggagctaac cgcttttttg cacaacatgg    2280
```

```
gggatcatgt aactcgcctt gatcgttggg aaccggagct gaatgaagcc ataccaaacg    2340
acgagcgtga caccacgatg cctgtagcaa tggcaacaac gttgcgcaaa ctattaactg    2400
gcgaactact tactctagct tcccggcaac aattaataga ctggatggag gcggataaag    2460
ttgcaggacc acttctgcgc tcggcccttc cggctggctg gttattgct gataaatctg     2520
gagccggtga gcgtgggtct cgcggtatca ttgcagcact ggggccagat ggtaagccct    2580
cccgtatcgt agttatctac acgacgggga gtcaggcaac tatggatgaa cgaaatagac    2640
agatcgctga gataggtgcc tcactgatta agcattggta actgtcagac caagtttact    2700
catatatact ttagattgat ttaaaacttc attttaatt taaaaggatc taggtgaaga     2760
tcctttttga taatctcatg accaaaatcc cttaacgtga gttttcgttc cactgagcgt    2820
cagaccccgt agaaaagatc aaaggatctt cttgagatcc ttttttctg cgcgtaatct     2880
gctgcttgca acaaaaaaa ccaccgctac cagcggtggt ttgtttgccg gatcaagagc     2940
taccaactct ttttccgaag gtaactggct tcagcagagc gcagatacca aatactgtcc    3000
ttctagtgta gccgtagtta ggccaccact tcaagaactc tgtagcaccg cctacatacc    3060
tcgctctgct aatcctgtta ccagtggctg ctgccagtgg cgataagtcg tgtcttaccg    3120
ggttggactc aagacgatag ttaccggata aggcgcagcg tcgggctga acggggggtt     3180
cgtgcacaca gcccagcttg gagcgaacga cctacaccga actgagatac ctacagcgtg    3240
agctatgaga aagcgccacg cttcccgaag ggagaaaggc ggacaggtat ccggtaagcg    3300
gcagggtcgg aacaggagag cgcacgaggg agcttccagg gggaaacgcc tggtatcttt    3360
atagtcctgt cgggtttcgc cacctctgac ttgagcgtcg attttgtga tgctcgtcag     3420
gggggcggag cctatggaaa aacgccagca acgcggcctt tttacggttc ctggcctttt    3480
gctgcctttt tgctcacatg ttctttcctg cgttatcccc tgattctgtg gataaccgta    3540
ttaccgcctt tgagtgagct gataccgctc gccgcagccg aacgaccgag cgcagcgagt    3600
cagtgagcga ggaagcggaa gagcgcctga tgcggtattt tctccttacg catctgtgcg    3660
gtatttcaca ccgcatatat ggtgcactct cagtacaatc tgctctgatg ccgcatagtt    3720
aagccagtat acactccgct atcgctacgt gactgggtca tggctgcgcc ccgacacccg    3780
ccaacacccg ctgacgcgcc ctgacgggct tgtctgctcc cggcatccgc ttacagacaa    3840
gctgtgaccg tctccgggag ctgcatgtgt cagaggtttt caccgtcatc accgaaacgc    3900
gcgaggcagc agatcaattc gcgcgcgaag gcgaagcggc atgcataatg tgcctgtcaa    3960
atggacgaag cagggattct gcaaacccta tgctactccg tcaagccgtc aattgtctga    4020
ttcgttacca attatgacaa cttgacggct acatcattca ctttttcttc acaaccggca    4080
cggaactcgc tcgggctggc cccggtgcat ttttaaata cccgcgagaa atagagttga    4140
tcgtcaaaac caacattgcg accgacggtg gcgataggca tccgggtggt gctcaaaagc    4200
agcttcgcct ggctgatacg ttggtcctcg cgccagctta agacgctaat ccctaactgc    4260
tggcggaaaa gatgtgacag acgcgacggc gacaagcaaa catgctgtgc gacgctggcg    4320
atatcaaaat tgctgtctgc caggtgatcg ctgatgtact gacaagcctc gcgtacccga    4380
ttatccatcg gtggatggag cgactcgtta atcgcttcca tgcgccgcag taacaattgc    4440
tcaagcagat ttatcgccag cagctccgaa tagcgccctt ccccttgccc ggcgttaatg    4500
atttgcccaa acaggtcgct gaaatgcggc tggtgcgctt catccgggcg aaagaacccc    4560
gtattggcaa atattgacgg ccagttaagc cattcatgcc agtaggcgcg cggacgaaag    4620
taaacccact ggtgatacca ttcgcgagcc tccggatgac gaccgtagtg atgaatctct    4680
```

```
cctggcggga acagcaaaat atcacccggt cggcaaacaa attctcgtcc ctgattttc      4740 accacccct gaccgcgaat ggtgagattg agaatataac ctttcattcc cagcggtcgg      4800
tcgataaaaa aatcgagata accgttggcc tcaatcggcg ttaaaccgc caccagatgg      4860 gcattaaacg agtatcccgg cagcaggga tcattttgcg cttcagccat acttttcata      4920
ctcccgccat tcagag                                                    4936
```

<210> SEQ ID NO 79
<211> LENGTH: 5804
<212> TYPE: DNA
<213> ORGANISM: Artificial Sequence
<220> FEATURE:
<223> OTHER INFORMATION: Synthetic Construct pLD001.233

<400> SEQUENCE: 79

```
agatctcgat cccgcgaaat taatacgact cactataggg agaccacaac ggtttccctc      60
tagaaataat tttgtttaac tttaagaagg agatatacat atggcgagcc accaacactt     120
tcactggcaa ttcgagcaac agccacgcgg tcatcagcat tttcattggc agttcgagca     180
gcagccgcgt ggccaccagc acttccactg cagtttgaa caacagccgg agggtcatca     240
acattttcac tggcaattcg aacaacaggg atcctaatag ggcgcgccga cccagctttc     300
ttgtacaaag tggttgattc gaggctgcta acaaagcccg aaaggaagct gagttggctg     360
ctgccaccgc tgagcaataa ctagcataac cccttgggc ctctaaacgg gtcttgaggg     420
gttttttgct gaaaggagga actatatccg gatatccaca ggacgggtgt ggtcgccatg     480
atcgcgtagt cgatagtggc tccaagtagc gaagcgagca ggactgggcg gcggccaaag     540
cggtcggaca gtgctccgag aacgggtgcg catagaaatt gcatcaacgc atatagcgct     600
agcagcacgc catagtgact ggcgatgctg tcggaatgga cgatatcccg caagaggccc     660
ggcagtaccg gcataaccaa gcctatgcct acagcatcca gggtgacggt gccgaggatg     720
acgatgagcg cattgttaga tttcatacac ggtgcctgac tgcgttagca atttaactgt     780
gataaactac cgcattaaag cttgcagtgg cggttttcat ggcttgttat gactgttttt     840
ttggggtaca gtctatgcct cgggcatcca agcagcaagc gcgttacgcc gtgggtcgat     900
gtttgatgtt atggagcagc aacgatgtta cgcagcaggg cagtcgccct aaaacaaagt     960
taaacatcat gagggaagcg gtgatcgccg aagtatcgac tcaactatca gaggtagttg    1020
gcgtcatcga gcgccatctc gaaccgacgt tgctggccgt acatttgtac ggctccgcag    1080
tggatggcgg cctgaagcca cacagtgata ttgatttgct ggttacggtg accgtaaggc    1140
ttgatgaaac aacgcggcga gctttgatca acgacctttt ggaaacttcg gcttcccctg    1200
gagagagcga gattctccgc gctgtagaag tcaccattgt tgtgcacgac gacatcattc    1260
cgtggcgtta tccagctaag cgcgaactgc aatttggaga atggcagcgc aatgacattc    1320
ttgcaggtat cttcgagcca gccacgatcg acattgatct ggctatcttg ctgacaaaag    1380
caagagaaca tagcgttgcc ttggtaggtc cagcggcgga ggaactcttt gatccggttc    1440
ctgaacagga tctatttgag gcgctaaatg aaaccttaac gctatggaac tcgccgcccg    1500
actgggctgg cgatgagcga aatgtagtgc ttacgttgtc ccgcatttgg tacagcgcag    1560
taaccggcaa aatcgcgccg aaggatgtcg ctgccgactg ggcaatggag cgcctgccgg    1620
cccagtatca gcccgtcata cttgaagcta gacaggctta tcttggacaa gaagaagatc    1680
gcttggcctc gcgcgcagat cagttggaag aatttgtcca ctacgtgaaa ggcgagatca    1740
```

```
ccaaggtagt cggcaaataa tgtctaacaa ttcgttcaag cttatcgatg ataagctgtc   1800
aaacatgaga attcttgaag acgaaagggc ctcgtgatac gcctattttt ataggttaat   1860
gtcatgataa taatggtttc ttagacgtca ggtggcactt ttcggggaaa tgtgcgcgga   1920
acccctattt gttattttt ctaaatacat tcaaatatgt atccgctcat gagacaataa    1980
ccctgataaa tgcttcaata atattgaaaa aggaagagta tgagtattca acatttccgt   2040
gtcgccctta ttcccttttt tgcggcattt tgccttcctg tttttgctca cccagaaacg   2100
ctggtgaaag taaaagatgc tgaagatcag ttgggtgcac gagtgggtta catcgaactg   2160
gatctcaaca gcggtaagat ccttgagagt tttcgccccg aagaacgttt tccaatgatg   2220
agcactttta aagttctgct atgtggcgcg gtattatccc gtgttgacgc cgggcaagag   2280
caactcggtc gccgcataca ctattctcag aatgacttgg ttgagtactc accagtcaca   2340
gaaaagcatc ttacggatgg catgacagta agagaattat gcagtgctgc cataaccatg   2400
agtgataaca ctgcggccaa cttacttctg acaacgatcg gaggaccgaa ggagctaacc   2460
gcttttttgc acaacatggg gatcatgta actcgccttg atcgttggga accggagctg    2520
aatgaagcca taccaaacga cgagcgtgac accacgatgc ctgcagcaat ggcaacaacg   2580
ttgcgcaaac tattaactgg cgaactactt actctagctt cccggcaaca attaatagac   2640
tggatggagg cggataaagt tgcaggacca cttctgcgct cggcccttcc ggctggctgg   2700
tttattgctg ataaatctgg agccggtgag cgtgggtctc gcggtatcat tgcagcactg   2760
gggccagatg gtaagccctc ccgtatcgta gttatctaca cgacggggag tcaggcaact   2820
atggatgaac gaaatagaca gatcgctgag ataggtgcct cactgattaa gcattggtaa   2880
ctgtcagacc aagtttactc atatatactt tagattgatt taaaacttca tttttaattt   2940
aaaaggatct aggtgaagat ccttttttgat aatctcatga ccaaaatccc ttaacgtgag   3000
ttttcgttcc actgagcgtc agaccccgta gaaaagatca aggatcttc ttgagatcct    3060 ttttttctgc gcgtaatctg ctgcttgcaa acaaaaaaac caccgctacc agcggtggtt   3120
tgtttgccgg atcaagagct accaactctt tttccgaagg taactggctt cagcagagcg   3180
cagataccaa atactgtcct tctagtgtag ccgtagttag gccaccactt caagaactct   3240
gtagcaccgc ctacatacct cgctctgcta atcctgttac cagtggctgc tgccagtggc   3300
gataagtcgt gtcttaccgg gttggactca agacgatagt taccggataa ggcgcagcgg   3360
tcgggctgaa cggggggttc gtgcacacag cccagcttgg agcgaacgac ctacaccgaa   3420
ctgagatacc tacagcgtga gctatgagaa agcgccacgc ttcccgaagg gagaaaggcg   3480
gacaggtatc cggtaagcgg cagggtcgga acaggagagc gcacgaggga gcttccaggg   3540
ggaaacgcct ggtatcttta tagtcctgtc gggtttcgcc acctctgact tgagcgtcga   3600
tttttgtgat gctcgtcagg gggcggagc ctatggaaaa acgccagcaa cgcggccttt    3660
ttacggttcc tggccttttg ctggccttt gctcacatgt tctttcctgc gttatcccct    3720
gattctgtgg ataaccgtat taccgccttt gagtgagctg ataccgctcg ccgcagccga   3780
acgaccgagc gcagcgagtc agtgagcgag gaagcggaag agcgcctgat gcggtatttt   3840
ctccttacgc atctgtgcgg tatttcacac cgcatatatg gtgcactctc agtacaatct   3900
gctctgatgc cgcatagtta agccagtata cactccgcta tcgctacgtg actgggtcat   3960
ggctgcgccc cgacacccgc caacacccgc tgacgcgccc tgacgggctt gtctgctccc   4020
ggcatccgct tacagacaag ctgtgaccgt ctccgggagc tgcatgtgtc agaggttttc   4080
accgtcatca ccgaaacgcg cgaggcagct gcggtaaagc tcatcagcgt ggtcgtgaag   4140
```

```
cgattcacag atgtctgcct gttcatccgc gtccagctcg ttgagtttct ccagaagcgt    4200
taatgtctgg cttctgataa agcgggccat gttaagggcg ttttttcct gtttggtcac    4260 tgatgcctcc gtgtaagggg gatttctgtt catgggggta atgataccga tgaaacgaga    4320
gaggatgctc acgatacggg ttactgatga tgaacatgcc cggttactgg aacgttgtga    4380
gggtaaacaa ctggcggtat ggatgcggcg ggaccagaga aaaatcactc agggtcaatg    4440
ccagcgcttc gttaatacag atgtaggtgt tccacaggt agccagcagc atcctgcgat    4500
gcagatccgg aacataatgg tgcagggcgc tgacttccgc gtttccagac tttacgaaac    4560
acggaaaccg aagaccattc atgttgttgc tcaggtcgca gacgttttgc agcagcagtc    4620
gcttcacgtt cgctcgcgta tcggtgattc attctgctaa ccagtaaggc aaccccgcca    4680
gcctagccgg gtcctcaacg acaggagcac gatcatgcgc acccgtggcc aggacccaac    4740
gctgcccgag atgcgccgcg tgcggctgct ggagatggcg gacgcgatgg atatgttctg    4800
ccaagggttg gtttgcgcat tcacagttct ccgcaagaat tgattggctc caattcttgg    4860
agtggtgaat ccgttagcga ggtgccgccg gcttccattc aggtcgaggt ggcccggctc    4920
catgcaccgc gacgcaacgc ggggaggcag acaaggtata gggcggcgcc tacaatccat    4980
gccaacccgt tccatgtgct cgccgaggcg gcataaatcg ccgtgacgat cagcggtcca    5040
gtgatcgaag ttaggctggt aagagccgcg agcgatcctt gaagctgtcc ctgatggtcg    5100
tcatctacct gcctggacag catggcctgc aacgcgggca tcccgatgcc gccggaagcg    5160
agaagaatca taatgggaa ggccatccag cctcgcgtcg cgaacgccag caagacgtag    5220
cccagcgcgt cggccgccat gccggcgata atggcctgct tctcgccgaa acgtttggtg    5280
gcgggaccag tgacgaaggc ttgagcgagg gcgtgcaaga ttccgaatac cgcaagcgac    5340
aggccgatca tcgtcgcgct ccagcgaaag cggtcctcgc cgaaaatgac ccagagcgct    5400
gccggcacct gtcctacgag ttgcatgata aagaagacag tcataagtgc ggcgacgata    5460
gtcatgcccc gcgcccaccg gaaggagctg actgggttga aggctctcaa gggcatcggt    5520
cgatcgacgc tctcccttat gcgactcctg cattaggaag cagcccagta gtaggttgag    5580
gccgttgagc accgccgccg caaggaatgg tgcatgcaag gagatggcgc ccaacagtcc    5640
cccggccacg gggcctgcca ccatacccac gccgaaacaa gcgctcatga gcccgaagtg    5700
gcgagcccga tcttccccat cggtgatgtc ggcgatatag gcgccagcaa ccgcacctgt    5760
ggcgccggtg atgccggcca cgatgcgtcc ggcgtagagg atcg            5804
```

<210> SEQ ID NO 80
<211> LENGTH: 11
<212> TYPE: PRT
<213> ORGANISM: artificial sequence
<220> FEATURE:
<223> OTHER INFORMATION: synthetic construct

<400> SEQUENCE: 80

His Gln His Phe His Trp Gln Phe Glu Gln Gln
1               5                   10

<210> SEQ ID NO 81
<211> LENGTH: 11
<212> TYPE: PRT
<213> ORGANISM: artificial sequence
<220> FEATURE:
<223> OTHER INFORMATION: synthetic construct

<400> SEQUENCE: 81

```
Gln Gln His Phe His Trp His Phe Gln Gln Gln
1               5                   10
```

<210> SEQ ID NO 82
<211> LENGTH: 11
<212> TYPE: PRT
<213> ORGANISM: artificial sequence
<220> FEATURE:
<223> OTHER INFORMATION: synthetic construct

<400> SEQUENCE: 82

```
Gln Gln His Phe His Trp Gln Phe Glu Gln Gln
1               5                   10
```

<210> SEQ ID NO 83
<211> LENGTH: 11
<212> TYPE: PRT
<213> ORGANISM: artificial sequence
<220> FEATURE:
<223> OTHER INFORMATION: synthetic construct

<400> SEQUENCE: 83

```
Gln Gln His Phe Gln Trp Gln Phe Glu Gln Gln
1               5                   10
```

<210> SEQ ID NO 84
<211> LENGTH: 11
<212> TYPE: PRT
<213> ORGANISM: artificial sequence
<220> FEATURE:
<223> OTHER INFORMATION: synthetic construct

<400> SEQUENCE: 84

```
Gln Gln Lys Phe His Trp His Phe Gln Gln Gln
1               5                   10
```

<210> SEQ ID NO 85
<211> LENGTH: 11
<212> TYPE: PRT
<213> ORGANISM: artificial sequence
<220> FEATURE:
<223> OTHER INFORMATION: synthetic construct

<400> SEQUENCE: 85

```
Gln Gln Gln Phe Gln Trp Gln Phe Glu Gln Gln
1               5                   10
```

<210> SEQ ID NO 86
<211> LENGTH: 11
<212> TYPE: PRT
<213> ORGANISM: artificial sequence
<220> FEATURE:
<223> OTHER INFORMATION: synthetic construct

<400> SEQUENCE: 86

```
Gln Gln Gln Phe Arg Trp Gln Phe Gln Gln Gln
1               5                   10
```

<210> SEQ ID NO 87
<211> LENGTH: 11
<212> TYPE: PRT
<213> ORGANISM: artificial sequence
<220> FEATURE:
<223> OTHER INFORMATION: synthetic construct

<400> SEQUENCE: 87

```
Gln Gln Gln Phe Arg Trp Arg Phe Glu Gln Gln
1               5                   10
```

<210> SEQ ID NO 88
<211> LENGTH: 13
<212> TYPE: PRT
<213> ORGANISM: artificial sequence
<220> FEATURE:
<223> OTHER INFORMATION: synthetic construct

<400> SEQUENCE: 88

```
Gln Gln Arg Phe Gln Phe Gln Phe Gln Phe Glu Gln Gln
1               5                   10
```

<210> SEQ ID NO 89
<211> LENGTH: 11
<212> TYPE: PRT
<213> ORGANISM: artificial sequence
<220> FEATURE:
<223> OTHER INFORMATION: synthetic construct

<400> SEQUENCE: 89

```
Gln Gln Arg Phe Gln Trp Gln Phe Glu Gln Gln
1               5                   10
```

<210> SEQ ID NO 90
<211> LENGTH: 11
<212> TYPE: PRT
<213> ORGANISM: artificial sequence
<220> FEATURE:
<223> OTHER INFORMATION: synthetic construct

<400> SEQUENCE: 90

```
Gln Gln Arg Phe Gln Trp Gln Phe Gln Gln Gln
1               5                   10
```

<210> SEQ ID NO 91
<211> LENGTH: 15
<212> TYPE: PRT
<213> ORGANISM: artificial sequence
<220> FEATURE:
<223> OTHER INFORMATION: synthetic construct

<400> SEQUENCE: 91

```
Gln Gln Arg Phe Gln Trp Gln Phe Gln Trp Gln Phe Glu Gln Gln
1               5                   10                  15
```

<210> SEQ ID NO 92
<211> LENGTH: 11
<212> TYPE: PRT
<213> ORGANISM: artificial sequence
<220> FEATURE:
<223> OTHER INFORMATION: synthetic construct

<400> SEQUENCE: 92

```
Gln Gln Arg Phe Gln Trp Gln Phe Arg Gln Gln
1               5                   10
```

<210> SEQ ID NO 93
<211> LENGTH: 15
<212> TYPE: PRT
<213> ORGANISM: artificial sequence
<220> FEATURE:
<223> OTHER INFORMATION: synthetic construct

<400> SEQUENCE: 93

```
Gln Gln Arg Phe Gln Trp Gln Phe Arg Trp Gln Phe Glu Gln Gln
```

```
<210> SEQ ID NO 94
<211> LENGTH: 13
<212> TYPE: PRT
<213> ORGANISM: artificial sequence
<220> FEATURE:
<223> OTHER INFORMATION: synthetic construct

<400> SEQUENCE: 94

Gln Gln Arg Phe Arg Phe Gln Phe Gln Phe Glu Gln Gln
1               5                   10

<210> SEQ ID NO 95
<211> LENGTH: 13
<212> TYPE: PRT
<213> ORGANISM: artificial sequence
<220> FEATURE:
<223> OTHER INFORMATION: synthetic construct

<400> SEQUENCE: 95

Gln Gln Arg Phe Arg Phe Arg Phe Gln Phe Glu Gln Gln
1               5                   10

<210> SEQ ID NO 96
<211> LENGTH: 15
<212> TYPE: PRT
<213> ORGANISM: artificial sequence
<220> FEATURE:
<223> OTHER INFORMATION: synthetic construct

<400> SEQUENCE: 96

Gln Gln Arg Phe Arg Trp Gln Phe Gln Trp Gln Phe Glu Gln Gln
1               5                   10                  15

<210> SEQ ID NO 97
<211> LENGTH: 15
<212> TYPE: PRT
<213> ORGANISM: artificial sequence
<220> FEATURE:
<223> OTHER INFORMATION: synthetic construct

<400> SEQUENCE: 97

Gln Gln Arg Phe Arg Trp Gln Phe Arg Trp Gln Phe Glu Gln Gln
1               5                   10                  15

<210> SEQ ID NO 98
<211> LENGTH: 11
<212> TYPE: PRT
<213> ORGANISM: artificial sequence
<220> FEATURE:
<223> OTHER INFORMATION: synthetic construct

<400> SEQUENCE: 98

Gln Gln Arg Phe Arg Trp Arg Phe Gln Gln Gln
1               5                   10

<210> SEQ ID NO 99
<211> LENGTH: 11
<212> TYPE: PRT
<213> ORGANISM: artificial sequence
<220> FEATURE:
<223> OTHER INFORMATION: synthetic construct

<400> SEQUENCE: 99

Gln Gln Lys Phe Lys Trp Lys Phe Gln Gln Gln
1               5                   10
```

```
<210> SEQ ID NO 100
<211> LENGTH: 11
<212> TYPE: PRT
<213> ORGANISM: artificial sequence
<220> FEATURE:
<223> OTHER INFORMATION: synthetic construct

<400> SEQUENCE: 100

Gln Gln Arg Phe Glu Trp Glu Phe Gln Gln Gln
1               5                   10

<210> SEQ ID NO 101
<211> LENGTH: 11
<212> TYPE: PRT
<213> ORGANISM: artificial sequence
<220> FEATURE:
<223> OTHER INFORMATION: synthetic construct

<400> SEQUENCE: 101

Gln Gln Gln Phe Glu Trp Glu Phe Glu Gln Gln
1               5                   10

<210> SEQ ID NO 102
<211> LENGTH: 11
<212> TYPE: PRT
<213> ORGANISM: artificial sequence
<220> FEATURE:
<223> OTHER INFORMATION: synthetic construct

<400> SEQUENCE: 102

Gln Gln Lys Phe Lys Trp Lys Phe Gln Lys Gln
1               5                   10

<210> SEQ ID NO 103
<211> LENGTH: 11
<212> TYPE: PRT
<213> ORGANISM: artificial sequence
<220> FEATURE:
<223> OTHER INFORMATION: synthetic construct

<400> SEQUENCE: 103

Gln Gln Lys Phe His Trp Lys Phe Gln Gln Gln
1               5                   10

<210> SEQ ID NO 104
<211> LENGTH: 11
<212> TYPE: PRT
<213> ORGANISM: artificial sequence
<220> FEATURE:
<223> OTHER INFORMATION: synthetic construct

<400> SEQUENCE: 104

His Gln Lys Phe His Trp Gln Phe Glu Gln Gln
1               5                   10

<210> SEQ ID NO 105
<211> LENGTH: 12
<212> TYPE: PRT
<213> ORGANISM: artificial sequence
<220> FEATURE:
<223> OTHER INFORMATION: Synthetic construct

<400> SEQUENCE: 105

Arg Val Pro Asn Lys Thr Val Thr Val Asp Gly Ala
1               5                   10
```

<210> SEQ ID NO 106
<211> LENGTH: 12
<212> TYPE: PRT
<213> ORGANISM: artificial sequence
<220> FEATURE:
<223> OTHER INFORMATION: Synthetic construct

<400> SEQUENCE: 106

Asp Arg His Lys Ser Lys Tyr Ser Ser Thr Lys Ser
1               5                   10

<210> SEQ ID NO 107
<211> LENGTH: 12
<212> TYPE: PRT
<213> ORGANISM: artificial sequence
<220> FEATURE:
<223> OTHER INFORMATION: Synthetic construct

<400> SEQUENCE: 107

Lys Asn Phe Pro Gln Gln Lys Glu Phe Pro Leu Ser
1               5                   10

<210> SEQ ID NO 108
<211> LENGTH: 12
<212> TYPE: PRT
<213> ORGANISM: artificial sequence
<220> FEATURE:
<223> OTHER INFORMATION: Synthetic construct

<400> SEQUENCE: 108

Gln Arg Asn Ser Pro Pro Ala Met Ser Arg Arg Asp
1               5                   10

<210> SEQ ID NO 109
<211> LENGTH: 12
<212> TYPE: PRT
<213> ORGANISM: artificial sequence
<220> FEATURE:
<223> OTHER INFORMATION: Synthetic construct

<400> SEQUENCE: 109

Thr Arg Lys Pro Asn Met Pro His Gly Gln Tyr Leu
1               5                   10

<210> SEQ ID NO 110
<211> LENGTH: 12
<212> TYPE: PRT
<213> ORGANISM: artificial sequence
<220> FEATURE:
<223> OTHER INFORMATION: Synthetic construct

<400> SEQUENCE: 110

Lys Pro Pro His Leu Ala Lys Leu Pro Phe Thr Thr
1               5                   10

<210> SEQ ID NO 111
<211> LENGTH: 12
<212> TYPE: PRT
<213> ORGANISM: artificial sequence
<220> FEATURE:
<223> OTHER INFORMATION: Synthetic construct

<400> SEQUENCE: 111

Asn Lys Arg Pro Pro Thr Ser His Arg Ile His Ala
1               5                   10

<210> SEQ ID NO 112
<211> LENGTH: 12
<212> TYPE: PRT
<213> ORGANISM: artificial sequence
<220> FEATURE:
<223> OTHER INFORMATION: Synthetic construct

<400> SEQUENCE: 112

Asn Leu Pro Arg Tyr Gln Pro Pro Cys Lys Pro Leu
1               5                   10

<210> SEQ ID NO 113
<211> LENGTH: 12
<212> TYPE: PRT
<213> ORGANISM: artificial sequence
<220> FEATURE:
<223> OTHER INFORMATION: Synthetic construct

<400> SEQUENCE: 113

Arg Pro Pro Trp Lys Lys Pro Ile Pro Pro Ser Glu
1               5                   10

<210> SEQ ID NO 114
<211> LENGTH: 12
<212> TYPE: PRT
<213> ORGANISM: artificial sequence
<220> FEATURE:
<223> OTHER INFORMATION: Synthetic construct

<400> SEQUENCE: 114

Arg Gln Arg Pro Lys Asp His Phe Phe Ser Arg Pro
1               5                   10

<210> SEQ ID NO 115
<211> LENGTH: 12
<212> TYPE: PRT
<213> ORGANISM: artificial sequence
<220> FEATURE:
<223> OTHER INFORMATION: Synthetic construct
<220> FEATURE:
<221> NAME/KEY: MISC_FEATURE
<222> LOCATION: (6)..(6)
<223> OTHER INFORMATION: Xaa = Thr or Pro
<220> FEATURE:
<221> NAME/KEY: MISC_FEATURE
<222> LOCATION: (12)..(12)
<223> OTHER INFORMATION: Xaa = Thr or Pro

<400> SEQUENCE: 115

Ser Val Pro Asn Lys Xaa Val Thr Val Asp Gly Xaa
1               5                   10

<210> SEQ ID NO 116
<211> LENGTH: 12
<212> TYPE: PRT
<213> ORGANISM: artificial sequence
<220> FEATURE:
<223> OTHER INFORMATION: Synthetic construct

<400> SEQUENCE: 116

Thr Thr Lys Trp Arg His Arg Ala Pro Val Ser Pro
1               5                   10

<210> SEQ ID NO 117
<211> LENGTH: 12
<212> TYPE: PRT
<213> ORGANISM: artificial sequence
<220> FEATURE:
<223> OTHER INFORMATION: Synthetic construct -continued

```
<400> SEQUENCE: 117

Trp Leu Gly Lys Asn Arg Ile Lys Pro Arg Ala Ser
1               5                   10

<210> SEQ ID NO 118
<211> LENGTH: 12
<212> TYPE: PRT
<213> ORGANISM: artificial sequence
<220> FEATURE:
<223> OTHER INFORMATION: Synthetic construct

<400> SEQUENCE: 118

Ser Asn Phe Lys Thr Pro Leu Pro Leu Thr Gln Ser
1               5                   10

<210> SEQ ID NO 119
<211> LENGTH: 12
<212> TYPE: PRT
<213> ORGANISM: artificial sequence
<220> FEATURE:
<223> OTHER INFORMATION: Synthetic construct

<400> SEQUENCE: 119

Ser Val Ser Val Gly Met Lys Pro Ser Pro Arg Pro
1               5                   10

<210> SEQ ID NO 120
<211> LENGTH: 7
<212> TYPE: PRT
<213> ORGANISM: artificial sequence
<220> FEATURE:
<223> OTHER INFORMATION: Synthetic construct

<400> SEQUENCE: 120

Asp Leu His Thr Val Tyr His
1               5

<210> SEQ ID NO 121
<211> LENGTH: 7
<212> TYPE: PRT
<213> ORGANISM: artificial sequence
<220> FEATURE:
<223> OTHER INFORMATION: Synthetic construct

<400> SEQUENCE: 121

His Ile Lys Pro Pro Thr Arg
1               5

<210> SEQ ID NO 122
<211> LENGTH: 7
<212> TYPE: PRT
<213> ORGANISM: artificial sequence
<220> FEATURE:
<223> OTHER INFORMATION: Synthetic construct

<400> SEQUENCE: 122

His Pro Val Trp Pro Ala Ile
1               5

<210> SEQ ID NO 123
<211> LENGTH: 7
<212> TYPE: PRT
<213> ORGANISM: artificial sequence
<220> FEATURE:
<223> OTHER INFORMATION: Synthetic construct
```

```
<400> SEQUENCE: 123

Met Pro Leu Tyr Tyr Leu Gln
1               5

<210> SEQ ID NO 124
<211> LENGTH: 26
<212> TYPE: PRT
<213> ORGANISM: artificial sequence
<220> FEATURE:
<223> OTHER INFORMATION: Synthetic construct

<400> SEQUENCE: 124

His Leu Thr Val Pro Trp Arg Gly Gly Gly Ser Ala Val Pro Phe Tyr
1               5                   10                  15

Ser His Ser Gln Ile Thr Leu Pro Asn His
            20                  25

<210> SEQ ID NO 125
<211> LENGTH: 41
<212> TYPE: PRT
<213> ORGANISM: artificial sequence
<220> FEATURE:
<223> OTHER INFORMATION: Synthetic construct

<400> SEQUENCE: 125

Gly Pro His Asp Thr Ser Ser Gly Gly Val Arg Pro Asn Leu His His
1               5                   10                  15

Thr Ser Lys Lys Glu Lys Arg Glu Asn Arg Lys Val Pro Phe Tyr Ser
            20                  25                  30

His Ser Val Thr Ser Arg Gly Asn Val
            35                  40

<210> SEQ ID NO 126
<211> LENGTH: 7
<212> TYPE: PRT
<213> ORGANISM: artificial sequence
<220> FEATURE:
<223> OTHER INFORMATION: Synthetic construct

<400> SEQUENCE: 126

Lys His Pro Thr Tyr Arg Gln
1               5

<210> SEQ ID NO 127
<211> LENGTH: 7
<212> TYPE: PRT
<213> ORGANISM: artificial sequence
<220> FEATURE:
<223> OTHER INFORMATION: Synthetic construct

<400> SEQUENCE: 127

His Pro Met Ser Ala Pro Arg
1               5

<210> SEQ ID NO 128
<211> LENGTH: 7
<212> TYPE: PRT
<213> ORGANISM: artificial sequence
<220> FEATURE:
<223> OTHER INFORMATION: Synthetic construct

<400> SEQUENCE: 128

Met Pro Lys Tyr Tyr Leu Gln
1               5
```

```
<210> SEQ ID NO 129
<211> LENGTH: 7
<212> TYPE: PRT
<213> ORGANISM: artificial sequence
<220> FEATURE:
<223> OTHER INFORMATION: Synthetic construct

<400> SEQUENCE: 129

Met His Ala His Ser Ile Ala
1               5

<210> SEQ ID NO 130
<211> LENGTH: 12
<212> TYPE: PRT
<213> ORGANISM: artificial sequence
<220> FEATURE:
<223> OTHER INFORMATION: Synthetic construct

<400> SEQUENCE: 130

Ala Lys Pro Ile Ser Gln His Leu Gln Arg Gly Ser
1               5                   10

<210> SEQ ID NO 131
<211> LENGTH: 12
<212> TYPE: PRT
<213> ORGANISM: artificial sequence
<220> FEATURE:
<223> OTHER INFORMATION: Synthetic construct

<400> SEQUENCE: 131

Ala Pro Pro Thr Pro Ala Ala Ala Ser Ala Thr Thr
1               5                   10

<210> SEQ ID NO 132
<211> LENGTH: 12
<212> TYPE: PRT
<213> ORGANISM: artificial sequence
<220> FEATURE:
<223> OTHER INFORMATION: Synthetic construct

<400> SEQUENCE: 132

Asp Pro Thr Glu Gly Ala Arg Arg Thr Ile Met Thr
1               5                   10

<210> SEQ ID NO 133
<211> LENGTH: 12
<212> TYPE: PRT
<213> ORGANISM: artificial sequence
<220> FEATURE:
<223> OTHER INFORMATION: Synthetic construct

<400> SEQUENCE: 133

Leu Asp Thr Ser Phe Pro Pro Val Pro Phe His Ala
1               5                   10

<210> SEQ ID NO 134
<211> LENGTH: 12
<212> TYPE: PRT
<213> ORGANISM: artificial sequence
<220> FEATURE:
<223> OTHER INFORMATION: Synthetic construct

<400> SEQUENCE: 134

Leu Asp Thr Ser Phe His Gln Val Pro Phe His Gln
1               5                   10
```

```
<210> SEQ ID NO 135
<211> LENGTH: 11
<212> TYPE: PRT
<213> ORGANISM: artificial sequence
<220> FEATURE:
<223> OTHER INFORMATION: Synthetic construct

<400> SEQUENCE: 135

Leu Pro Arg Ile Ala Asn Thr Trp Ser Pro Ser
1               5                   10

<210> SEQ ID NO 136
<211> LENGTH: 12
<212> TYPE: PRT
<213> ORGANISM: artificial sequence
<220> FEATURE:
<223> OTHER INFORMATION: Synthetic construct

<400> SEQUENCE: 136

Arg Thr Asn Ala Ala Asp His Pro Ala Ala Val Thr
1               5                   10

<210> SEQ ID NO 137
<211> LENGTH: 12
<212> TYPE: PRT
<213> ORGANISM: artificial sequence
<220> FEATURE:
<223> OTHER INFORMATION: Synthetic construct

<400> SEQUENCE: 137

Ser Leu Asn Trp Val Thr Ile Pro Gly Pro Lys Ile
1               5                   10

<210> SEQ ID NO 138
<211> LENGTH: 12
<212> TYPE: PRT
<213> ORGANISM: artificial sequence
<220> FEATURE:
<223> OTHER INFORMATION: Synthetic construct

<400> SEQUENCE: 138

Thr Asp Met Gln Ala Pro Thr Lys Ser Tyr Ser Asn
1               5                   10

<210> SEQ ID NO 139
<211> LENGTH: 12
<212> TYPE: PRT
<213> ORGANISM: artificial sequence
<220> FEATURE:
<223> OTHER INFORMATION: Synthetic construct

<400> SEQUENCE: 139

Thr Ile Met Thr Lys Ser Pro Ser Leu Ser Cys Gly
1               5                   10

<210> SEQ ID NO 140
<211> LENGTH: 12
<212> TYPE: PRT
<213> ORGANISM: artificial sequence
<220> FEATURE:
<223> OTHER INFORMATION: Synthetic construct

<400> SEQUENCE: 140

Thr Pro Ala Leu Asp Gly Leu Arg Gln Pro Leu Arg
1               5                   10

<210> SEQ ID NO 141
```

<211> LENGTH: 12
<212> TYPE: PRT
<213> ORGANISM: artificial sequence
<220> FEATURE:
<223> OTHER INFORMATION: Synthetic construct

<400> SEQUENCE: 141

Thr Tyr Pro Ala Ser Arg Leu Pro Leu Leu Ala Pro
1               5                   10

<210> SEQ ID NO 142
<211> LENGTH: 12
<212> TYPE: PRT
<213> ORGANISM: artificial sequence
<220> FEATURE:
<223> OTHER INFORMATION: Synthetic construct

<400> SEQUENCE: 142

Ala Lys Thr His Lys His Pro Ala Pro Ser Tyr Ser
1               5                   10

<210> SEQ ID NO 143
<211> LENGTH: 12
<212> TYPE: PRT
<213> ORGANISM: artificial sequence
<220> FEATURE:
<223> OTHER INFORMATION: Synthetic construct

<400> SEQUENCE: 143

Thr Asp Pro Thr Pro Phe Ser Ile Ser Pro Glu Arg
1               5                   10

<210> SEQ ID NO 144
<211> LENGTH: 12
<212> TYPE: PRT
<213> ORGANISM: artificial sequence
<220> FEATURE:
<223> OTHER INFORMATION: Synthetic construct

<400> SEQUENCE: 144

Ser Gln Asn Trp Gln Asp Ser Thr Ser Tyr Ser Asn
1               5                   10

<210> SEQ ID NO 145
<211> LENGTH: 12
<212> TYPE: PRT
<213> ORGANISM: artificial sequence
<220> FEATURE:
<223> OTHER INFORMATION: Synthetic construct

<400> SEQUENCE: 145

Trp His Asp Lys Pro Gln Asn Ser Ser Lys Ser Thr
1               5                   10

<210> SEQ ID NO 146
<211> LENGTH: 12
<212> TYPE: PRT
<213> ORGANISM: artificial sequence
<220> FEATURE:
<223> OTHER INFORMATION: Synthetic construct

<400> SEQUENCE: 146

Leu Asp Val Glu Ser Tyr Lys Gly Thr Ser Met Pro
1               5                   10

<210> SEQ ID NO 147
<211> LENGTH: 7

```
<212> TYPE: PRT
<213> ORGANISM: artificial sequence
<220> FEATURE:
<223> OTHER INFORMATION: Synthetic construct

<400> SEQUENCE: 147

Asn Thr Pro Lys Glu Asn Trp
1               5

<210> SEQ ID NO 148
<211> LENGTH: 7
<212> TYPE: PRT
<213> ORGANISM: artificial sequence
<220> FEATURE:
<223> OTHER INFORMATION: Synthetic construct

<400> SEQUENCE: 148

Asn Thr Pro Ala Ser Asn Arg
1               5

<210> SEQ ID NO 149
<211> LENGTH: 7
<212> TYPE: PRT
<213> ORGANISM: artificial sequence
<220> FEATURE:
<223> OTHER INFORMATION: Synthetic construct

<400> SEQUENCE: 149

Pro Arg Gly Met Leu Ser Thr
1               5

<210> SEQ ID NO 150
<211> LENGTH: 7
<212> TYPE: PRT
<213> ORGANISM: artificial sequence
<220> FEATURE:
<223> OTHER INFORMATION: Synthetic construct

<400> SEQUENCE: 150

Pro Pro Thr Tyr Leu Ser Thr
1               5

<210> SEQ ID NO 151
<211> LENGTH: 12
<212> TYPE: PRT
<213> ORGANISM: artificial sequence
<220> FEATURE:
<223> OTHER INFORMATION: Synthetic construct

<400> SEQUENCE: 151

Thr Ile Pro Thr His Arg Gln His Asp Tyr Arg Ser
1               5                   10

<210> SEQ ID NO 152
<211> LENGTH: 7
<212> TYPE: PRT
<213> ORGANISM: artificial sequence
<220> FEATURE:
<223> OTHER INFORMATION: Synthetic construct

<400> SEQUENCE: 152

Thr Pro Pro Thr His Arg Leu
1               5

<210> SEQ ID NO 153
<211> LENGTH: 7
<212> TYPE: PRT
```

```
<213> ORGANISM: artificial sequence
<220> FEATURE:
<223> OTHER INFORMATION: Synthetic construct

<400> SEQUENCE: 153

Leu Pro Thr Met Ser Thr Pro
1               5

<210> SEQ ID NO 154
<211> LENGTH: 7
<212> TYPE: PRT
<213> ORGANISM: artificial sequence
<220> FEATURE:
<223> OTHER INFORMATION: Synthetic construct

<400> SEQUENCE: 154

Leu Gly Thr Asn Ser Thr Pro
1               5

<210> SEQ ID NO 155
<211> LENGTH: 12
<212> TYPE: PRT
<213> ORGANISM: artificial sequence
<220> FEATURE:
<223> OTHER INFORMATION: Synthetic construct

<400> SEQUENCE: 155

Thr Pro Leu Thr Gly Ser Thr Asn Leu Leu Ser Ser
1               5                   10

<210> SEQ ID NO 156
<211> LENGTH: 7
<212> TYPE: PRT
<213> ORGANISM: artificial sequence
<220> FEATURE:
<223> OTHER INFORMATION: Synthetic construct

<400> SEQUENCE: 156

Thr Pro Leu Thr Lys Glu Thr
1               5

<210> SEQ ID NO 157
<211> LENGTH: 7
<212> TYPE: PRT
<213> ORGANISM: artificial sequence
<220> FEATURE:
<223> OTHER INFORMATION: Synthetic construct

<400> SEQUENCE: 157

Lys Gln Ser His Asn Pro Pro
1               5

<210> SEQ ID NO 158
<211> LENGTH: 7
<212> TYPE: PRT
<213> ORGANISM: artificial sequence
<220> FEATURE:
<223> OTHER INFORMATION: Synthetic construct

<400> SEQUENCE: 158

Gln Gln Ser His Asn Pro Pro
1               5

<210> SEQ ID NO 159
<211> LENGTH: 7
<212> TYPE: PRT
<213> ORGANISM: artificial sequence
```

```
<220> FEATURE:
<223> OTHER INFORMATION: Synthetic construct

<400> SEQUENCE: 159

Thr Gln Pro His Asn Pro Pro
1               5

<210> SEQ ID NO 160
<211> LENGTH: 12
<212> TYPE: PRT
<213> ORGANISM: artificial sequence
<220> FEATURE:
<223> OTHER INFORMATION: Synthetic construct

<400> SEQUENCE: 160

Ser Thr Asn Leu Leu Arg Thr Ser Thr Val His Pro
1               5                   10

<210> SEQ ID NO 161
<211> LENGTH: 12
<212> TYPE: PRT
<213> ORGANISM: artificial sequence
<220> FEATURE:
<223> OTHER INFORMATION: Synthetic construct

<400> SEQUENCE: 161

His Thr Gln Pro Ser Tyr Ser Ser Thr Asn Leu Phe
1               5                   10

<210> SEQ ID NO 162
<211> LENGTH: 7
<212> TYPE: PRT
<213> ORGANISM: artificial sequence
<220> FEATURE:
<223> OTHER INFORMATION: Synthetic construct

<400> SEQUENCE: 162

Ser Leu Leu Ser Ser His Ala
1               5

<210> SEQ ID NO 163
<211> LENGTH: 12
<212> TYPE: PRT
<213> ORGANISM: artificial sequence
<220> FEATURE:
<223> OTHER INFORMATION: Synthetic construct

<400> SEQUENCE: 163

Gln Gln Ser Ser Ile Ser Leu Ser Ser His Ala Val
1               5                   10

<210> SEQ ID NO 164
<211> LENGTH: 7
<212> TYPE: PRT
<213> ORGANISM: artificial sequence
<220> FEATURE:
<223> OTHER INFORMATION: Synthetic construct

<400> SEQUENCE: 164

Asn Ala Ser Pro Ser Ser Leu
1               5

<210> SEQ ID NO 165
<211> LENGTH: 7
<212> TYPE: PRT
<213> ORGANISM: artificial sequence
<220> FEATURE:
```

<223> OTHER INFORMATION: Synthetic construct

<400> SEQUENCE: 165

His Ser Pro Ser Ser Leu Arg
1               5

<210> SEQ ID NO 166
<211> LENGTH: 7
<212> TYPE: PRT
<213> ORGANISM: artificial sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: X= H, R or N
<220> FEATURE:
<221> NAME/KEY: MISC_FEATURE
<222> LOCATION: (2)..(2)
<223> OTHER INFORMATION: X= His, Arg or Asn

<400> SEQUENCE: 166

Lys Xaa Ser His His Thr His
1               5

<210> SEQ ID NO 167
<211> LENGTH: 7
<212> TYPE: PRT
<213> ORGANISM: artificial sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: X = H, R or N
<220> FEATURE:
<221> NAME/KEY: MISC_FEATURE
<222> LOCATION: (2)..(2)
<223> OTHER INFORMATION: X = His, Arg or Asn

<400> SEQUENCE: 167

Glu Xaa Ser His His Thr His
1               5

<210> SEQ ID NO 168
<211> LENGTH: 12
<212> TYPE: PRT
<213> ORGANISM: artificial sequence
<220> FEATURE:
<223> OTHER INFORMATION: Synthetic construct

<400> SEQUENCE: 168

Ser His His Thr His Tyr Gly Gln Pro Gly Pro Val
1               5                   10

<210> SEQ ID NO 169
<211> LENGTH: 7
<212> TYPE: PRT
<213> ORGANISM: artificial sequence
<220> FEATURE:
<223> OTHER INFORMATION: Synthetic construct

<400> SEQUENCE: 169

Leu Glu Ser Thr Ser Leu Leu
1               5

<210> SEQ ID NO 170
<211> LENGTH: 7
<212> TYPE: PRT

```
<213> ORGANISM: artificial sequence
<220> FEATURE:
<223> OTHER INFORMATION: Synthetic construct

<400> SEQUENCE: 170

Asp Leu Thr Leu Pro Phe His
1               5

<210> SEQ ID NO 171
<211> LENGTH: 8
<212> TYPE: PRT
<213> ORGANISM: artificial sequence
<220> FEATURE:
<223> OTHER INFORMATION: Synthetic construct

<400> SEQUENCE: 171

Arg Thr Asn Ala Ala Asp His Pro
1               5

<210> SEQ ID NO 172
<211> LENGTH: 12
<212> TYPE: PRT
<213> ORGANISM: artificial sequence
<220> FEATURE:
<223> OTHER INFORMATION: Synthetic construct

<400> SEQUENCE: 172

Ile Pro Trp Trp Asn Ile Arg Ala Pro Leu Asn Ala
1               5                   10

<210> SEQ ID NO 173
<211> LENGTH: 18
<212> TYPE: PRT
<213> ORGANISM: artificial sequence
<220> FEATURE:
<223> OTHER INFORMATION: Synthetic construct

<400> SEQUENCE: 173

Glu Gln Ile Ser Gly Ser Leu Val Ala Ala Pro Trp Glu Gly Glu Gly
1               5                   10                  15

Glu Arg

<210> SEQ ID NO 174
<211> LENGTH: 12
<212> TYPE: PRT
<213> ORGANISM: artificial sequence
<220> FEATURE:
<223> OTHER INFORMATION: synthetic hair-binding peptide

<400> SEQUENCE: 174

Thr Pro Pro Glu Leu Leu His Gly Ala Pro Arg Ser
1               5                   10

<210> SEQ ID NO 175
<211> LENGTH: 18
<212> TYPE: PRT
<213> ORGANISM: artificial sequence
<220> FEATURE:
<223> OTHER INFORMATION: Synthetic construct

<400> SEQUENCE: 175

Leu Asp Thr Ser Phe His Gln Val Pro Phe His Gln Lys Arg Lys Arg
1               5                   10                  15

Lys Asp
```

```
<210> SEQ ID NO 176
<211> LENGTH: 18
<212> TYPE: PRT
<213> ORGANISM: artificial sequence
<220> FEATURE:
<223> OTHER INFORMATION: Synthetic construct

<400> SEQUENCE: 176

Glu Gln Ile Ser Gly Ser Leu Val Ala Ala Pro Trp Lys Arg Lys Arg
1               5                   10                  15

Lys Asp

<210> SEQ ID NO 177
<211> LENGTH: 18
<212> TYPE: PRT
<213> ORGANISM: artificial sequence
<220> FEATURE:
<223> OTHER INFORMATION: Synthetic construct

<400> SEQUENCE: 177

Thr Pro Pro Glu Leu Leu His Gly Asp Pro Arg Ser Lys Arg Lys Arg
1               5                   10                  15

Lys Asp

<210> SEQ ID NO 178
<211> LENGTH: 13
<212> TYPE: PRT
<213> ORGANISM: artificial sequence
<220> FEATURE:
<223> OTHER INFORMATION: Synthetic construct

<400> SEQUENCE: 178

Asn Thr Ser Gln Leu Ser Thr Glu Gly Glu Gly Glu Asp
1               5                   10

<210> SEQ ID NO 179
<211> LENGTH: 13
<212> TYPE: PRT
<213> ORGANISM: artificial sequence
<220> FEATURE:
<223> OTHER INFORMATION: Synthetic construct

<400> SEQUENCE: 179

Thr Pro Pro Glu Leu Leu His Gly Asp Pro Arg Ser Cys
1               5                   10

<210> SEQ ID NO 180
<211> LENGTH: 20
<212> TYPE: PRT
<213> ORGANISM: artificial sequence
<220> FEATURE:
<223> OTHER INFORMATION: synthetic hair-binding peptide

<400> SEQUENCE: 180

His Ile Asn Lys Thr Asn Pro His Gln Gly Asn His His Ser Glu Lys
1               5                   10                  15

Thr Gln Arg Gln
            20

<210> SEQ ID NO 181
<211> LENGTH: 15
<212> TYPE: PRT
<213> ORGANISM: artificial sequence
<220> FEATURE:
<223> OTHER INFORMATION: Synthetic construct
```

```
<400> SEQUENCE: 181

His Ala His Lys Asn Gln Lys Glu Thr His Gln Arg His Ala Ala
1               5                   10                  15

<210> SEQ ID NO 182
<211> LENGTH: 15
<212> TYPE: PRT
<213> ORGANISM: artificial sequence
<220> FEATURE:
<223> OTHER INFORMATION: Synthetic construct

<400> SEQUENCE: 182

His Glu His Lys Asn Gln Lys Glu Thr His Gln Arg His Ala Ala
1               5                   10                  15

<210> SEQ ID NO 183
<211> LENGTH: 20
<212> TYPE: PRT
<213> ORGANISM: artificial sequence
<220> FEATURE:
<223> OTHER INFORMATION: Synthetic construct

<400> SEQUENCE: 183

His Asn His Met Gln Glu Arg Tyr Thr Glu Pro Gln His Ser Pro Ser
1               5                   10                  15

Val Asn Gly Leu
            20

<210> SEQ ID NO 184
<211> LENGTH: 17
<212> TYPE: PRT
<213> ORGANISM: artificial sequence
<220> FEATURE:
<223> OTHER INFORMATION: Synthetic construct

<400> SEQUENCE: 184

Thr His Ser Thr His Asn His Gly Ser Pro Arg His Thr Asn Ala Asp
1               5                   10                  15

Ala

<210> SEQ ID NO 185
<211> LENGTH: 20
<212> TYPE: PRT
<213> ORGANISM: artificial sequence
<220> FEATURE:
<223> OTHER INFORMATION: synthetic hair-binding peptide

<400> SEQUENCE: 185

Gly Ser Cys Val Asp Thr His Lys Ala Asp Ser Cys Val Ala Asn Asn
1               5                   10                  15

Gly Pro Ala Thr
            20

<210> SEQ ID NO 186
<211> LENGTH: 20
<212> TYPE: PRT
<213> ORGANISM: artificial sequence
<220> FEATURE:
<223> OTHER INFORMATION: synthetic hair-binding peptide

<400> SEQUENCE: 186

Ala Gln Ser Gln Leu Pro Asp Lys His Ser Gly Leu His Glu Arg Ala
1               5                   10                  15

Pro Gln Arg Tyr
```

```
                        20

<210> SEQ ID NO 187
<211> LENGTH: 20
<212> TYPE: PRT
<213> ORGANISM: artificial sequence
<220> FEATURE:
<223> OTHER INFORMATION: Synthetic construct

<400> SEQUENCE: 187

Ala Gln Ser Gln Leu Pro Ala Lys His Ser Gly Leu His Glu Arg Ala
1               5                   10                  15

Pro Gln Arg Tyr
            20

<210> SEQ ID NO 188
<211> LENGTH: 20
<212> TYPE: PRT
<213> ORGANISM: artificial sequence
<220> FEATURE:
<223> OTHER INFORMATION: Synthetic construct

<400> SEQUENCE: 188

Ala Gln Ser Gln Leu Pro Glu Lys His Ser Gly Leu His Glu Arg Ala
1               5                   10                  15

Pro Gln Arg Tyr
            20

<210> SEQ ID NO 189
<211> LENGTH: 20
<212> TYPE: PRT
<213> ORGANISM: artificial sequence
<220> FEATURE:
<223> OTHER INFORMATION: synthetic hair-binding peptide

<400> SEQUENCE: 189

Thr Asp Met Met His Asn His Ser Asp Asn Ser Pro Pro His Arg Arg
1               5                   10                  15

Ser Pro Arg Asn
            20

<210> SEQ ID NO 190
<211> LENGTH: 20
<212> TYPE: PRT
<213> ORGANISM: artificial sequence
<220> FEATURE:
<223> OTHER INFORMATION: synthetic hair-binding peptide

<400> SEQUENCE: 190

Thr Pro Pro Glu Leu Ala His Thr Pro His His Leu Ala Gln Thr Arg
1               5                   10                  15

Leu Thr Asp Arg
            20

<210> SEQ ID NO 191
<211> LENGTH: 12
<212> TYPE: PRT
<213> ORGANISM: artificial sequence
<220> FEATURE:
<223> OTHER INFORMATION: Synthetic construct

<400> SEQUENCE: 191

Arg Leu Leu Arg Leu Leu Arg Leu Leu Arg Leu Leu
1               5                   10
```

```
<210> SEQ ID NO 192
<211> LENGTH: 12
<212> TYPE: PRT
<213> ORGANISM: artificial sequence
<220> FEATURE:
<223> OTHER INFORMATION: Synthetic construct

<400> SEQUENCE: 192

Thr Pro Pro Glu Leu Leu His Gly Glu Pro Arg Ser
1               5                   10

<210> SEQ ID NO 193
<211> LENGTH: 12
<212> TYPE: PRT
<213> ORGANISM: artificial sequence
<220> FEATURE:
<223> OTHER INFORMATION: Synthetic construct

<400> SEQUENCE: 193

Thr Pro Pro Glu Leu Leu His Gly Ala Pro Arg Ser
1               5                   10

<210> SEQ ID NO 194
<211> LENGTH: 12
<212> TYPE: PRT
<213> ORGANISM: artificial sequence
<220> FEATURE:
<223> OTHER INFORMATION: Synthetic construct

<400> SEQUENCE: 194

Glu Gln Ile Ser Gly Ser Leu Val Ala Ala Pro Trp
1               5                   10

<210> SEQ ID NO 195
<211> LENGTH: 12
<212> TYPE: PRT
<213> ORGANISM: artificial sequence
<220> FEATURE:
<223> OTHER INFORMATION: Synthetic construct

<400> SEQUENCE: 195

Asn Glu Val Pro Ala Arg Asn Ala Pro Trp Leu Val
1               5                   10

<210> SEQ ID NO 196
<211> LENGTH: 13
<212> TYPE: PRT
<213> ORGANISM: artificial sequence
<220> FEATURE:
<223> OTHER INFORMATION: Synthetic construct

<400> SEQUENCE: 196

Asn Ser Pro Gly Tyr Gln Ala Asp Ser Val Ala Ile Gly
1               5                   10

<210> SEQ ID NO 197
<211> LENGTH: 12
<212> TYPE: PRT
<213> ORGANISM: artificial sequence
<220> FEATURE:
<223> OTHER INFORMATION: Synthetic construct

<400> SEQUENCE: 197

Ala Lys Pro Ile Ser Gln His Leu Gln Arg Gly Ser
1               5                   10
```

-continued

```
<210> SEQ ID NO 198
<211> LENGTH: 12
<212> TYPE: PRT
<213> ORGANISM: artificial sequence
<220> FEATURE:
<223> OTHER INFORMATION: Synthetic construct

<400> SEQUENCE: 198

Leu Asp Thr Ser Phe Pro Pro Val Pro Phe His Ala
1               5                   10

<210> SEQ ID NO 199
<211> LENGTH: 12
<212> TYPE: PRT
<213> ORGANISM: artificial sequence
<220> FEATURE:
<223> OTHER INFORMATION: Synthetic construct

<400> SEQUENCE: 199

Ser Leu Asn Trp Val Thr Ile Pro Gly Pro Lys Ile
1               5                   10

<210> SEQ ID NO 200
<211> LENGTH: 12
<212> TYPE: PRT
<213> ORGANISM: artificial sequence
<220> FEATURE:
<223> OTHER INFORMATION: Synthetic construct

<400> SEQUENCE: 200

Thr Gln Asp Ser Ala Gln Lys Ser Pro Ser Pro Leu
1               5                   10

<210> SEQ ID NO 201
<211> LENGTH: 12
<212> TYPE: PRT
<213> ORGANISM: artificial sequence
<220> FEATURE:
<223> OTHER INFORMATION: Synthetic construct

<400> SEQUENCE: 201

Lys Glu Leu Gln Thr Arg Asn Val Val Gln Arg Glu
1               5                   10

<210> SEQ ID NO 202
<211> LENGTH: 12
<212> TYPE: PRT
<213> ORGANISM: artificial sequence
<220> FEATURE:
<223> OTHER INFORMATION: Synthetic construct

<400> SEQUENCE: 202

Gln Arg Asn Ser Pro Pro Ala Met Ser Arg Arg Asp
1               5                   10

<210> SEQ ID NO 203
<211> LENGTH: 12
<212> TYPE: PRT
<213> ORGANISM: artificial sequence
<220> FEATURE:
<223> OTHER INFORMATION: Synthetic construct

<400> SEQUENCE: 203

Thr Pro Thr Ala Asn Gln Phe Thr Gln Ser Val Pro
1               5                   10

<210> SEQ ID NO 204
```

```
<211> LENGTH: 12
<212> TYPE: PRT
<213> ORGANISM: artificial sequence
<220> FEATURE:
<223> OTHER INFORMATION: Synthetic construct

<400> SEQUENCE: 204

Ala Ala Gly Leu Ser Gln Lys His Glu Arg Asn Arg
1               5                   10

<210> SEQ ID NO 205
<211> LENGTH: 12
<212> TYPE: PRT
<213> ORGANISM: artificial sequence
<220> FEATURE:
<223> OTHER INFORMATION: Synthetic construct

<400> SEQUENCE: 205

Glu Thr Val His Gln Thr Pro Leu Ser Asp Arg Pro
1               5                   10

<210> SEQ ID NO 206
<211> LENGTH: 12
<212> TYPE: PRT
<213> ORGANISM: artificial sequence
<220> FEATURE:
<223> OTHER INFORMATION: Synthetic construct

<400> SEQUENCE: 206

Lys Asn Phe Pro Gln Gln Lys Glu Phe Pro Leu Ser
1               5                   10

<210> SEQ ID NO 207
<211> LENGTH: 12
<212> TYPE: PRT
<213> ORGANISM: artificial sequence
<220> FEATURE:
<223> OTHER INFORMATION: Synthetic construct

<400> SEQUENCE: 207

Leu Pro Ala Leu His Ile Gln Arg His Pro Arg Met
1               5                   10

<210> SEQ ID NO 208
<211> LENGTH: 12
<212> TYPE: PRT
<213> ORGANISM: artificial sequence
<220> FEATURE:
<223> OTHER INFORMATION: Synthetic construct

<400> SEQUENCE: 208

Gln Pro Ser His Ser Gln Ser His Asn Leu Arg Ser
1               5                   10

<210> SEQ ID NO 209
<211> LENGTH: 12
<212> TYPE: PRT
<213> ORGANISM: artificial sequence
<220> FEATURE:
<223> OTHER INFORMATION: Synthetic construct

<400> SEQUENCE: 209

Arg Gly Ser Gln Lys Ser Lys Pro Pro Arg Pro Pro
1               5                   10

<210> SEQ ID NO 210
<211> LENGTH: 12
```

```
<212> TYPE: PRT
<213> ORGANISM: artificial sequence
<220> FEATURE:
<223> OTHER INFORMATION: Synthetic construct

<400> SEQUENCE: 210

Thr His Thr Gln Lys Thr Pro Leu Leu Tyr Tyr His
1               5                   10

<210> SEQ ID NO 211
<211> LENGTH: 12
<212> TYPE: PRT
<213> ORGANISM: artificial sequence
<220> FEATURE:
<223> OTHER INFORMATION: Synthetic construct

<400> SEQUENCE: 211

Thr Lys Gly Ser Ser Gln Ala Ile Leu Lys Ser Thr
1               5                   10

<210> SEQ ID NO 212
<211> LENGTH: 7
<212> TYPE: PRT
<213> ORGANISM: artificial sequence
<220> FEATURE:
<223> OTHER INFORMATION: Synthetic construct

<400> SEQUENCE: 212

Thr Ala Ala Thr Thr Ser Pro
1               5

<210> SEQ ID NO 213
<211> LENGTH: 7
<212> TYPE: PRT
<213> ORGANISM: artificial sequence
<220> FEATURE:
<223> OTHER INFORMATION: Synthetic construct

<400> SEQUENCE: 213

Leu Gly Ile Pro Gln Asn Leu
1               5

<210> SEQ ID NO 214
<211> LENGTH: 20
<212> TYPE: PRT
<213> ORGANISM: artificial sequence
<220> FEATURE:
<223> OTHER INFORMATION: Synthetic construct

<400> SEQUENCE: 214

Thr His Ser Thr His Asn His Gly Ser Pro Arg His Thr Asn Ala Asp
1               5                   10                  15

Ala Gly Asn Pro
            20

<210> SEQ ID NO 215
<211> LENGTH: 20
<212> TYPE: PRT
<213> ORGANISM: artificial sequence
<220> FEATURE:
<223> OTHER INFORMATION: Synthetic construct

<400> SEQUENCE: 215

Gln Gln His Lys Val His His Gln Asn Pro Asp Arg Ser Thr Gln Asp
1               5                   10                  15

Ala His His Ser
```

```
<210> SEQ ID NO 216
<211> LENGTH: 15
<212> TYPE: PRT
<213> ORGANISM: artificial sequence
<220> FEATURE:
<223> OTHER INFORMATION: Synthetic construct

<400> SEQUENCE: 216

His His Gly Thr His His Asn Ala Thr Lys Gln Lys Asn His Val
1               5                   10                  15

<210> SEQ ID NO 217
<211> LENGTH: 15
<212> TYPE: PRT
<213> ORGANISM: artificial sequence
<220> FEATURE:
<223> OTHER INFORMATION: Synthetic construct

<400> SEQUENCE: 217

Ser Thr Leu His Lys Tyr Lys Ser Gln Asp Pro Thr Pro His His
1               5                   10                  15

<210> SEQ ID NO 218
<211> LENGTH: 12
<212> TYPE: PRT
<213> ORGANISM: artificial sequence
<220> FEATURE:
<223> OTHER INFORMATION: Synthetic construct

<400> SEQUENCE: 218

Ser Val Ser Val Gly Met Lys Pro Ser Pro Arg Pro
1               5                   10

<210> SEQ ID NO 219
<211> LENGTH: 12
<212> TYPE: PRT
<213> ORGANISM: artificial sequence
<220> FEATURE:
<223> OTHER INFORMATION: synthetic hair-binding peptide

<400> SEQUENCE: 219

Thr Pro Pro Thr Asn Val Leu Met Leu Ala Thr Lys
1               5                   10

<210> SEQ ID NO 220
<211> LENGTH: 12
<212> TYPE: PRT
<213> ORGANISM: artificial sequence
<220> FEATURE:
<223> OTHER INFORMATION: Synthetic construct

<400> SEQUENCE: 220

Thr Pro Pro Glu Leu Leu His Gly Asp Pro Arg Ser
1               5                   10

<210> SEQ ID NO 221
<211> LENGTH: 7
<212> TYPE: PRT
<213> ORGANISM: artificial sequence
<220> FEATURE:
<223> OTHER INFORMATION: synthetic hair-binding peptide

<400> SEQUENCE: 221

Asn Thr Ser Gln Leu Ser Thr
1               5
```

<210> SEQ ID NO 222
<211> LENGTH: 15
<212> TYPE: PRT
<213> ORGANISM: artificial sequence
<220> FEATURE:
<223> OTHER INFORMATION: Synthetic construct

<400> SEQUENCE: 222

Ser Thr Leu His Lys Tyr Lys Ser Gln Asp Pro Thr Pro His His
1               5                   10                  15

<210> SEQ ID NO 223
<211> LENGTH: 12
<212> TYPE: PRT
<213> ORGANISM: artificial sequence
<220> FEATURE:
<223> OTHER INFORMATION: synthetic hair-binding peptide

<400> SEQUENCE: 223

Gly Met Pro Ala Met His Trp Ile His Pro Phe Ala
1               5                   10

<210> SEQ ID NO 224
<211> LENGTH: 15
<212> TYPE: PRT
<213> ORGANISM: artificial sequence
<220> FEATURE:
<223> OTHER INFORMATION: synthetic hair-binding peptide

<400> SEQUENCE: 224

His Asp His Lys Asn Gln Lys Glu Thr His Gln Arg His Ala Ala
1               5                   10                  15

<210> SEQ ID NO 225
<211> LENGTH: 20
<212> TYPE: PRT
<213> ORGANISM: artificial sequence
<220> FEATURE:
<223> OTHER INFORMATION: Synthetic construct

<400> SEQUENCE: 225

His Asn His Met Gln Glu Arg Tyr Thr Asp Pro Gln His Ser Pro Ser
1               5                   10                  15

Val Asn Gly Leu
            20

<210> SEQ ID NO 226
<211> LENGTH: 20
<212> TYPE: PRT
<213> ORGANISM: artificial sequence
<220> FEATURE:
<223> OTHER INFORMATION: synthetic hair-binding peptide

<400> SEQUENCE: 226

Thr Ala Glu Ile Gln Ser Ser Lys Asn Pro Asn Pro His Pro Gln Arg
1               5                   10                  15

Ser Trp Thr Asn
            20

<210> SEQ ID NO 227
<211> LENGTH: 12
<212> TYPE: PRT
<213> ORGANISM: artificial sequence
<220> FEATURE:
<223> OTHER INFORMATION: Synthetic construct

```
<400> SEQUENCE: 227

Lys Arg Gly Arg His Lys Arg Pro Lys Arg His Lys
1               5                   10

<210> SEQ ID NO 228
<211> LENGTH: 7
<212> TYPE: PRT
<213> ORGANISM: artificial sequence
<220> FEATURE:
<223> OTHER INFORMATION: Synthetic construct

<400> SEQUENCE: 228

Arg Leu Leu Arg Leu Leu Arg
1               5

<210> SEQ ID NO 229
<211> LENGTH: 12
<212> TYPE: PRT
<213> ORGANISM: artificial sequence
<220> FEATURE:
<223> OTHER INFORMATION: Synthetic construct

<400> SEQUENCE: 229

His Lys Pro Arg Gly Gly Arg Lys Lys Ala Leu His
1               5                   10

<210> SEQ ID NO 230
<211> LENGTH: 18
<212> TYPE: PRT
<213> ORGANISM: artificial sequence
<220> FEATURE:
<223> OTHER INFORMATION: Synthetic construct

<400> SEQUENCE: 230

Lys Pro Arg Pro Pro His Gly Lys Lys His Arg Pro Lys His Arg Pro
1               5                   10                  15

Lys Lys

<210> SEQ ID NO 231
<211> LENGTH: 18
<212> TYPE: PRT
<213> ORGANISM: artificial sequence
<220> FEATURE:
<223> OTHER INFORMATION: Synthetic construct

<400> SEQUENCE: 231

Arg Gly Arg Pro Lys Lys Gly His Gly Lys Arg Pro Gly His Arg Ala
1               5                   10                  15

Arg Lys

<210> SEQ ID NO 232
<211> LENGTH: 12
<212> TYPE: PRT
<213> ORGANISM: artificial sequence
<220> FEATURE:
<223> OTHER INFORMATION: Synthetic construct

<400> SEQUENCE: 232

Thr Pro Phe His Ser Pro Glu Asn Ala Pro Gly Ser
1               5                   10

<210> SEQ ID NO 233
<211> LENGTH: 13
<212> TYPE: PRT
```

```
<213> ORGANISM: artificial sequence
<220> FEATURE:
<223> OTHER INFORMATION: Synthetic construct

<400> SEQUENCE: 233

Thr Pro Phe His Ser Pro Glu Asn Ala Pro Gly Ser Lys
1               5                   10

<210> SEQ ID NO 234
<211> LENGTH: 16
<212> TYPE: PRT
<213> ORGANISM: artificial sequence
<220> FEATURE:
<223> OTHER INFORMATION: Synthetic construct

<400> SEQUENCE: 234

Thr Pro Phe His Ser Pro Glu Asn Ala Pro Gly Ser Gly Gly Gly Ser
1               5                   10                  15

<210> SEQ ID NO 235
<211> LENGTH: 17
<212> TYPE: PRT
<213> ORGANISM: artificial sequence
<220> FEATURE:
<223> OTHER INFORMATION: Synthetic construct

<400> SEQUENCE: 235

Thr Pro Phe His Ser Pro Glu Asn Ala Pro Gly Ser Gly Gly Gly Ser
1               5                   10                  15

Ser

<210> SEQ ID NO 236
<211> LENGTH: 15
<212> TYPE: PRT
<213> ORGANISM: artificial sequence
<220> FEATURE:
<223> OTHER INFORMATION: Synthetic construct

<400> SEQUENCE: 236

Thr Pro Phe His Ser Pro Glu Asn Ala Pro Gly Ser Gly Gly Gly
1               5                   10                  15

<210> SEQ ID NO 237
<211> LENGTH: 7
<212> TYPE: PRT
<213> ORGANISM: artificial sequence
<220> FEATURE:
<223> OTHER INFORMATION: Synthetic construct

<400> SEQUENCE: 237

Phe Thr Gln Ser Leu Pro Arg
1               5

<210> SEQ ID NO 238
<211> LENGTH: 12
<212> TYPE: PRT
<213> ORGANISM: artificial sequence
<220> FEATURE:
<223> OTHER INFORMATION: Synthetic construct

<400> SEQUENCE: 238

Lys Gln Ala Thr Phe Pro Pro Asn Pro Thr Ala Tyr
1               5                   10

<210> SEQ ID NO 239
<211> LENGTH: 12
```

```
<212> TYPE: PRT
<213> ORGANISM: artificial sequence
<220> FEATURE:
<223> OTHER INFORMATION: Synthetic construct

<400> SEQUENCE: 239

His Gly His Met Val Ser Thr Ser Gln Leu Ser Ile
 1               5                  10

<210> SEQ ID NO 240
<211> LENGTH: 7
<212> TYPE: PRT
<213> ORGANISM: artificial sequence
<220> FEATURE:
<223> OTHER INFORMATION: Synthetic construct

<400> SEQUENCE: 240

Leu Ser Pro Ser Arg Met Lys
 1               5

<210> SEQ ID NO 241
<211> LENGTH: 7
<212> TYPE: PRT
<213> ORGANISM: artificial sequence
<220> FEATURE:
<223> OTHER INFORMATION: Synthetic construct

<400> SEQUENCE: 241

Leu Pro Ile Pro Arg Met Lys
 1               5

<210> SEQ ID NO 242
<211> LENGTH: 7
<212> TYPE: PRT
<213> ORGANISM: artificial sequence
<220> FEATURE:
<223> OTHER INFORMATION: Synthetic construct

<400> SEQUENCE: 242

His Gln Arg Pro Tyr Leu Thr
 1               5

<210> SEQ ID NO 243
<211> LENGTH: 7
<212> TYPE: PRT
<213> ORGANISM: artificial sequence
<220> FEATURE:
<223> OTHER INFORMATION: Synthetic construct

<400> SEQUENCE: 243

Phe Pro Pro Leu Leu Arg Leu
 1               5

<210> SEQ ID NO 244
<211> LENGTH: 7
<212> TYPE: PRT
<213> ORGANISM: artificial sequence
<220> FEATURE:
<223> OTHER INFORMATION: Synthetic construct

<400> SEQUENCE: 244

Gln Ala Thr Phe Met Tyr Asn
 1               5

<210> SEQ ID NO 245
<211> LENGTH: 11
<212> TYPE: PRT
```

```
<213> ORGANISM: artificial sequence
<220> FEATURE:
<223> OTHER INFORMATION: Synthetic construct

<400> SEQUENCE: 245

Val Leu Thr Ser Gln Leu Pro Asn His Ser Met
1               5                   10

<210> SEQ ID NO 246
<211> LENGTH: 7
<212> TYPE: PRT
<213> ORGANISM: artificial sequence
<220> FEATURE:
<223> OTHER INFORMATION: Synthetic construct

<400> SEQUENCE: 246

His Ser Thr Ala Tyr Leu Thr
1               5

<210> SEQ ID NO 247
<211> LENGTH: 12
<212> TYPE: PRT
<213> ORGANISM: artificial sequence
<220> FEATURE:
<223> OTHER INFORMATION: Synthetic construct

<400> SEQUENCE: 247

Ala Pro Gln Gln Arg Pro Met Lys Thr Phe Asn Thr
1               5                   10

<210> SEQ ID NO 248
<211> LENGTH: 12
<212> TYPE: PRT
<213> ORGANISM: artificial sequence
<220> FEATURE:
<223> OTHER INFORMATION: Synthetic construct

<400> SEQUENCE: 248

Ala Pro Gln Gln Arg Pro Met Lys Thr Val Gln Tyr
1               5                   10

<210> SEQ ID NO 249
<211> LENGTH: 7
<212> TYPE: PRT
<213> ORGANISM: artificial sequence
<220> FEATURE:
<223> OTHER INFORMATION: Synthetic construct

<400> SEQUENCE: 249

Pro Pro Trp Leu Asp Leu Leu
1               5

<210> SEQ ID NO 250
<211> LENGTH: 7
<212> TYPE: PRT
<213> ORGANISM: artificial sequence
<220> FEATURE:
<223> OTHER INFORMATION: Synthetic construct

<400> SEQUENCE: 250

Pro Pro Trp Thr Phe Pro Leu
1               5

<210> SEQ ID NO 251
<211> LENGTH: 7
<212> TYPE: PRT
<213> ORGANISM: artificial sequence
```

```
<220> FEATURE:
<223> OTHER INFORMATION: Synthetic construct

<400> SEQUENCE: 251

Ser Val Thr His Leu Thr Ser
1               5

<210> SEQ ID NO 252
<211> LENGTH: 7
<212> TYPE: PRT
<213> ORGANISM: artificial sequence
<220> FEATURE:
<223> OTHER INFORMATION: Synthetic construct

<400> SEQUENCE: 252

Val Ile Thr Arg Leu Thr Ser
1               5

<210> SEQ ID NO 253
<211> LENGTH: 12
<212> TYPE: PRT
<213> ORGANISM: artificial sequence
<220> FEATURE:
<223> OTHER INFORMATION: Synthetic construct

<400> SEQUENCE: 253

Asp Leu Lys Pro Pro Leu Leu Ala Leu Ser Lys Val
1               5                   10

<210> SEQ ID NO 254
<211> LENGTH: 12
<212> TYPE: PRT
<213> ORGANISM: artificial sequence
<220> FEATURE:
<223> OTHER INFORMATION: Synthetic construct

<400> SEQUENCE: 254

Ser His Pro Ser Gly Ala Leu Gln Glu Gly Thr Phe
1               5                   10

<210> SEQ ID NO 255
<211> LENGTH: 12
<212> TYPE: PRT
<213> ORGANISM: artificial sequence
<220> FEATURE:
<223> OTHER INFORMATION: Synthetic construct

<400> SEQUENCE: 255

Phe Pro Leu Thr Ser Lys Pro Ser Gly Ala Cys Thr
1               5                   10

<210> SEQ ID NO 256
<211> LENGTH: 12
<212> TYPE: PRT
<213> ORGANISM: artificial sequence
<220> FEATURE:
<223> OTHER INFORMATION: Synthetic construct

<400> SEQUENCE: 256

Asp Leu Lys Pro Pro Leu Leu Ala Leu Ser Lys Val
1               5                   10

<210> SEQ ID NO 257
<211> LENGTH: 7
<212> TYPE: PRT
<213> ORGANISM: artificial sequence
<220> FEATURE:
```

```
<223> OTHER INFORMATION: Synthetic construct

<400> SEQUENCE: 257

Pro Leu Leu Ala Leu His Ser
1               5

<210> SEQ ID NO 258
<211> LENGTH: 7
<212> TYPE: PRT
<213> ORGANISM: artificial sequence
<220> FEATURE:
<223> OTHER INFORMATION: Synthetic construct

<400> SEQUENCE: 258

Val Pro Ile Ser Thr Gln Ile
1               5

<210> SEQ ID NO 259
<211> LENGTH: 12
<212> TYPE: PRT
<213> ORGANISM: artificial sequence
<220> FEATURE:
<223> OTHER INFORMATION: Synthetic construct

<400> SEQUENCE: 259

Tyr Ala Lys Gln His Tyr Pro Ile Ser Thr Phe Lys
1               5                   10

<210> SEQ ID NO 260
<211> LENGTH: 7
<212> TYPE: PRT
<213> ORGANISM: artificial sequence
<220> FEATURE:
<223> OTHER INFORMATION: Synthetic construct

<400> SEQUENCE: 260

His Ser Thr Ala Tyr Leu Thr
1               5

<210> SEQ ID NO 261
<211> LENGTH: 12
<212> TYPE: PRT
<213> ORGANISM: artificial sequence
<220> FEATURE:
<223> OTHER INFORMATION: Synthetic construct

<400> SEQUENCE: 261

Ser Thr Ala Tyr Leu Val Ala Met Ser Ala Ala Pro
1               5                   10

<210> SEQ ID NO 262
<211> LENGTH: 12
<212> TYPE: PRT
<213> ORGANISM: artificial sequence
<220> FEATURE:
<223> OTHER INFORMATION: Synthetic construct

<400> SEQUENCE: 262

Ser Val Ser Val Gly Met Lys Pro Ser Pro Arg Pro
1               5                   10

<210> SEQ ID NO 263
<211> LENGTH: 12
<212> TYPE: PRT
<213> ORGANISM: artificial sequence
<220> FEATURE:
<223> OTHER INFORMATION: Synthetic construct
```

```
<400> SEQUENCE: 263

Thr Met Gly Phe Thr Ala Pro Arg Phe Pro His Tyr
1               5                   10

<210> SEQ ID NO 264
<211> LENGTH: 12
<212> TYPE: PRT
<213> ORGANISM: artificial sequence
<220> FEATURE:
<223> OTHER INFORMATION: Synthetic construct

<400> SEQUENCE: 264

Asn Leu Gln His Ser Val Gly Thr Ser Pro Val Trp
1               5                   10

<210> SEQ ID NO 265
<211> LENGTH: 15
<212> TYPE: PRT
<213> ORGANISM: artificial sequence
<220> FEATURE:
<223> OTHER INFORMATION: Synthetic construct

<400> SEQUENCE: 265

Gln Leu Ser Tyr His Ala Tyr Pro Gln Ala Asn His His Ala Pro
1               5                   10                  15

<210> SEQ ID NO 266
<211> LENGTH: 12
<212> TYPE: PRT
<213> ORGANISM: artificial sequence
<220> FEATURE:
<223> OTHER INFORMATION: Synthetic construct

<400> SEQUENCE: 266

Asn Gln Ala Ala Ser Ile Thr Lys Arg Val Pro Tyr
1               5                   10

<210> SEQ ID NO 267
<211> LENGTH: 14
<212> TYPE: PRT
<213> ORGANISM: artificial sequence
<220> FEATURE:
<223> OTHER INFORMATION: Synthetic construct

<400> SEQUENCE: 267

Ser Gly Cys His Leu Val Tyr Asp Asn Gly Phe Cys Asp His
1               5                   10

<210> SEQ ID NO 268
<211> LENGTH: 14
<212> TYPE: PRT
<213> ORGANISM: artificial sequence
<220> FEATURE:
<223> OTHER INFORMATION: Synthetic construct

<400> SEQUENCE: 268

Ala Ser Cys Pro Ser Ala Ser His Ala Asp Pro Cys Ala His
1               5                   10

<210> SEQ ID NO 269
<211> LENGTH: 14
<212> TYPE: PRT
<213> ORGANISM: artificial sequence
<220> FEATURE:
<223> OTHER INFORMATION: Synthetic construct
```

```
<400> SEQUENCE: 269

Asn Leu Cys Asp Ser Ala Arg Asp Ser Pro Arg Cys Lys Val
1               5                   10

<210> SEQ ID NO 270
<211> LENGTH: 12
<212> TYPE: PRT
<213> ORGANISM: artificial sequence
<220> FEATURE:
<223> OTHER INFORMATION: Synthetic construct

<400> SEQUENCE: 270

Asn His Ser Asn Trp Lys Thr Ala Ala Asp Phe Leu
1               5                   10

<210> SEQ ID NO 271
<211> LENGTH: 12
<212> TYPE: PRT
<213> ORGANISM: artificial sequence
<220> FEATURE:
<223> OTHER INFORMATION: Synthetic construct

<400> SEQUENCE: 271

Gly Ser Ser Thr Val Gly Arg Pro Leu Ser Tyr Glu
1               5                   10

<210> SEQ ID NO 272
<211> LENGTH: 12
<212> TYPE: PRT
<213> ORGANISM: artificial sequence
<220> FEATURE:
<223> OTHER INFORMATION: Synthetic construct

<400> SEQUENCE: 272

Ser Asp Thr Ile Ser Arg Leu His Val Ser Met Thr
1               5                   10

<210> SEQ ID NO 273
<211> LENGTH: 12
<212> TYPE: PRT
<213> ORGANISM: artificial sequence
<220> FEATURE:
<223> OTHER INFORMATION: Synthetic construct

<400> SEQUENCE: 273

Ser Pro Leu Thr Val Pro Tyr Glu Arg Lys Leu Leu
1               5                   10

<210> SEQ ID NO 274
<211> LENGTH: 12
<212> TYPE: PRT
<213> ORGANISM: artificial sequence
<220> FEATURE:
<223> OTHER INFORMATION: Synthetic construct

<400> SEQUENCE: 274

Ser Pro Tyr Pro Ser Trp Ser Thr Pro Ala Gly Arg
1               5                   10

<210> SEQ ID NO 275
<211> LENGTH: 12
<212> TYPE: PRT
<213> ORGANISM: artificial sequence
<220> FEATURE:
<223> OTHER INFORMATION: Synthetic construct

<400> SEQUENCE: 275
```

```
Val Gln Pro Ile Thr Asn Thr Arg Tyr Glu Gly Gly
1               5                   10
```

<210> SEQ ID NO 276
<211> LENGTH: 12
<212> TYPE: PRT
<213> ORGANISM: artificial sequence
<220> FEATURE:
<223> OTHER INFORMATION: Synthetic construct

<400> SEQUENCE: 276

```
Trp Pro Met His Pro Glu Lys Gly Ser Arg Trp Ser
1               5                   10
```

<210> SEQ ID NO 277
<211> LENGTH: 14
<212> TYPE: PRT
<213> ORGANISM: artificial sequence
<220> FEATURE:
<223> OTHER INFORMATION: Synthetic construct

<400> SEQUENCE: 277

```
Asp Ala Cys Ser Gly Asn Gly His Pro Asn Asn Cys Asp Arg
1               5                   10
```

<210> SEQ ID NO 278
<211> LENGTH: 14
<212> TYPE: PRT
<213> ORGANISM: artificial sequence
<220> FEATURE:
<223> OTHER INFORMATION: Synthetic construct

<400> SEQUENCE: 278

```
Asp His Cys Leu Gly Arg Gln Leu Gln Pro Val Cys Tyr Pro
1               5                   10
```

<210> SEQ ID NO 279
<211> LENGTH: 14
<212> TYPE: PRT
<213> ORGANISM: artificial sequence
<220> FEATURE:
<223> OTHER INFORMATION: Synthetic construct

<400> SEQUENCE: 279

```
Asp Trp Cys Asp Thr Ile Ile Pro Gly Arg Thr Cys His Gly
1               5                   10
```

<210> SEQ ID NO 280
<211> LENGTH: 12
<212> TYPE: PRT
<213> ORGANISM: artificial sequence
<220> FEATURE:
<223> OTHER INFORMATION: Synthetic construct

<400> SEQUENCE: 280

```
Ala Leu Pro Arg Ile Ala Asn Thr Trp Ser Pro Ser
1               5                   10
```

<210> SEQ ID NO 281
<211> LENGTH: 12
<212> TYPE: PRT
<213> ORGANISM: artificial sequence
<220> FEATURE:
<223> OTHER INFORMATION: Synthetic construct

<400> SEQUENCE: 281

Tyr Pro Ser Phe Ser Pro Thr Tyr Arg Pro Ala Phe
1               5                   10

<210> SEQ ID NO 282
<211> LENGTH: 20
<212> TYPE: PRT
<213> ORGANISM: artificial sequence
<220> FEATURE:
<223> OTHER INFORMATION: Synthetic construct

<400> SEQUENCE: 282

Ala His Pro Glu Ser Leu Gly Ile Lys Tyr Ala Leu Asp Gly Asn Ser
1               5                   10                  15

Asp Pro His Ala
            20

<210> SEQ ID NO 283
<211> LENGTH: 20
<212> TYPE: PRT
<213> ORGANISM: artificial sequence
<220> FEATURE:
<223> OTHER INFORMATION: Synthetic construct

<400> SEQUENCE: 283

Ala Ser Val Ser Asn Tyr Pro Pro Ile His His Leu Ala Thr Ser Asn
1               5                   10                  15

Thr Thr Val Asn
            20

<210> SEQ ID NO 284
<211> LENGTH: 14
<212> TYPE: PRT
<213> ORGANISM: artificial sequence
<220> FEATURE:
<223> OTHER INFORMATION: Synthetic construct

<400> SEQUENCE: 284

Asp Glu Cys Met Glu Pro Leu Asn Ala Ala His Cys Trp Arg
1               5                   10

<210> SEQ ID NO 285
<211> LENGTH: 14
<212> TYPE: PRT
<213> ORGANISM: artificial sequence
<220> FEATURE:
<223> OTHER INFORMATION: Synthetic construct

<400> SEQUENCE: 285

Asp Glu Cys Met His Gly Ser Asp Val Glu Phe Cys Thr Ser
1               5                   10

<210> SEQ ID NO 286
<211> LENGTH: 14
<212> TYPE: PRT
<213> ORGANISM: artificial sequence
<220> FEATURE:
<223> OTHER INFORMATION: Synthetic construct

<400> SEQUENCE: 286

Asp Leu Cys Ser Met Gln Met Met Asn Thr Gly Cys His Tyr
1               5                   10

<210> SEQ ID NO 287
<211> LENGTH: 14
<212> TYPE: PRT
<213> ORGANISM: artificial sequence -continued

```
<220> FEATURE:
<223> OTHER INFORMATION: Synthetic construct

<400> SEQUENCE: 287

Asp Leu Cys Ser Ser Pro Ser Thr Trp Gly Ser Cys Ile Arg
1               5                   10

<210> SEQ ID NO 288
<211> LENGTH: 20
<212> TYPE: PRT
<213> ORGANISM: artificial sequence
<220> FEATURE:
<223> OTHER INFORMATION: Synthetic construct

<400> SEQUENCE: 288

Asp Pro Asn Glu Ser Asn Tyr Glu Asn Ala Thr Thr Val Ser Gln Pro
1               5                   10                  15

Thr Arg His Leu
            20

<210> SEQ ID NO 289
<211> LENGTH: 20
<212> TYPE: PRT
<213> ORGANISM: artificial sequence
<220> FEATURE:
<223> OTHER INFORMATION: Synthetic construct

<400> SEQUENCE: 289

Glu Pro Thr His Pro Thr Met Arg Ala Gln Met His Gln Ser Leu Arg
1               5                   10                  15

Ser Ser Ser Pro
            20

<210> SEQ ID NO 290
<211> LENGTH: 20
<212> TYPE: PRT
<213> ORGANISM: artificial sequence
<220> FEATURE:
<223> OTHER INFORMATION: Synthetic construct

<400> SEQUENCE: 290

Gly Asn Thr Asp Thr Thr Pro Pro Asn Ala Val Met Glu Pro Thr Val
1               5                   10                  15

Gln His Lys Trp
            20

<210> SEQ ID NO 291
<211> LENGTH: 15
<212> TYPE: PRT
<213> ORGANISM: artificial sequence
<220> FEATURE:
<223> OTHER INFORMATION: Synthetic construct

<400> SEQUENCE: 291

Asn Gly Pro Asp Met Val Gln Ser Val Gly Lys His Lys Asn Ser
1               5                   10                  15

<210> SEQ ID NO 292
<211> LENGTH: 15
<212> TYPE: PRT
<213> ORGANISM: artificial sequence
<220> FEATURE:
<223> OTHER INFORMATION: Synthetic construct

<400> SEQUENCE: 292
```

```
Asn Gly Pro Glu Val Arg Gln Ile Pro Ala Asn Phe Glu Lys Leu
1               5                   10                  15

<210> SEQ ID NO 293
<211> LENGTH: 20
<212> TYPE: PRT
<213> ORGANISM: artificial sequence
<220> FEATURE:
<223> OTHER INFORMATION: Synthetic construct

<400> SEQUENCE: 293

Asn Asn Thr Ser Ala Asp Asn Pro Pro Glu Thr Asp Ser Lys His His
1               5                   10                  15

Leu Ser Met Ser
            20

<210> SEQ ID NO 294
<211> LENGTH: 20
<212> TYPE: PRT
<213> ORGANISM: artificial sequence
<220> FEATURE:
<223> OTHER INFORMATION: Synthetic construct

<400> SEQUENCE: 294

Asn Asn Thr Trp Pro Glu Gly Ala Gly His Thr Met Pro Ser Thr Asn
1               5                   10                  15

Ile Arg Gln Ala
            20

<210> SEQ ID NO 295
<211> LENGTH: 20
<212> TYPE: PRT
<213> ORGANISM: artificial sequence
<220> FEATURE:
<223> OTHER INFORMATION: Synthetic construct

<400> SEQUENCE: 295

Asn Pro Thr Ala Thr Pro His Met Lys Asp Pro Met His Ser Asn Ala
1               5                   10                  15

His Ser Ser Ala
            20

<210> SEQ ID NO 296
<211> LENGTH: 20
<212> TYPE: PRT
<213> ORGANISM: artificial sequence
<220> FEATURE:
<223> OTHER INFORMATION: Synthetic construct

<400> SEQUENCE: 296

Asn Pro Thr Asp His Ile Pro Ala Asn Ser Thr Asn Ser Arg Val Ser
1               5                   10                  15

Lys Gly Asn Thr
            20

<210> SEQ ID NO 297
<211> LENGTH: 15
<212> TYPE: PRT
<213> ORGANISM: artificial sequence
<220> FEATURE:
<223> OTHER INFORMATION: Synthetic construct

<400> SEQUENCE: 297

Asn Pro Thr Asp Ser Thr His Met Met His Ala Arg Asn His Glu
1               5                   10                  15
```

<210> SEQ ID NO 298
<211> LENGTH: 14
<212> TYPE: PRT
<213> ORGANISM: artificial sequence
<220> FEATURE:
<223> OTHER INFORMATION: Synthetic construct

<400> SEQUENCE: 298

Gln His Cys Ile Thr Glu Arg Leu His Pro Pro Cys Thr Lys
1               5                   10

<210> SEQ ID NO 299
<211> LENGTH: 14
<212> TYPE: PRT
<213> ORGANISM: artificial sequence
<220> FEATURE:
<223> OTHER INFORMATION: Synthetic construct

<400> SEQUENCE: 299

Thr Pro Cys Ala Pro Ala Ser Phe Asn Pro His Cys Ser Arg
1               5                   10

<210> SEQ ID NO 300
<211> LENGTH: 14
<212> TYPE: PRT
<213> ORGANISM: artificial sequence
<220> FEATURE:
<223> OTHER INFORMATION: Synthetic construct

<400> SEQUENCE: 300

Thr Pro Cys Ala Thr Tyr Pro His Phe Ser Gly Cys Arg Ala
1               5                   10

<210> SEQ ID NO 301
<211> LENGTH: 20
<212> TYPE: PRT
<213> ORGANISM: artificial sequence
<220> FEATURE:
<223> OTHER INFORMATION: Synthetic construct

<400> SEQUENCE: 301

Trp Cys Thr Asp Phe Cys Thr Arg Ser Thr Pro Thr Ser Thr Ser Arg
1               5                   10                  15

Ser Thr Thr Ser
            20

<210> SEQ ID NO 302
<211> LENGTH: 20
<212> TYPE: PRT
<213> ORGANISM: artificial sequence
<220> FEATURE:
<223> OTHER INFORMATION: Synthetic construct

<400> SEQUENCE: 302

Ala Pro Pro Leu Lys Thr Tyr Met Gln Glu Arg Glu Leu Thr Met Ser
1               5                   10                  15

Gln Asn Lys Asp
            20

<210> SEQ ID NO 303
<211> LENGTH: 20
<212> TYPE: PRT
<213> ORGANISM: artificial sequence
<220> FEATURE:
<223> OTHER INFORMATION: Synthetic construct

```
<400> SEQUENCE: 303

Glu Pro Pro Thr Arg Thr Arg Val Asn Asn His Thr Val Thr Val Gln
1               5                   10                  15

Ala Gln Gln His
            20

<210> SEQ ID NO 304
<211> LENGTH: 14
<212> TYPE: PRT
<213> ORGANISM: artificial sequence
<220> FEATURE:
<223> OTHER INFORMATION: Synthetic construct

<400> SEQUENCE: 304

Gly Tyr Cys Leu Arg Gly Asp Glu Pro Ala Val Cys Ser Gly
1               5                   10

<210> SEQ ID NO 305
<211> LENGTH: 20
<212> TYPE: PRT
<213> ORGANISM: artificial sequence
<220> FEATURE:
<223> OTHER INFORMATION: Synthetic construct

<400> SEQUENCE: 305

Leu Ser Ser Lys Asp Phe Gly Val Thr Asn Thr Asp Gln Arg Thr Tyr
1               5                   10                  15

Asp Tyr Thr Thr
            20

<210> SEQ ID NO 306
<211> LENGTH: 14
<212> TYPE: PRT
<213> ORGANISM: artificial sequence
<220> FEATURE:
<223> OTHER INFORMATION: Synthetic construct

<400> SEQUENCE: 306

Asn Phe Cys Glu Thr Gln Leu Asp Leu Ser Val Cys Thr Val
1               5                   10

<210> SEQ ID NO 307
<211> LENGTH: 14
<212> TYPE: PRT
<213> ORGANISM: artificial sequence
<220> FEATURE:
<223> OTHER INFORMATION: Synthetic construct

<400> SEQUENCE: 307

Asn Thr Cys Gln Pro Thr Lys Asn Ala Thr Pro Cys Ser Ala
1               5                   10

<210> SEQ ID NO 308
<211> LENGTH: 20
<212> TYPE: PRT
<213> ORGANISM: artificial sequence
<220> FEATURE:
<223> OTHER INFORMATION: Synthetic construct

<400> SEQUENCE: 308

Pro Ser Glu Pro Glu Arg Arg Asp Arg Asn Ile Ala Ala Asn Ala Gly
1               5                   10                  15

Arg Phe Asn Thr
            20
```

```
<210> SEQ ID NO 309
<211> LENGTH: 18
<212> TYPE: PRT
<213> ORGANISM: artificial sequence
<220> FEATURE:
<223> OTHER INFORMATION: Synthetic construct

<400> SEQUENCE: 309

Thr His Asn Met Ser His Phe Pro Pro Ser Gly His Pro Lys Arg Thr
1               5                   10                  15

Ala Thr

<210> SEQ ID NO 310
<211> LENGTH: 14
<212> TYPE: PRT
<213> ORGANISM: artificial sequence
<220> FEATURE:
<223> OTHER INFORMATION: Synthetic construct

<400> SEQUENCE: 310

Thr Thr Cys Pro Thr Met Gly Thr Tyr His Val Cys Trp Leu
1               5                   10

<210> SEQ ID NO 311
<211> LENGTH: 20
<212> TYPE: PRT
<213> ORGANISM: artificial sequence
<220> FEATURE:
<223> OTHER INFORMATION: Synthetic construct

<400> SEQUENCE: 311

Tyr Cys Ala Asp His Thr Pro Asp Pro Ala Asn Pro Asn Lys Ile Cys
1               5                   10                  15

Gly Tyr Ser His
            20

<210> SEQ ID NO 312
<211> LENGTH: 20
<212> TYPE: PRT
<213> ORGANISM: artificial sequence
<220> FEATURE:
<223> OTHER INFORMATION: Synthetic construct

<400> SEQUENCE: 312

Ala Ala Asn Pro His Thr Glu Trp Asp Arg Asp Ala Phe Gln Leu Ala
1               5                   10                  15

Met Pro Pro Lys
            20

<210> SEQ ID NO 313
<211> LENGTH: 20
<212> TYPE: PRT
<213> ORGANISM: artificial sequence
<220> FEATURE:
<223> OTHER INFORMATION: Synthetic construct

<400> SEQUENCE: 313

Asp Leu His Pro Met Asp Pro Ser Asn Lys Arg Pro Asp Asn Pro Ser
1               5                   10                  15

Asp Leu His Thr
            20

<210> SEQ ID NO 314
```

```
<211> LENGTH: 14
<212> TYPE: PRT
<213> ORGANISM: artificial sequence
<220> FEATURE:
<223> OTHER INFORMATION: Synthetic construct

<400> SEQUENCE: 314

Glu Ser Cys Val Ser Asn Ala Leu Met Asn Gln Cys Ile Tyr
1               5                   10

<210> SEQ ID NO 315
<211> LENGTH: 20
<212> TYPE: PRT
<213> ORGANISM: artificial sequence
<220> FEATURE:
<223> OTHER INFORMATION: Synthetic construct

<400> SEQUENCE: 315

His Asn Lys Ala Asp Ser Trp Asp Pro Asp Leu Pro Pro His Ala Gly
1               5                   10                  15

Met Ser Leu Gly
            20

<210> SEQ ID NO 316
<211> LENGTH: 20
<212> TYPE: PRT
<213> ORGANISM: artificial sequence
<220> FEATURE:
<223> OTHER INFORMATION: Synthetic construct

<400> SEQUENCE: 316

Leu Asn Asp Gln Arg Lys Pro Gly Pro Pro Thr Met Pro Thr His Ser
1               5                   10                  15

Pro Ala Val Gly
            20

<210> SEQ ID NO 317
<211> LENGTH: 14
<212> TYPE: PRT
<213> ORGANISM: artificial sequence
<220> FEATURE:
<223> OTHER INFORMATION: Synthetic construct

<400> SEQUENCE: 317

Asn Thr Cys Ala Thr Ser Pro Asn Ser Tyr Thr Cys Ser Asn
1               5                   10

<210> SEQ ID NO 318
<211> LENGTH: 14
<212> TYPE: PRT
<213> ORGANISM: artificial sequence
<220> FEATURE:
<223> OTHER INFORMATION: Synthetic construct

<400> SEQUENCE: 318

Ser Asp Cys Thr Ala Gly Leu Val Pro Pro Leu Cys Ala Thr
1               5                   10

<210> SEQ ID NO 319
<211> LENGTH: 20
<212> TYPE: PRT
<213> ORGANISM: artificial sequence
<220> FEATURE:
<223> OTHER INFORMATION: Synthetic construct

<400> SEQUENCE: 319
```

```
Thr Ile Glu Ser Ser Gln His Ser Arg Thr His Gln Gln Asn Tyr Gly
1               5                   10                  15

Ser Thr Lys Thr
            20

<210> SEQ ID NO 320
<211> LENGTH: 20
<212> TYPE: PRT
<213> ORGANISM: artificial sequence
<220> FEATURE:
<223> OTHER INFORMATION: Synthetic construct

<400> SEQUENCE: 320

Val Gly Thr Met Lys Gln His Pro Thr Thr Thr Gln Pro Pro Arg Val
1               5                   10                  15

Ser Ala Thr Asn
            20

<210> SEQ ID NO 321
<211> LENGTH: 20
<212> TYPE: PRT
<213> ORGANISM: artificial sequence
<220> FEATURE:
<223> OTHER INFORMATION: Synthetic construct

<400> SEQUENCE: 321

Tyr Ser Glu Thr Pro Asn Asp Gln Lys Pro Asn Pro His Tyr Lys Val
1               5                   10                  15

Ser Gly Thr Lys
            20

<210> SEQ ID NO 322
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 322

Asn Gly Asn Asn His Thr Asp Ile Pro Asn Arg Ser Ser Tyr Thr Gly
1               5                   10                  15

Gly Ser Phe Ala
            20

<210> SEQ ID NO 323
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 323

Thr Met Thr Asn His Val Tyr Asn Ser Tyr Thr Glu Lys His Ser Ser
1               5                   10                  15

Thr His Arg Ser
            20

<210> SEQ ID NO 324
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 324
```

```
Thr Thr Tyr His Tyr Lys Asn Ile Tyr Gln Glu Ser Tyr Gln Gln Arg
1               5                  10                  15

Asn Pro Ala Val
            20

<210> SEQ ID NO 325
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 325

Val Glu Pro Ala Thr Lys Asn Met Arg Glu Ala Arg Ser Ser Thr Gln
1               5                  10                  15

Met Arg Arg Ile
            20

<210> SEQ ID NO 326
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 326

Tyr Leu Leu Pro Lys Asp Gln Thr Thr Ala Pro Gln Val Thr Pro Ile
1               5                  10                  15

Val Gln His Lys
            20

<210> SEQ ID NO 327
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 327

Ala Ser Asn Leu Asp Ser Thr Phe Thr Ala Ile Asn Thr Pro Ala Cys
1               5                  10                  15

Cys Thr

<210> SEQ ID NO 328
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 328

Glu Phe Pro Tyr Tyr Asn Asp Asn Pro Pro Asn Pro Glu Arg His Thr
1               5                  10                  15

Leu Arg

<210> SEQ ID NO 329
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 329
```

```
Gly Met Pro Thr Arg Tyr Tyr His Asn Thr Pro Pro His Leu Thr Pro
1               5                   10                  15
Lys Phe

<210> SEQ ID NO 330
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 330

His Lys Asn Ala Ile Gln Pro Val Asn Asp Ala Thr Thr Leu Asp Thr
1               5                   10                  15
Thr Met

<210> SEQ ID NO 331
<211> LENGTH: 15
<212> TYPE: PRT
<213> ORGANISM: Artificial Sequence
<220> FEATURE:
<223> OTHER INFORMATION: Synthetic oral-surface binding peptide

<400> SEQUENCE: 331

Ala Val Val Pro Ala Asp Leu Asn Asp His Ala Asn His Leu Ser
1               5                   10                  15

<210> SEQ ID NO 332
<211> LENGTH: 15
<212> TYPE: PRT
<213> ORGANISM: Artificial Sequence
<220> FEATURE:
<223> OTHER INFORMATION: Synthetic oral-surface binding peptide

<400> SEQUENCE: 332

Asp Leu Gly Thr Phe Pro Asn Arg Thr Leu Lys Met Ala Ala His
1               5                   10                  15

<210> SEQ ID NO 333
<211> LENGTH: 15
<212> TYPE: PRT
<213> ORGANISM: Artificial Sequence
<220> FEATURE:
<223> OTHER INFORMATION: Synthetic oral-surface binding peptide

<400> SEQUENCE: 333

Phe Asp Gly Ile Gly Leu Gly Thr Ala Thr Arg His Gln Asn Arg
1               5                   10                  15

<210> SEQ ID NO 334
<211> LENGTH: 15
<212> TYPE: PRT
<213> ORGANISM: Artificial Sequence
<220> FEATURE:
<223> OTHER INFORMATION: Synthetic oral-surface binding peptide

<400> SEQUENCE: 334

Gln Ala Ala Gln Val His Met Met Gln His Ser Arg Pro Thr Thr
1               5                   10                  15

<210> SEQ ID NO 335
<211> LENGTH: 18
<212> TYPE: PRT
<213> ORGANISM: Artificial Sequence
<220> FEATURE:
<223> OTHER INFORMATION: Synthetic oral-surface binding peptide
```

-continued

```
<400> SEQUENCE: 335

Ser Glu Ala Arg Ala Arg Thr Phe Asn Asp His Thr Thr Pro Met Pro
1               5                   10                  15

Ile Ile

<210> SEQ ID NO 336
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 336

Glu Leu Asp His Asp Ser Arg His Tyr Met Asn Gly Leu Gln Arg Lys
1               5                   10                  15

Val Thr

<210> SEQ ID NO 337
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 337

Gly Pro Gln His Val Leu Met Gln Asp Thr His Gln Gly Tyr Ala Phe
1               5                   10                  15

Asp Asn

<210> SEQ ID NO 338
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 338

Thr Thr Gly Ser Ser Ser Gln Ala Asp Thr Ser Ala Ser Met Ser Ile
1               5                   10                  15

Val Pro Ala His
            20

<210> SEQ ID NO 339
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 339

Lys Ala Pro Ile Ala Asn Met Leu Gln Pro His Ser Tyr Gln Tyr Ser
1               5                   10                  15

Val Ala

<210> SEQ ID NO 340
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 340
```

```
Thr Tyr Gln Gly Val Pro Ser Trp Pro Ala Val Ile Asp Asp Ala Ile
1               5                   10                  15

Arg Arg

<210> SEQ ID NO 341
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 341

Val Asn Pro Asn Trp Val Glu Thr Gln Ala Leu His Gln Pro Pro Gly
1               5                   10                  15

Asn Thr

<210> SEQ ID NO 342
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 342

Asp His Asn Asn Arg Gln His Ala Val Glu Val Arg Glu Asn Lys Thr
1               5                   10                  15

His Thr Ala Arg
            20

<210> SEQ ID NO 343
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 343

Ile Tyr Pro Asn Glu Ser Met Ser Thr Ser Asn Val Arg Gly Pro Tyr
1               5                   10                  15

His Pro

<210> SEQ ID NO 344
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 344

His Asp Pro Asn His Leu Thr His Gln Ala Arg Thr Ile Tyr Arg Asn
1               5                   10                  15

Ala Asn His Thr
            20

<210> SEQ ID NO 345
<211> LENGTH: 15
<212> TYPE: PRT
<213> ORGANISM: Artificial Sequence
<220> FEATURE:
<223> OTHER INFORMATION: Synthetic oral-surface binding peptide

<400> SEQUENCE: 345

Ser Asn Ala Thr Met Tyr Asn Ile Gln Ser His Ser His His Gln
1               5                   10                  15
```

```
<210> SEQ ID NO 346
<211> LENGTH: 15
<212> TYPE: PRT
<213> ORGANISM: Artificial Sequence
<220> FEATURE:
<223> OTHER INFORMATION: Synthetic oral-surface binding peptide

<400> SEQUENCE: 346

Ala Asn Glu Leu Ser Thr Tyr Ala Gln Thr Asn Pro Gly Ser Gly
1               5                   10                  15

<210> SEQ ID NO 347
<211> LENGTH: 15
<212> TYPE: PRT
<213> ORGANISM: Artificial Sequence
<220> FEATURE:
<223> OTHER INFORMATION: Synthetic oral-surface binding peptide

<400> SEQUENCE: 347

Asp Thr Ile His Pro Asn Lys Met Lys Ser Pro Ser Ser Pro Leu
1               5                   10                  15

<210> SEQ ID NO 348
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 348

Ala Pro Pro Thr Tyr Gln Thr Ala Ser Tyr Pro His Asn Leu Pro Ser
1               5                   10                  15

Lys Arg Lys Met
            20

<210> SEQ ID NO 349
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 349

Gln Val Pro Asp Tyr Leu Ser Pro Thr His Gln Lys Lys Ala Phe Leu
1               5                   10                  15

Glu Ile Pro Thr
            20

<210> SEQ ID NO 350
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 350

Thr Asn Asp Leu His Ala Asn Pro Phe Thr Gly Thr Tyr Ile Ala Pro
1               5                   10                  15

Asp Pro Thr Ser
            20

<210> SEQ ID NO 351
<211> LENGTH: 20
<212> TYPE: PRT
```

<213> ORGANISM: Artificial Sequence
<220> FEATURE:
<223> OTHER INFORMATION: Synthetic oral-surface binding peptide

<400> SEQUENCE: 351

His Lys Asn Glu Asn Ile Met Gln Tyr Asn Val Asn Asp Arg Trp His
1               5                   10                  15

Ile Thr Pro Ala
            20

<210> SEQ ID NO 352
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 352

Ile Asp Gly Pro His His Ser Pro Val His Arg Tyr His Thr Pro Ser
1               5                   10                  15

Ile Thr

<210> SEQ ID NO 353
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 353

Ala Ile Glu Tyr Gln His Ser Ala Thr Thr Pro Trp Thr Met Arg Thr
1               5                   10                  15

Arg Leu Pro Pro
            20

<210> SEQ ID NO 354
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 354

Glu Phe Tyr Pro Phe Ala Glu Val Pro Pro Glu Lys Ser Gly Ile Gly
1               5                   10                  15

Arg Gln Val Phe
            20

<210> SEQ ID NO 355
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 355

Gly Val His Gln Tyr Ser Arg Pro Thr Val Pro Ser Tyr Leu Trp Thr
1               5                   10                  15

Ser Gly Gln His
            20

<210> SEQ ID NO 356
<211> LENGTH: 20
<212> TYPE: PRT

```
<213> ORGANISM: Artificial Sequence
<220> FEATURE:
<223> OTHER INFORMATION: Synthetic oral-surface binding peptide

<400> SEQUENCE: 356

Gly Tyr Gln Pro His Tyr Val Asp His Thr Ile Gly Trp Gln Pro Met
1               5                   10                  15

Ile Arg Pro Asn
        20

<210> SEQ ID NO 357
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 357

Gln Phe Asn Gln Thr Ser His Ser Phe Met His Gly Thr Ser Gly Tyr
1               5                   10                  15

Val Pro Gly Lys
        20

<210> SEQ ID NO 358
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 358

Ser Phe Ser Trp His Arg Gly Asp Trp Glu Leu Gly His Gln Ser Lys
1               5                   10                  15

Thr Met Gly Met
        20

<210> SEQ ID NO 359
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 359

Ser Met Trp His Asp Ile Thr Lys Arg Tyr Arg Asn Pro Ser Glu Met
1               5                   10                  15

Val Ser Ala Tyr
        20

<210> SEQ ID NO 360
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 360

Thr His Gly Asn Lys His Gln Ser Trp Thr Tyr Pro Ser Glu Ile Asn
1               5                   10                  15

His Lys Asn Tyr
        20

<210> SEQ ID NO 361
<211> LENGTH: 20
```

<212> TYPE: PRT
<213> ORGANISM: Artificial Sequence
<220> FEATURE:
<223> OTHER INFORMATION: Synthetic oral-surface binding peptide

<400> SEQUENCE: 361

Trp His Glu Pro His Gln Phe Ser Gly Glu Asn Thr Asp Tyr Ser Ser
1               5                   10                  15

Ser Met Gly Thr
            20

<210> SEQ ID NO 362
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 362

Thr His Gly Asn Lys His Gln Ser Trp Thr Tyr Pro Ser Glu Ile Asn
1               5                   10                  15

His Lys Asn Tyr
            20

<210> SEQ ID NO 363
<211> LENGTH: 16
<212> TYPE: PRT
<213> ORGANISM: Artificial Sequence
<220> FEATURE:
<223> OTHER INFORMATION: Synthetic oral-surface binding peptide

<400> SEQUENCE: 363

Asp Gly Tyr Lys Leu Gln Thr Ser Leu Asp Trp Gln Met Trp Asn Pro
1               5                   10                  15

<210> SEQ ID NO 364
<211> LENGTH: 16
<212> TYPE: PRT
<213> ORGANISM: Artificial Sequence
<220> FEATURE:
<223> OTHER INFORMATION: Synthetic oral-surface binding peptide

<400> SEQUENCE: 364

Phe Pro Ser Lys Trp Tyr Asn His His Arg His Ile Thr Gly His Val
1               5                   10                  15

<210> SEQ ID NO 365
<211> LENGTH: 16
<212> TYPE: PRT
<213> ORGANISM: Artificial Sequence
<220> FEATURE:
<223> OTHER INFORMATION: Synthetic oral-surface binding peptide

<400> SEQUENCE: 365

Gly Gly Met Gly Ala Leu Glu Ser Tyr Arg Gln Trp Asn His Leu Ala
1               5                   10                  15

<210> SEQ ID NO 366
<211> LENGTH: 16
<212> TYPE: PRT
<213> ORGANISM: Artificial Sequence
<220> FEATURE:
<223> OTHER INFORMATION: Synthetic oral-surface binding peptide

<400> SEQUENCE: 366

Gly Ile Asn Lys Gly Gln Arg Pro Pro Trp Glu Ser Trp His Glu Asn

```
                1               5                  10                 15

<210> SEQ ID NO 367
<211> LENGTH: 16
<212> TYPE: PRT
<213> ORGANISM: Artificial Sequence
<220> FEATURE:
<223> OTHER INFORMATION: Synthetic oral-surface binding peptide

<400> SEQUENCE: 367

Gly Tyr Gly Gln Tyr Val Ser Gln Gln Thr Trp Ala His Ser Asn Lys
1               5                   10                  15

<210> SEQ ID NO 368
<211> LENGTH: 16
<212> TYPE: PRT
<213> ORGANISM: Artificial Sequence
<220> FEATURE:
<223> OTHER INFORMATION: Synthetic oral-surface binding peptide

<400> SEQUENCE: 368

His Asp His Leu Ser Trp Trp Gly Gln Phe Asp Arg Gln Asn Leu Leu
1               5                   10                  15

<210> SEQ ID NO 369
<211> LENGTH: 16
<212> TYPE: PRT
<213> ORGANISM: Artificial Sequence
<220> FEATURE:
<223> OTHER INFORMATION: Synthetic oral-surface binding peptide

<400> SEQUENCE: 369

Met Pro Gly His Gln Glu Ser Ile Lys Val Gln Asn Trp Asn Arg Val
1               5                   10                  15

<210> SEQ ID NO 370
<211> LENGTH: 16
<212> TYPE: PRT
<213> ORGANISM: Artificial Sequence
<220> FEATURE:
<223> OTHER INFORMATION: Synthetic oral-surface binding peptide

<400> SEQUENCE: 370

Asn Leu His Ser Pro Trp Pro Ser His Ala Ala His His Trp Ser Thr
1               5                   10                  15

<210> SEQ ID NO 371
<211> LENGTH: 16
<212> TYPE: PRT
<213> ORGANISM: Artificial Sequence
<220> FEATURE:
<223> OTHER INFORMATION: Synthetic oral-surface binding peptide

<400> SEQUENCE: 371

Asn Gln Gln Met Lys Leu Val Pro Gln His Trp His Arg Ala Gln Pro
1               5                   10                  15

<210> SEQ ID NO 372
<211> LENGTH: 16
<212> TYPE: PRT
<213> ORGANISM: Artificial Sequence
<220> FEATURE:
<223> OTHER INFORMATION: Synthetic oral-surface binding peptide

<400> SEQUENCE: 372

Ser Glu Lys Trp Phe Asn Pro Gly Pro Trp Pro Lys Leu Ala Thr Gln
1               5                   10                  15
```

```
<210> SEQ ID NO 373
<211> LENGTH: 25
<212> TYPE: PRT
<213> ORGANISM: Artificial Sequence
<220> FEATURE:
<223> OTHER INFORMATION: synthetic construct

<400> SEQUENCE: 373

Ser Ser Arg Pro Asn Gly Asn Asn His Thr Asp Ile Pro Asn Arg Ser
1               5                   10                  15

Ser Tyr Thr Gly Gly Ser Phe Ala Lys
            20                  25

<210> SEQ ID NO 374
<211> LENGTH: 25
<212> TYPE: PRT
<213> ORGANISM: Artificial Sequence
<220> FEATURE:
<223> OTHER INFORMATION: synthetic construct

<400> SEQUENCE: 374

Ser Ser Arg Pro Thr Met Thr Asn His Val Tyr Asn Ser Tyr Thr Glu
1               5                   10                  15

Lys His Ser Ser Thr His Arg Ser Lys
            20                  25

<210> SEQ ID NO 375
<211> LENGTH: 25
<212> TYPE: PRT
<213> ORGANISM: Artificial Sequence
<220> FEATURE:
<223> OTHER INFORMATION: synthetic construct

<400> SEQUENCE: 375

Ser Ser Arg Pro Thr Thr Tyr His Tyr Lys Asn Ile Tyr Gln Glu Ser
1               5                   10                  15

Tyr Gln Gln Arg Asn Pro Ala Val Lys
            20                  25

<210> SEQ ID NO 376
<211> LENGTH: 25
<212> TYPE: PRT
<213> ORGANISM: Artificial Sequence
<220> FEATURE:
<223> OTHER INFORMATION: synthetic construct

<400> SEQUENCE: 376

Ser Ser Arg Pro Val Glu Pro Ala Thr Lys Asn Met Arg Glu Ala Arg
1               5                   10                  15

Ser Ser Thr Gln Met Arg Arg Ile Lys
            20                  25

<210> SEQ ID NO 377
<211> LENGTH: 25
<212> TYPE: PRT
<213> ORGANISM: Artificial Sequence
<220> FEATURE:
<223> OTHER INFORMATION: synthetic construct

<400> SEQUENCE: 377

Ser Ser Arg Pro Tyr Leu Leu Pro Lys Asp Gln Thr Thr Ala Pro Gln
1               5                   10                  15

Val Thr Pro Ile Val Gln His Lys Lys
```

```
                        20                  25

<210> SEQ ID NO 378
<211> LENGTH: 23
<212> TYPE: PRT
<213> ORGANISM: Artificial Sequence
<220> FEATURE:
<223> OTHER INFORMATION: synthetic construct

<400> SEQUENCE: 378

Ser Ser Arg Pro Glu Phe Pro Tyr Tyr Asn Asp Asn Pro Pro Asn Pro
1               5                   10                  15

Glu Arg His Thr Leu Arg Lys
            20

<210> SEQ ID NO 379
<211> LENGTH: 20
<212> TYPE: PRT
<213> ORGANISM: Artificial Sequence
<220> FEATURE:
<223> OTHER INFORMATION: synthetic construct

<400> SEQUENCE: 379

Ser Ser Arg Pro Asp Leu Gly Thr Phe Pro Asn Arg Thr Leu Lys Met
1               5                   10                  15

Ala Ala His Lys
            20

<210> SEQ ID NO 380
<211> LENGTH: 20
<212> TYPE: PRT
<213> ORGANISM: Artificial Sequence
<220> FEATURE:
<223> OTHER INFORMATION: synthetic construct

<400> SEQUENCE: 380

Ser Ser Arg Pro Phe Asp Gly Ile Gly Leu Gly Thr Ala Thr Arg His
1               5                   10                  15

Gln Asn Arg Lys
            20

<210> SEQ ID NO 381
<211> LENGTH: 20
<212> TYPE: PRT
<213> ORGANISM: Artificial Sequence
<220> FEATURE:
<223> OTHER INFORMATION: synthetic construct

<400> SEQUENCE: 381

Ser Ser Arg Pro Gln Ala Ala Gln Val His Met Met Gln His Ser Arg
1               5                   10                  15

Pro Thr Thr Lys
            20

<210> SEQ ID NO 382
<211> LENGTH: 23
<212> TYPE: PRT
<213> ORGANISM: Artificial Sequence
<220> FEATURE:
<223> OTHER INFORMATION: synthetic construct

<400> SEQUENCE: 382

Ser Ser Arg Pro Ser Glu Ala Arg Ala Arg Thr Phe Asn Asp His Thr
1               5                   10                  15
```

Thr Pro Met Pro Ile Ile Lys
            20

<210> SEQ ID NO 383
<211> LENGTH: 23
<212> TYPE: PRT
<213> ORGANISM: Artificial Sequence
<220> FEATURE:
<223> OTHER INFORMATION: synthetic construct

<400> SEQUENCE: 383

Ser Ser Arg Pro Glu Leu Asp His Asp Ser Arg His Tyr Met Asn Gly
1               5                   10                  15

Leu Gln Arg Lys Val Thr Lys
            20

<210> SEQ ID NO 384
<211> LENGTH: 23
<212> TYPE: PRT
<213> ORGANISM: Artificial Sequence
<220> FEATURE:
<223> OTHER INFORMATION: synthetic construct

<400> SEQUENCE: 384

Ser Ser Arg Pro Gly Pro Gln His Val Leu Met Gln Asp Thr His Gln
1               5                   10                  15

Gly Tyr Ala Phe Asp Asn Lys
            20

<210> SEQ ID NO 385
<211> LENGTH: 25
<212> TYPE: PRT
<213> ORGANISM: Artificial Sequence
<220> FEATURE:
<223> OTHER INFORMATION: synthetic construct

<400> SEQUENCE: 385

Ser Ser Arg Pro Thr Thr Gly Ser Ser Ser Gln Ala Asp Thr Ser Ala
1               5                   10                  15

Ser Met Ser Ile Val Pro Ala His Lys
            20                  25

<210> SEQ ID NO 386
<211> LENGTH: 23
<212> TYPE: PRT
<213> ORGANISM: Artificial Sequence
<220> FEATURE:
<223> OTHER INFORMATION: synthetic construct

<400> SEQUENCE: 386

Ser Ser Arg Pro Thr Tyr Gln Gly Val Pro Ser Trp Pro Ala Val Ile
1               5                   10                  15

Asp Asp Ala Ile Arg Arg Lys
            20

<210> SEQ ID NO 387
<211> LENGTH: 23
<212> TYPE: PRT
<213> ORGANISM: Artificial Sequence
<220> FEATURE:
<223> OTHER INFORMATION: synthetic construct

<400> SEQUENCE: 387

Ser Ser Arg Pro Val Asn Pro Asn Trp Val Glu Thr Gln Ala Leu His
1               5                   10                  15

```
Gln Pro Pro Gly Asn Thr Lys
            20

<210> SEQ ID NO 388
<211> LENGTH: 23
<212> TYPE: PRT
<213> ORGANISM: Artificial Sequence
<220> FEATURE:
<223> OTHER INFORMATION: synthetic construct

<400> SEQUENCE: 388

Ser Ser Arg Pro Ile Tyr Pro Asn Glu Ser Met Ser Thr Ser Asn Val
1               5                   10                  15

Arg Gly Pro Tyr His Pro Lys
            20

<210> SEQ ID NO 389
<211> LENGTH: 25
<212> TYPE: PRT
<213> ORGANISM: Artificial Sequence
<220> FEATURE:
<223> OTHER INFORMATION: synthetic construct

<400> SEQUENCE: 389

Ser Ser Arg Pro His Asp Pro Asn His Leu Thr His Gln Ala Arg Thr
1               5                   10                  15

Ile Tyr Arg Asn Ala Asn His Thr Lys
            20                  25

<210> SEQ ID NO 390
<211> LENGTH: 25
<212> TYPE: PRT
<213> ORGANISM: Artificial Sequence
<220> FEATURE:
<223> OTHER INFORMATION: synthetic construct

<400> SEQUENCE: 390

Ser Ser Arg Pro Ala Pro Pro Thr Tyr Gln Thr Ala Ser Tyr Pro His
1               5                   10                  15

Asn Leu Pro Ser Lys Arg Lys Met Lys
            20                  25

<210> SEQ ID NO 391
<211> LENGTH: 25
<212> TYPE: PRT
<213> ORGANISM: Artificial Sequence
<220> FEATURE:
<223> OTHER INFORMATION: synthetic construct

<400> SEQUENCE: 391

Ser Ser Arg Pro Gln Val Pro Asp Tyr Leu Ser Pro Thr His Gln Lys
1               5                   10                  15

Lys Ala Phe Leu Glu Ile Pro Thr Lys
            20                  25

<210> SEQ ID NO 392
<211> LENGTH: 25
<212> TYPE: PRT
<213> ORGANISM: Artificial Sequence
<220> FEATURE:
<223> OTHER INFORMATION: synthetic construct

<400> SEQUENCE: 392

Ser Ser Arg Pro His Lys Asn Glu Asn Ile Met Gln Tyr Asn Val Asn
```

```
1               5                   10                  15

Asp Arg Trp His Ile Thr Pro Ala Lys
            20                  25

<210> SEQ ID NO 393
<211> LENGTH: 17
<212> TYPE: PRT
<213> ORGANISM: Artificial sequence
<220> FEATURE:
<223> OTHER INFORMATION: antimicrobial peptide sequence

<400> SEQUENCE: 393

Pro Lys Gly Leu Lys Lys Leu Leu Lys Gly Leu Lys Lys Leu Leu Lys
1               5                   10                  15

Leu

<210> SEQ ID NO 394
<211> LENGTH: 16
<212> TYPE: PRT
<213> ORGANISM: Artificial Sequence
<220> FEATURE:
<223> OTHER INFORMATION: Antimicrobial peptide sequence

<400> SEQUENCE: 394

Lys Gly Leu Lys Lys Leu Leu Lys Gly Leu Lys Lys Leu Leu Lys Leu
1               5                   10                  15

<210> SEQ ID NO 395
<211> LENGTH: 16
<212> TYPE: PRT
<213> ORGANISM: Artificial Sequence
<220> FEATURE:
<223> OTHER INFORMATION: Antimicrobial peptide sequence

<400> SEQUENCE: 395

Lys Gly Leu Lys Lys Leu Leu Lys Leu Leu Lys Lys Leu Leu Lys Leu
1               5                   10                  15

<210> SEQ ID NO 396
<211> LENGTH: 14
<212> TYPE: PRT
<213> ORGANISM: Artificial Sequence
<220> FEATURE:
<223> OTHER INFORMATION: Antimicrobial peptide sequence

<400> SEQUENCE: 396

Leu Lys Lys Leu Leu Lys Leu Leu Lys Leu Leu Lys Leu
1               5                   10

<210> SEQ ID NO 397
<211> LENGTH: 12
<212> TYPE: PRT
<213> ORGANISM: Artificial Sequence
<220> FEATURE:
<223> OTHER INFORMATION: Antimicrobial peptide sequence

<400> SEQUENCE: 397

Leu Lys Lys Leu Leu Lys Leu Leu Lys Leu Leu
1               5                   10

<210> SEQ ID NO 398
<211> LENGTH: 17
<212> TYPE: PRT
<213> ORGANISM: Artificial Sequence
<220> FEATURE:
<223> OTHER INFORMATION: Antimicrobial peptide sequences
```

```
<400> SEQUENCE: 398

Val Ala Lys Lys Leu Ala Lys Leu Ala Lys Leu Ala Lys Leu Ala
1               5                   10                  15

Leu

<210> SEQ ID NO 399
<211> LENGTH: 13
<212> TYPE: PRT
<213> ORGANISM: Artificial Sequence
<220> FEATURE:
<223> OTHER INFORMATION: Antimicrobial peptide sequences

<400> SEQUENCE: 399

Phe Ala Lys Leu Leu Ala Lys Ala Leu Lys Lys Leu Leu
1               5                   10

<210> SEQ ID NO 400
<211> LENGTH: 16
<212> TYPE: PRT
<213> ORGANISM: Artificial Sequence
<220> FEATURE:
<223> OTHER INFORMATION: Antimicrobial peptide sequence

<400> SEQUENCE: 400

Lys Gly Leu Lys Lys Gly Leu Lys Leu Leu Lys Leu Leu Lys Leu
1               5                   10                  15

<210> SEQ ID NO 401
<211> LENGTH: 16
<212> TYPE: PRT
<213> ORGANISM: Artificial Sequence
<220> FEATURE:
<223> OTHER INFORMATION: Antimicrobial peptide sequence

<400> SEQUENCE: 401

Lys Gly Leu Lys Lys Leu Leu Lys Leu Gly Lys Leu Leu Lys Leu
1               5                   10                  15

<210> SEQ ID NO 402
<211> LENGTH: 16
<212> TYPE: PRT
<213> ORGANISM: Artificial Sequence
<220> FEATURE:
<223> OTHER INFORMATION: Antimicrobial peptide sequence

<400> SEQUENCE: 402

Lys Gly Leu Lys Lys Leu Gly Lys Leu Leu Lys Leu Leu Lys Leu
1               5                   10                  15

<210> SEQ ID NO 403
<211> LENGTH: 16
<212> TYPE: PRT
<213> ORGANISM: Artificial Sequence
<220> FEATURE:
<223> OTHER INFORMATION: Antimicrobial peptide sequence

<400> SEQUENCE: 403

Lys Gly Leu Lys Lys Leu Leu Lys Leu Leu Lys Leu Gly Lys Leu
1               5                   10                  15

<210> SEQ ID NO 404
<211> LENGTH: 16
<212> TYPE: PRT
<213> ORGANISM: Artificial Sequence
<220> FEATURE:
```

<223> OTHER INFORMATION: Antimicrobial peptide sequence

<400> SEQUENCE: 404

Lys Gly Leu Lys Lys Leu Leu Lys Leu Leu Lys Lys Leu Gly Lys Leu
1               5                   10                  15

<210> SEQ ID NO 405
<211> LENGTH: 19
<212> TYPE: PRT
<213> ORGANISM: Artificial Sequence
<220> FEATURE:
<223> OTHER INFORMATION: Antimicrobial peptide sequences

<400> SEQUENCE: 405

Phe Ala Leu Ala Leu Lys Ala Leu Lys Lys Leu Lys Lys Ala Leu Lys
1               5                   10                  15

Lys Ala Leu

<210> SEQ ID NO 406
<211> LENGTH: 17
<212> TYPE: PRT
<213> ORGANISM: Artificial Sequence
<220> FEATURE:
<223> OTHER INFORMATION: Antimicrobial peptide sequence

<400> SEQUENCE: 406

Phe Ala Lys Lys Leu Ala Lys Leu Ala Lys Lys Leu Ala Lys Leu Ala
1               5                   10                  15

Leu

<210> SEQ ID NO 407
<211> LENGTH: 13
<212> TYPE: PRT
<213> ORGANISM: Artificial Sequence
<220> FEATURE:
<223> OTHER INFORMATION: Antimicrobial peptide sequences

<400> SEQUENCE: 407

Phe Ala Lys Leu Leu Ala Lys Leu Ala Lys Lys Leu Leu
1               5                   10

<210> SEQ ID NO 408
<211> LENGTH: 15
<212> TYPE: PRT
<213> ORGANISM: Artificial Sequence
<220> FEATURE:
<223> OTHER INFORMATION: Antimicrobial peptide sequences

<400> SEQUENCE: 408

Phe Ala Lys Lys Leu Ala Lys Leu Ala Leu Lys Leu Ala Lys Leu
1               5                   10                  15

<210> SEQ ID NO 409
<211> LENGTH: 10
<212> TYPE: PRT
<213> ORGANISM: Artificial Sequence
<220> FEATURE:
<223> OTHER INFORMATION: Antimicrobial peptide sequences

<400> SEQUENCE: 409

Phe Ala Lys Lys Leu Ala Lys Lys Leu Leu
1               5                   10

<210> SEQ ID NO 410
<211> LENGTH: 13

<212> TYPE: PRT
<213> ORGANISM: Artificial Sequence
<220> FEATURE:
<223> OTHER INFORMATION: Antimicrobial peptide sequence

<400> SEQUENCE: 410

Phe Ala Lys Leu Leu Ala Lys Leu Ala Lys Lys Val Leu
1               5                   10

<210> SEQ ID NO 411
<211> LENGTH: 13
<212> TYPE: PRT
<213> ORGANISM: Artificial Sequence
<220> FEATURE:
<223> OTHER INFORMATION: Antimicrobial peptide sequences

<400> SEQUENCE: 411

Lys Tyr Lys Lys Ala Leu Lys Lys Leu Ala Lys Leu Leu
1               5                   10

<210> SEQ ID NO 412
<211> LENGTH: 12
<212> TYPE: PRT
<213> ORGANISM: Artificial Sequence
<220> FEATURE:
<223> OTHER INFORMATION: Antimicrobial peptide sequences

<400> SEQUENCE: 412

Phe Ala Leu Leu Lys Ala Leu Leu Lys Lys Ala Leu
1               5                   10

<210> SEQ ID NO 413
<211> LENGTH: 14
<212> TYPE: PRT
<213> ORGANISM: Artificial Sequence
<220> FEATURE:
<223> OTHER INFORMATION: Antimicrobial peptide sequence

<400> SEQUENCE: 413

Lys Arg Leu Phe Lys Lys Leu Lys Phe Ser Leu Arg Lys Tyr
1               5                   10

<210> SEQ ID NO 414
<211> LENGTH: 14
<212> TYPE: PRT
<213> ORGANISM: Artificial Sequence
<220> FEATURE:
<223> OTHER INFORMATION: Antimicrobial peptide sequence

<400> SEQUENCE: 414

Lys Arg Leu Phe Lys Lys Leu Leu Phe Ser Leu Arg Lys Tyr
1               5                   10

<210> SEQ ID NO 415
<211> LENGTH: 14
<212> TYPE: PRT
<213> ORGANISM: Artificial Sequence
<220> FEATURE:
<223> OTHER INFORMATION: Antimicrobial peptide sequence

<400> SEQUENCE: 415

Leu Leu Leu Phe Leu Leu Lys Lys Arg Lys Lys Arg Lys Tyr
1               5                   10

<210> SEQ ID NO 416
<211> LENGTH: 36
<212> TYPE: PRT

<213> ORGANISM: Hyalophora cecropia

<400> SEQUENCE: 416

Lys Trp Lys Leu Phe Lys Lys Ile Glu Lys Val Gly Gln Asn Ile Arg
1               5                   10                  15

Asp Gly Ile Ile Lys Ala Gly Pro Ala Val Ala Trp Gly Gln Ala Thr
            20                  25                  30

Gln Ile Ala Lys
        35

<210> SEQ ID NO 417
<211> LENGTH: 23
<212> TYPE: PRT
<213> ORGANISM: Xenopus laevis

<400> SEQUENCE: 417

Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 418
<211> LENGTH: 22
<212> TYPE: PRT
<213> ORGANISM: Xenopus laevis

<400> SEQUENCE: 418

Gly Ile Gly Lys Phe Leu Lys Lys Ala Lys Lys Phe Gly Lys Ala Phe
1               5                   10                  15

Val Lys Ile Leu Lys Lys
            20

<210> SEQ ID NO 419
<211> LENGTH: 12
<212> TYPE: PRT
<213> ORGANISM: Bos taurus

<400> SEQUENCE: 419

Arg Leu Cys Arg Ile Val Val Ile Arg Val Cys Arg
1               5                   10

<210> SEQ ID NO 420
<211> LENGTH: 13
<212> TYPE: PRT
<213> ORGANISM: Bos taurus

<400> SEQUENCE: 420

Ile Leu Pro Trp Lys Trp Pro Trp Trp Pro Trp Arg Arg
1               5                   10

<210> SEQ ID NO 421
<211> LENGTH: 24
<212> TYPE: PRT
<213> ORGANISM: Homo sapiens

<400> SEQUENCE: 421

Asp Ser His Ala Lys Arg His His Gly Tyr Lys Arg Lys Phe His Glu
1               5                   10                  15

Lys His His Ser His Arg Gly Tyr
            20

<210> SEQ ID NO 422

```
<211> LENGTH: 7
<212> TYPE: PRT
<213> ORGANISM: Artificial Sequence
<220> FEATURE:
<223> OTHER INFORMATION: Pigment binding peptide sequence

<400> SEQUENCE: 422

Met Pro Pro Pro Leu Met Gln
1               5

<210> SEQ ID NO 423
<211> LENGTH: 7
<212> TYPE: PRT
<213> ORGANISM: Artificial Sequence
<220> FEATURE:
<223> OTHER INFORMATION: Pigment binding peptide sequences

<400> SEQUENCE: 423

Phe His Glu Asn Trp Pro Ser
1               5

<210> SEQ ID NO 424
<211> LENGTH: 12
<212> TYPE: PRT
<213> ORGANISM: Artificial Sequence
<220> FEATURE:
<223> OTHER INFORMATION: Pigment binding peptide sequence

<400> SEQUENCE: 424

Arg Thr Ala Pro Thr Thr Pro Leu Leu Leu Ser Leu
1               5                   10

<210> SEQ ID NO 425
<211> LENGTH: 12
<212> TYPE: PRT
<213> ORGANISM: Artificial Sequence
<220> FEATURE:
<223> OTHER INFORMATION: Pigment binding peptide sequence

<400> SEQUENCE: 425

Trp His Leu Ser Trp Ser Pro Val Pro Leu Pro Thr
1               5                   10

<210> SEQ ID NO 426
<211> LENGTH: 7
<212> TYPE: PRT
<213> ORGANISM: Artificial Sequence
<220> FEATURE:
<223> OTHER INFORMATION: Pigment binding peptide sequence

<400> SEQUENCE: 426

Pro His Ala Arg Leu Val Gly
1               5

<210> SEQ ID NO 427
<211> LENGTH: 7
<212> TYPE: PRT
<213> ORGANISM: Artificial Sequence
<220> FEATURE:
<223> OTHER INFORMATION: Pigment binding peptide sequence

<400> SEQUENCE: 427

Asn Ile Pro Tyr His His Pro
1               5

<210> SEQ ID NO 428
<211> LENGTH: 7
```

```
<212> TYPE: PRT
<213> ORGANISM: Artificial Sequence
<220> FEATURE:
<223> OTHER INFORMATION: Pigment binding peptide sequences

<400> SEQUENCE: 428

Thr Thr Met Pro Ala Ile Pro
1               5

<210> SEQ ID NO 429
<211> LENGTH: 7
<212> TYPE: PRT
<213> ORGANISM: Artificial Sequence
<220> FEATURE:
<223> OTHER INFORMATION: Pigment binding peptide sequence

<400> SEQUENCE: 429

His Asn Leu Pro Pro Arg Ser
1               5

<210> SEQ ID NO 430
<211> LENGTH: 12
<212> TYPE: PRT
<213> ORGANISM: Artificial Sequence
<220> FEATURE:
<223> OTHER INFORMATION: Pigment binding peptide sequences

<400> SEQUENCE: 430

Ala His Lys Thr Gln Met Gly Val Arg Gln Pro Ala
1               5                   10

<210> SEQ ID NO 431
<211> LENGTH: 12
<212> TYPE: PRT
<213> ORGANISM: Artificial Sequence
<220> FEATURE:
<223> OTHER INFORMATION: Pigment binding peptide sequence

<400> SEQUENCE: 431

Ala Asp Asn Val Gln Met Gly Val Ser His Thr Pro
1               5                   10

<210> SEQ ID NO 432
<211> LENGTH: 12
<212> TYPE: PRT
<213> ORGANISM: Artificial Sequence
<220> FEATURE:
<223> OTHER INFORMATION: Pigment binding peptide sequences

<400> SEQUENCE: 432

Ala His Asn Ala Gln Met Gly Val Ser His Pro Pro
1               5                   10

<210> SEQ ID NO 433
<211> LENGTH: 12
<212> TYPE: PRT
<213> ORGANISM: Artificial Sequence
<220> FEATURE:
<223> OTHER INFORMATION: Pigment binding peptide sequence

<400> SEQUENCE: 433

Ala Asp Tyr Val Gly Met Gly Val Ser His Arg Pro
1               5                   10

<210> SEQ ID NO 434
<211> LENGTH: 12
<212> TYPE: PRT
```

```
<213> ORGANISM: Artificial Sequence
<220> FEATURE:
<223> OTHER INFORMATION: Pigment binding peptide sequence

<400> SEQUENCE: 434

Ser Val Ser Val Gly Met Lys Pro Ser Pro Arg Pro
1               5                   10

<210> SEQ ID NO 435
<211> LENGTH: 7
<212> TYPE: PRT
<213> ORGANISM: Artificial Sequence
<220> FEATURE:
<223> OTHER INFORMATION: Pigment binding peptide sequence

<400> SEQUENCE: 435

Tyr Pro Asn Thr Ala Leu Val
1               5

<210> SEQ ID NO 436
<211> LENGTH: 7
<212> TYPE: PRT
<213> ORGANISM: Artificial Sequence
<220> FEATURE:
<223> OTHER INFORMATION: Pigment binding peptide sequences

<400> SEQUENCE: 436

Val Ala Thr Arg Ile Val Ser
1               5

<210> SEQ ID NO 437
<211> LENGTH: 12
<212> TYPE: PRT
<213> ORGANISM: Artificial Sequence
<220> FEATURE:
<223> OTHER INFORMATION: Pigment binding peptide sequences

<400> SEQUENCE: 437

His Ser Leu Lys Asn Ser Met Leu Thr Val Met Ala
1               5                   10

<210> SEQ ID NO 438
<211> LENGTH: 7
<212> TYPE: PRT
<213> ORGANISM: Artificial Sequence
<220> FEATURE:
<223> OTHER INFORMATION: Pigment binding peptide sequences

<400> SEQUENCE: 438

Asn Tyr Pro Thr Gln Ala Pro
1               5

<210> SEQ ID NO 439
<211> LENGTH: 7
<212> TYPE: PRT
<213> ORGANISM: Artificial Sequence
<220> FEATURE:
<223> OTHER INFORMATION: Pigment binding peptide sequences

<400> SEQUENCE: 439

Lys Cys Cys Tyr Ser Val Gly
1               5

<210> SEQ ID NO 440
<211> LENGTH: 12
<212> TYPE: PRT
<213> ORGANISM: Artificial Sequence
```

```
<220> FEATURE:
<223> OTHER INFORMATION: Pigment binding peptide sequences

<400> SEQUENCE: 440

Arg His Asp Leu Asn Thr Trp Leu Pro Pro Val Lys
1               5                   10

<210> SEQ ID NO 441
<211> LENGTH: 12
<212> TYPE: PRT
<213> ORGANISM: Artificial Sequence
<220> FEATURE:
<223> OTHER INFORMATION: Pigment binding peptide sequence

<400> SEQUENCE: 441

Glu Ile Ser Leu Pro Ala Lys Leu Pro Ser Ala Ser
1               5                   10

<210> SEQ ID NO 442
<211> LENGTH: 12
<212> TYPE: PRT
<213> ORGANISM: Artificial Sequence
<220> FEATURE:
<223> OTHER INFORMATION: Pigment binding peptide sequence

<400> SEQUENCE: 442

Ser Asp Tyr Val Gly Met Arg Pro Ser Pro Arg His
1               5                   10

<210> SEQ ID NO 443
<211> LENGTH: 12
<212> TYPE: PRT
<213> ORGANISM: Artificial Sequence
<220> FEATURE:
<223> OTHER INFORMATION: Pigment binding peptide sequences

<400> SEQUENCE: 443

Ser Asp Tyr Val Gly Met Arg Leu Ser Pro Ser Gln
1               5                   10

<210> SEQ ID NO 444
<211> LENGTH: 12
<212> TYPE: PRT
<213> ORGANISM: Artificial Sequence
<220> FEATURE:
<223> OTHER INFORMATION: Pigment binding peptide sequences

<400> SEQUENCE: 444

Ser Val Ser Val Gly Ile Gln Pro Ser Pro Arg Pro
1               5                   10

<210> SEQ ID NO 445
<211> LENGTH: 12
<212> TYPE: PRT
<213> ORGANISM: Artificial Sequence
<220> FEATURE:
<223> OTHER INFORMATION: Pigment binding peptide sequence

<400> SEQUENCE: 445

Tyr Val Ser Val Gly Ile Lys Pro Ser Pro Arg Pro
1               5                   10

<210> SEQ ID NO 446
<211> LENGTH: 12
<212> TYPE: PRT
<213> ORGANISM: Artificial Sequence
<220> FEATURE:
```

```
<223> OTHER INFORMATION: Pigment binding peptide sequences

<400> SEQUENCE: 446

Tyr Val Cys Glu Gly Ile His Pro Cys Pro Arg Pro
1               5                   10

<210> SEQ ID NO 447
<211> LENGTH: 7
<212> TYPE: PRT
<213> ORGANISM: Artificial Sequence
<220> FEATURE:
<223> OTHER INFORMATION: Cellulose Binding Peptide

<400> SEQUENCE: 447

Val Pro Arg Val Thr Ser Ile
1               5

<210> SEQ ID NO 448
<211> LENGTH: 7
<212> TYPE: PRT
<213> ORGANISM: Artificial Sequence
<220> FEATURE:
<223> OTHER INFORMATION: Cellulose-Binding Peptide

<400> SEQUENCE: 448

Met Ala Asn His Asn Leu Ser
1               5

<210> SEQ ID NO 449
<211> LENGTH: 7
<212> TYPE: PRT
<213> ORGANISM: Artificial Sequence
<220> FEATURE:
<223> OTHER INFORMATION: Cellulose-Binding Peptide

<400> SEQUENCE: 449

Phe His Glu Asn Trp Pro Ser
1               5

<210> SEQ ID NO 450
<211> LENGTH: 12
<212> TYPE: PRT
<213> ORGANISM: Artificial sequence
<220> FEATURE:
<223> OTHER INFORMATION: Cellulose-Binding Peptide

<400> SEQUENCE: 450

Thr His Lys Thr Ser Thr Gln Arg Leu Leu Ala Ala
1               5                   10

<210> SEQ ID NO 451
<211> LENGTH: 12
<212> TYPE: PRT
<213> ORGANISM: Artificial sequence
<220> FEATURE:
<223> OTHER INFORMATION: Cellulose-Binding Peptide

<400> SEQUENCE: 451

Lys Cys Cys Tyr Val Asn Val Gly Ser Val Phe Ser
1               5                   10

<210> SEQ ID NO 452
<211> LENGTH: 12
<212> TYPE: PRT
<213> ORGANISM: Artificial sequence
<220> FEATURE:
<223> OTHER INFORMATION: Cellulose-Binding Peptide
```

<400> SEQUENCE: 452

Ala His Met Gln Phe Arg Thr Ser Leu Thr Pro His
1               5                   10

<210> SEQ ID NO 453
<211> LENGTH: 12
<212> TYPE: PRT
<213> ORGANISM: Artificial sequence
<220> FEATURE:
<223> OTHER INFORMATION: Poly(ethylene terephthalate)-Binding Peptide

<400> SEQUENCE: 453

Gly Thr Ser Asp His Met Ile Met Pro Phe Phe Asn
1               5                   10

<210> SEQ ID NO 454
<211> LENGTH: 12
<212> TYPE: PRT
<213> ORGANISM: Artificial Sequence
<220> FEATURE:
<223> OTHER INFORMATION: Polymethylmethacrylate-binding peptide

<400> SEQUENCE: 454

Thr Ala Val Met Asn Val Val Asn Asn Gln Leu Ser
1               5                   10

<210> SEQ ID NO 455
<211> LENGTH: 12
<212> TYPE: PRT
<213> ORGANISM: Artificial Sequence
<220> FEATURE:
<223> OTHER INFORMATION: Polymethylmethacrylate-binding peptide

<400> SEQUENCE: 455

Val Pro Trp Trp Ala Pro Ser Lys Leu Ser Met Gln
1               5                   10

<210> SEQ ID NO 456
<211> LENGTH: 12
<212> TYPE: PRT
<213> ORGANISM: Artificial Sequence
<220> FEATURE:
<223> OTHER INFORMATION: Polymethylmethacrylate-binding peptide

<400> SEQUENCE: 456

Met Val Met Ala Pro His Thr Pro Arg Ala Arg Ser
1               5                   10

<210> SEQ ID NO 457
<211> LENGTH: 12
<212> TYPE: PRT
<213> ORGANISM: Artificial Sequence
<220> FEATURE:
<223> OTHER INFORMATION: Polymethylmethacrylate-binding peptide

<400> SEQUENCE: 457

Thr Tyr Pro Asn Trp Ala His Leu Leu Ser His Tyr
1               5                   10

<210> SEQ ID NO 458
<211> LENGTH: 7
<212> TYPE: PRT
<213> ORGANISM: Artificial Sequence
<220> FEATURE:
<223> OTHER INFORMATION: Polymethylmethacrylate-binding peptide

```
<400> SEQUENCE: 458

Thr Pro Trp Trp Arg Ile Thr
1               5

<210> SEQ ID NO 459
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 459

Asp Leu Thr Leu Pro Phe His
1               5

<210> SEQ ID NO 460
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 460

Gly Thr Ser Ile Pro Ala Met
1               5

<210> SEQ ID NO 461
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 461

His His Lys His Val Val Ala
1               5

<210> SEQ ID NO 462
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 462

His His His Lys His Phe Met
1               5

<210> SEQ ID NO 463
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 463

His His His Arg His Gln Gly
1               5

<210> SEQ ID NO 464
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 464
```

```
His His Trp His Ala Pro Arg
1               5

<210> SEQ ID NO 465
<211> LENGTH: 7
<212> TYPE: PRT
<213> ORGANISM: Artificial Sequence
<220> FEATURE:
<223> OTHER INFORMATION: Nylon-Binding Peptide

<400> SEQUENCE: 465

Lys Thr Pro Pro Thr Arg Pro
1               5

<210> SEQ ID NO 466
<211> LENGTH: 7
<212> TYPE: PRT
<213> ORGANISM: Artificial Sequence
<220> FEATURE:
<223> OTHER INFORMATION: Nylon-Binding Peptide

<400> SEQUENCE: 466

Val Ile Asn Pro Asn Leu Asp
1               5

<210> SEQ ID NO 467
<211> LENGTH: 7
<212> TYPE: PRT
<213> ORGANISM: Artificial Sequence
<220> FEATURE:
<223> OTHER INFORMATION: Nylon-Binding Peptide

<400> SEQUENCE: 467

Lys Val Trp Ile Val Ser Thr
1               5

<210> SEQ ID NO 468
<211> LENGTH: 7
<212> TYPE: PRT
<213> ORGANISM: Artificial Sequence
<220> FEATURE:
<223> OTHER INFORMATION: Nylon-Binding  Peptide

<400> SEQUENCE: 468

Ala Glu Pro Val Ala Met Leu
1               5

<210> SEQ ID NO 469
<211> LENGTH: 7
<212> TYPE: PRT
<213> ORGANISM: Artificial Sequence
<220> FEATURE:
<223> OTHER INFORMATION: Nylon-Binding Peptide

<400> SEQUENCE: 469

Ala Glu Leu Val Ala Met Leu
1               5

<210> SEQ ID NO 470
<211> LENGTH: 7
<212> TYPE: PRT
<213> ORGANISM: Artificial Sequence
<220> FEATURE:
<223> OTHER INFORMATION: Nylon-Binding Peptide

<400> SEQUENCE: 470
```

```
His Ser Leu Arg Leu Asp Trp
1               5

<210> SEQ ID NO 471
<211> LENGTH: 12
<212> TYPE: PRT
<213> ORGANISM: Artificial Sequence
<220> FEATURE:
<223> OTHER INFORMATION: Poly(tetrafluoroethylene)-Binding Peptide

<400> SEQUENCE: 471

Glu Ser Ser Tyr Ser Trp Ser Pro Ala Arg Leu Ser
1               5                   10

<210> SEQ ID NO 472
<211> LENGTH: 12
<212> TYPE: PRT
<213> ORGANISM: Artificial Sequence
<220> FEATURE:
<223> OTHER INFORMATION: Poly(tetrafluoroethylene)-Binding Peptide

<400> SEQUENCE: 472

Gly Pro Leu Lys Leu Leu His Ala Trp Trp Gln Pro
1               5                   10

<210> SEQ ID NO 473
<211> LENGTH: 7
<212> TYPE: PRT
<213> ORGANISM: Artificial Sequence
<220> FEATURE:
<223> OTHER INFORMATION: Poly(tetrafluoroethylene)-Binding Peptide

<400> SEQUENCE: 473

Asn Ala Leu Thr Arg Pro Val
1               5

<210> SEQ ID NO 474
<211> LENGTH: 7
<212> TYPE: PRT
<213> ORGANISM: Artificial Sequence
<220> FEATURE:
<223> OTHER INFORMATION: Poly(tetrafluoroethylene)-Binding Peptide

<400> SEQUENCE: 474

Ser Ala Pro Ser Ser Lys Asn
1               5

<210> SEQ ID NO 475
<211> LENGTH: 12
<212> TYPE: PRT
<213> ORGANISM: Artificial Sequence
<220> FEATURE:
<223> OTHER INFORMATION: Poly(tetrafluoroethylene)-Binding Peptide

<400> SEQUENCE: 475

Ser Val Ser Val Gly Met Lys Pro Ser Pro Arg Pro
1               5                   10

<210> SEQ ID NO 476
<211> LENGTH: 12
<212> TYPE: PRT
<213> ORGANISM: Artificial Sequence
<220> FEATURE:
<223> OTHER INFORMATION: Poly(tetrafluoroethylene)-Binding Peptide

<400> SEQUENCE: 476

Ser Tyr Tyr Ser Leu Pro Pro Ile Phe His Ile Pro
```

```
<210> SEQ ID NO 477
<211> LENGTH: 12
<212> TYPE: PRT
<213> ORGANISM: Artificial Sequence
<220> FEATURE:
<223> OTHER INFORMATION: Poly(tetrafluoroethylene)-Binding Peptide

<400> SEQUENCE: 477

Thr Phe Thr Pro Tyr Ser Ile Thr His Ala Leu Leu
1               5                   10

<210> SEQ ID NO 478
<211> LENGTH: 12
<212> TYPE: PRT
<213> ORGANISM: Artificial Sequence
<220> FEATURE:
<223> OTHER INFORMATION: Poly(tetrafluoroethylene)-Binding Peptide

<400> SEQUENCE: 478

Thr Met Gly Phe Thr Ala Pro Arg Phe Pro His Tyr
1               5                   10

<210> SEQ ID NO 479
<211> LENGTH: 12
<212> TYPE: PRT
<213> ORGANISM: Artificial Sequence
<220> FEATURE:
<223> OTHER INFORMATION: Poly(tetrafluoroethylene)-Binding Peptide

<400> SEQUENCE: 479

Thr Asn Pro Phe Pro Pro Pro Ser Ser Pro Ala
1               5                   10

<210> SEQ ID NO 480
<211> LENGTH: 27
<212> TYPE: PRT
<213> ORGANISM: artificial sequence
<220> FEATURE:
<223> OTHER INFORMATION: Clay-binding peptide

<400> SEQUENCE: 480

Gly His Gly Ser Pro Ser Asn Ser His His Gly Ser Lys Lys Cys Asp
1               5                   10                  15

Met Gly Asn Ser Arg Ala Lys Cys Lys Arg Leu
            20                  25

<210> SEQ ID NO 481
<211> LENGTH: 27
<212> TYPE: PRT
<213> ORGANISM: artificial sequence
<220> FEATURE:
<223> OTHER INFORMATION: Clay-binding peptide

<400> SEQUENCE: 481

Ser Asp Arg His Asn Leu Arg Asn Ser Trp Ser Ile Ser Arg His Cys
1               5                   10                  15

Arg Arg Lys Gln Gly Arg Cys Leu Pro Ala His
            20                  25

<210> SEQ ID NO 482
<211> LENGTH: 27
<212> TYPE: PRT
<213> ORGANISM: artificial sequence
<220> FEATURE:
```

<223> OTHER INFORMATION: Clay-binding peptide

<400> SEQUENCE: 482

Lys Lys Ser Asn Lys Gly His His Pro Ser Lys Gly Lys Gly Pro
1               5                   10                  15

Pro Trp Ser Glu Trp Asp Lys Lys Asn Gly Pro
            20                  25

<210> SEQ ID NO 483
<211> LENGTH: 27
<212> TYPE: PRT
<213> ORGANISM: artificial sequence
<220> FEATURE:
<223> OTHER INFORMATION: Clay-binding peptide

<400> SEQUENCE: 483

Lys Lys Ser Asn Lys Gly Pro His Pro Ser Lys Gly Lys Gly Pro
1               5                   10                  15

Pro Trp Ser Glu Trp Asp Lys Lys Asn Gly Pro
            20                  25

<210> SEQ ID NO 484
<211> LENGTH: 22
<212> TYPE: PRT
<213> ORGANISM: artificial sequence
<220> FEATURE:
<223> OTHER INFORMATION: Clay-binding peptide

<400> SEQUENCE: 484

Val Gly Arg His His Ser Lys Ala Lys Gln Lys Arg Pro His Gly Gly
1               5                   10                  15

Lys Gly Gln Asn Lys Asn
            20

<210> SEQ ID NO 485
<211> LENGTH: 22
<212> TYPE: PRT
<213> ORGANISM: artificial sequence
<220> FEATURE:
<223> OTHER INFORMATION: Clay-binding peptide

<400> SEQUENCE: 485

Val Gly Arg His His Pro Lys Ala Lys Gln Lys Arg Pro His Gly Gly
1               5                   10                  15

Lys Gly Gln Asn Lys Asn
            20

<210> SEQ ID NO 486
<211> LENGTH: 17
<212> TYPE: PRT
<213> ORGANISM: artificial sequence
<220> FEATURE:
<223> OTHER INFORMATION: Clay-binding peptide

<400> SEQUENCE: 486

Gly Arg Arg Pro Arg Ala Arg Gly Arg Ser Arg Arg Gly Ser Thr Lys
1               5                   10                  15

Thr

<210> SEQ ID NO 487
<211> LENGTH: 19
<212> TYPE: PRT
<213> ORGANISM: artificial sequence
<220> FEATURE:

<223> OTHER INFORMATION: Clay-binding peptide

<400> SEQUENCE: 487

Leu Gly Val Ile Arg Asn His Val Val Arg Gly Arg Arg His His Gln
1               5                   10                  15

His Val Arg

<210> SEQ ID NO 488
<211> LENGTH: 27
<212> TYPE: PRT
<213> ORGANISM: artificial sequence
<220> FEATURE:
<223> OTHER INFORMATION: Clay-binding peptide

<400> SEQUENCE: 488

Gln Pro Gly Arg Pro Thr Glu Val His Pro Glu Leu Val Arg Lys Ser
1               5                   10                  15

Ala Tyr Leu Val Asn Pro Ser Glu Asp Ile Arg
            20                  25

<210> SEQ ID NO 489
<211> LENGTH: 27
<212> TYPE: PRT
<213> ORGANISM: artificial sequence
<220> FEATURE:
<223> OTHER INFORMATION: Clay-binding peptide

<400> SEQUENCE: 489

His Arg Ser Glu Lys Pro Lys Asn Val Lys Tyr Lys Arg Gly Tyr Trp
1               5                   10                  15

Glu Arg Gly Asn Gln Lys Lys His Gly Pro Gly
            20                  25

<210> SEQ ID NO 490
<211> LENGTH: 27
<212> TYPE: PRT
<213> ORGANISM: artificial sequence
<220> FEATURE:
<223> OTHER INFORMATION: Clay-binding peptide

<400> SEQUENCE: 490

Gly Ser His Lys Arg Arg Gly Ser Tyr Ala Leu Leu Arg Thr Arg Gly
1               5                   10                  15

Val Gly Arg Gln Ala Glu Leu Glu His Leu Leu
            20                  25

<210> SEQ ID NO 491
<211> LENGTH: 27
<212> TYPE: PRT
<213> ORGANISM: artificial sequence
<220> FEATURE:
<223> OTHER INFORMATION: Clay-binding peptide

<400> SEQUENCE: 491

Val Gly Glu Lys Pro Arg Arg Lys Ser Lys Gly Ala Lys Ala Lys Lys
1               5                   10                  15

Ala Arg Thr Lys Glu Glu Lys Leu Pro Lys Asn
            20                  25

<210> SEQ ID NO 492
<211> LENGTH: 27
<212> TYPE: PRT
<213> ORGANISM: artificial sequence
<220> FEATURE:

<223> OTHER INFORMATION: Clay-binding peptide

<400> SEQUENCE: 492

Asn Lys Gly His Lys Gln Ser Gly Ser Pro Arg His Ser Asn Lys Lys
1               5                   10                  15
Glu Lys Lys Thr Gln Gln Lys Arg Gly Gln Pro
            20                  25

<210> SEQ ID NO 493
<211> LENGTH: 27
<212> TYPE: PRT
<213> ORGANISM: artificial sequence
<220> FEATURE:
<223> OTHER INFORMATION: Clay-binding peptide

<400> SEQUENCE: 493

His Trp Gly Ser Gln His Lys Thr Gly Leu Arg Asn His Lys Arg Ser
1               5                   10                  15
Arg Arg Asp Ser Leu Gly Lys Arg Gly Thr Asp
            20                  25

<210> SEQ ID NO 494
<211> LENGTH: 27
<212> TYPE: PRT
<213> ORGANISM: artificial sequence
<220> FEATURE:
<223> OTHER INFORMATION: Clay-binding peptide

<400> SEQUENCE: 494

Lys Gly Trp Gly Ser Ser Ser Gly Pro Pro Gly Leu Thr Gly Lys Ala
1               5                   10                  15
Leu Gly Lys Gly Arg Leu Lys Pro Lys Lys Lys
            20                  25

<210> SEQ ID NO 495
<211> LENGTH: 24
<212> TYPE: PRT
<213> ORGANISM: artificial sequence
<220> FEATURE:
<223> OTHER INFORMATION: Clay-binding peptide

<400> SEQUENCE: 495

Ser Ser Lys Ser Gly Ala Pro Phe Arg Val Pro Ile Cys Phe Thr Ala
1               5                   10                  15
Pro Arg Pro Gln Lys Thr Leu Gly
            20

<210> SEQ ID NO 496
<211> LENGTH: 14
<212> TYPE: PRT
<213> ORGANISM: artificial sequence
<220> FEATURE:
<223> OTHER INFORMATION: synthetic construct - gold-binding peptide

<400> SEQUENCE: 496

Met His Gly Lys Thr Gln Ala Thr Ser Gly Thr Ile Gln Ser
1               5                   10

<210> SEQ ID NO 497
<211> LENGTH: 148
<212> TYPE: PRT
<213> ORGANISM: artificial seqeunce
<220> FEATURE:
<223> OTHER INFORMATION: synthetic construct

<400> SEQUENCE: 497

Met Ala Ser His Gln His Phe His Trp Gln Phe Glu Gln Gln Gly Gly
1               5                   10                  15

Ala Gly Gln Gly Gly Leu Gly Ser Gln Gly Ala Gly Gln Gly Ala Gly
            20                  25                  30

His Gln His Phe His Trp Gln Phe Glu Gln Gln Gly Gly Ala Gly Gln
        35                  40                  45

Gly Gly Tyr Gly Gly Leu Gly Ser Gln Gly Ala Gly Arg Gly Gly Gln
    50                  55                  60

Gly Ala Gly His Gln His Phe His Trp Gln Phe Glu Gln Gln Gly Gly
65                  70                  75                  80

Ala Gly Gln Gly Gly Tyr Gly Gly Leu Gly Ser Gln Gly Ala Gly Arg
                85                  90                  95

Gly Gly Leu Gly Gly Gln Gly Ala Gly His Gln His Phe His Trp Gln
            100                 105                 110

Phe Glu Gln Gln Gly Pro Gly Ser Gly Gly Ala Gly Ser Pro Gly Ser
                115                 120                 125

Ala Gly Gly Pro Gly Ser Met His Gly Lys Thr Gln Ala Thr Ser Gly
            130                 135                 140

Thr Ile Gln Ser
145

<210> SEQ ID NO 498
<211> LENGTH: 129
<212> TYPE: PRT
<213> ORGANISM: artificial sequence
<220> FEATURE:
<223> OTHER INFORMATION: synthetic construct

<400> SEQUENCE: 498

Pro Ser Ala Gln Ser Gln Leu Pro Asp Lys His Ser Gly Leu His Glu
1               5                   10                  15

Arg Ala Pro Gln Arg Tyr Gly Pro Glu Pro Glu Pro Glu Pro Glu Pro
            20                  25                  30

Ile Pro Glu Pro Pro Lys Glu Ala Pro Val Val Ile Glu Lys Pro Lys
        35                  40                  45

Pro Lys Pro Lys Pro Lys Pro Lys Pro Pro Ala His Asp His Lys Asn
    50                  55                  60

Gln Lys Glu Thr His Gln Arg His Ala Ala Gly Ser Gly Gly Gly Gly
65                  70                  75                  80

Ser Pro Trp Ala Pro Glu Lys Asp His Met Gln Leu Met Lys Gly Lys
                85                  90                  95

Gly Lys Gly Lys Gly Lys Gly Lys Gly Lys Gly Lys Gly Lys Gly Lys
            100                 105                 110

Gly Lys Gly Trp Ala Pro Glu Lys Asp His Met Gln Leu Met Lys Gly
            115                 120                 125

Lys

<210> SEQ ID NO 499
<211> LENGTH: 223
<212> TYPE: PRT
<213> ORGANISM: artificial sequence
<220> FEATURE:
<223> OTHER INFORMATION: synthetic construct

<400> SEQUENCE: 499

Met Ala Ser His Gln His Phe His Trp Gln Phe Glu Gln Gln Gly Gly

-continued

```
1               5                   10                  15
Ala Gly Gln Gly Gly Leu Gly Ser Gln Gly Ala Gly Gln Gly Ala Gly
            20                  25                  30

His Gln His Phe His Trp Gln Phe Glu Gln Gln Gly Gly Ala Gly Gln
            35                  40                  45

Gly Gly Tyr Gly Gly Leu Gly Ser Gln Gly Ala Gly Arg Gly Gly Gln
        50                  55                  60

Gly Ala Gly His Gln His Phe His Trp Gln Phe Glu Gln Gln Gly Gly
65                  70                  75                  80

Ala Gly Gln Gly Gly Tyr Gly Gly Leu Gly Ser Gln Gly Ala Gly Arg
                85                  90                  95

Gly Gly Leu Gly Gly Gln Gly Ala Gly His Gln His Phe His Trp Gln
            100                 105                 110

Phe Glu Gln Gln Gly Pro Gly Ser Gly Gly Ala Gly Ser Pro Gly Ser
            115                 120                 125

Ala Gly Gly Pro Gly Ser Asp Pro Ser Ala Gln Ser Gln Leu Pro Asp
            130                 135                 140

Lys His Ser Gly Leu His Glu Arg Ala Pro Gln Arg Tyr Gly Pro Glu
145                 150                 155                 160

Pro Glu Pro Glu Pro Glu Pro Ile Pro Glu Pro Pro Lys Glu Ala Pro
                165                 170                 175

Val Val Ile Glu Lys Pro Lys Pro Lys Pro Lys Pro Lys Pro Lys Pro
            180                 185                 190

Pro Ala His Asp His Lys Asn Gln Lys Glu Thr His Gln Arg His Ala
        195                 200                 205

Ala Gly Ser Gly Gly Gly Gly Ser Pro His His His His His His
        210                 215                 220
```